United States Patent
Gillespie et al.

(10) Patent No.: US 7,875,600 B2
(45) Date of Patent: *Jan. 25, 2011

(54) PYRIMIDINE COMPOUNDS AS PURINE RECEPTOR ANTAGONIST

(75) Inventors: Roger John Gillespie, Wokingham (GB); Richard Simon Todd, Wokingham (GB); Gemma Caroline Stratton, Wokingham (GB); Allan Michael Jordan, Wokingham (GB)

(73) Assignee: Vernalis (R&D) Limited (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/588,757

(22) PCT Filed: Feb. 11, 2005

(86) PCT No.: PCT/GB2005/000498

§ 371 (c)(1),
(2), (4) Date: Jun. 25, 2007

(87) PCT Pub. No.: WO2005/079801

PCT Pub. Date: Sep. 1, 2005

(65) Prior Publication Data

US 2007/0281936 A1 Dec. 6, 2007

(30) Foreign Application Priority Data

Feb. 12, 2004 (GB) .................................. 0403155.5

(51) Int. Cl.
*A61K 31/33* (2006.01)
*C07D 239/00* (2006.01)
(52) U.S. Cl. ...................................... 514/183; 544/242
(58) Field of Classification Search ................... 514/183, 514/256; 544/242
See application file for complete search history.

(56) References Cited

FOREIGN PATENT DOCUMENTS

| WO | WO 02/055084 A | 7/2002 |
|---|---|---|
| WO | WO 2004/029204 A | 4/2004 |
| WO | WO 2004/080979 A | 9/2004 |

OTHER PUBLICATIONS

Dorwald, F. 'Side Reactions in Organic Synthesis: a Guide to Successful Synthesis Design' Wiley-VCH, Preface, p. ix, 2005.*
Jordan, V. 'Tamoxifen: a most unlikely pioneering medicine' Nature Reviews: Drug Discovery, vol. 2, pp. 205-213, 2003.*
Takao, S. et al: Chem. Pharm. Bull., vol. 28, No. 2, 1980, pp. 571-577, XP001206934.
Sakamoto, T. et al.: Chem, Pharm. Bull., vol. 28, No. 1, 1980, pp. 202-207, XP001206935.
Obrecht D et al: "5. A Novel and Officient Approach for the Combinatorial Synthesis of Structurally Diverse Pyrimidines on Solid Support" Helvetica Chimica ACTA, Verlag Helvetica CHIMICA ACTA. Basel, CH, vol. 80, 1997, pp. 65-72. XP002915327 ISSN: 0018-019X.

* cited by examiner

*Primary Examiner*—Brandon J Fetterolf
*Assistant Examiner*—Christopher R Stone
(74) *Attorney, Agent, or Firm*—Banner & Witcoff, Ltd.

(57) ABSTRACT

Compounds of formula (I); wherein $R_1$ is H or NHZ; $R_2$ is optionally substituted aryl or heteroaryl attached via a carbon atom; $R_3$ is H; optionally substituted $C_1$-$C_6$alkyl, $C_2$-$C_6$alkenyl, $C_2$-$C_6$alkynyl, or $C_3$ $C_7$ cycloalkyl, halogen; OH or OR, or $R_4$ is H, optionally substituted $C_1$-$C_6$alkyl, $C_3$ $C_6$alkenyl, $C_3$-$C_6$alkynyl, $C_3$-$C_7$ cycloalkyl, aryl or heteroaryl, $R_5$ is H or optionally substituted $C_1$-$C_6$alkyl, $C_3$-$C_6$alkenyl, $C_3$-$C_6$alkynyl, or $C_3$-$C_7$ cycloalkyl; or $R_4$ and $R_5$ together form a 5 or 6-membered heterocyclic ring; and $R_{10}$ is optionally substituted $C_1$-$C_6$alkyl; are purine receptor, particularly adenosine receptor antagonists, useful for treatment of, inter alia, movement disorders such as Parkinsons disease.

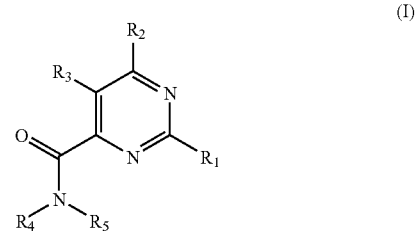

(I)

4 Claims, No Drawings

PYRIMIDINE COMPOUNDS AS PURINE RECEPTOR ANTAGONIST

This application is a U.S. National Stage application of co-pending PCT application PCT/GB2005/000498, filed Feb. 11, 2005, which claims the priority of Great Britain Patent Application No. 0403155.5, filed Feb. 12, 2004. These applications are incorporated herein by reference in its entirety.

The present invention relates to pyrimidine-4-carboxamide derivatives and their use in therapy. In particular, the present invention relates to the treatment of disorders in which the reduction of purinergic neurotransmission could be beneficial. The invention relates in particular to blockade of adenosine receptors and particularly adenosine $A_{2A}$ receptors, and to the treatment of movement disorders such as Parkinson's disease.

Movement disorders constitute a serious health problem, especially amongst the elderly sector of the population. These movement disorders are often the result of brain lesions. Disorders involving the basal ganglia which result in movement disorders include Parkinson's disease, Huntington's chorea and Wilson's disease. Furthermore, dyskinesias often arise as sequalae of cerebral ischaemia and other neurological disorders.

There are four classic symptoms of Parkinson's disease: tremor, rigidity, akinesia and postural changes. The disease is also commonly associated with depression, dementia and overall cognitive decline. Parkinson's disease has a prevalence of 1 per 1,000 of the total population. The incidence increases to 1 per 100 for those aged over 60 years. Degeneration of dopaminergic neurones in the substantia nigra and the subsequent reductions in interstitial concentrations of dopamine in the striatum are critical to the development of Parkinson's disease. Some 80% of cells from the substantia nigra need to be destroyed before the clinical symptoms of Parkinson's disease are manifested.

Current strategies for the treatment of Parkinson's disease are based on transmitter replacement therapy (L-dihydroxyphenylacetic acid (L-DOPA)), inhibition of monoamine oxidase (e.g. Deprenyl®), dopamine receptor agonists (e.g. bromocriptine and apomorphine) and anticholinergics (e.g. benztropine, orphenadrine). Transmitter replacement therapy in particular does not provide consistent clinical benefit, especially after prolonged treatment when "on-off" symptoms develop, and this treatment has also been associated with involuntary movements of athetosis and chorea, nausea and vomiting. Additionally current therapies do not treat the underlying neurodegenerative disorder resulting in a continuing cognitive decline in patients. Despite new drug approvals, there is still a medical need in terms of improved therapies for movement disorders, especially Parkinson's disease. In particular, effective treatments requiring less frequent dosing, effective treatments which are associated with less severe side-effects, and effective treatments which control or reverse the underlying neurodegenerative disorder, are required.

Blockade of $A_2$ adenosine receptors has recently been implicated in the treatment of movement disorders such as Parkinson's disease (Richardson, P. J. et al., *Trends Pharmacol. Sci.* 1997, 18, 338-344) and in the treatment of cerebral ischaemia (Gao, Y. and Phillis, J. W., *Life Sci.* 1994, 55, 61-65). The potential utility of adenosine $A_{2A}$ receptor antagonists in the treatment of movement disorders such as Parkinson's Disease has recently been reviewed (Mally, J. and Stone, T. W., *CNS Drugs,* 1998, 10, 311-320).

Adenosine is a naturally occurring purine nucleoside which has a wide variety of well-documented regulatory functions and physiological effects. The central nervous system (CNS) effects of this endogenous nucleoside have attracted particular attention in drug discovery, owing to the therapeutic potential of purinergic agents in CNS disorders (Jacobson, K. A. et al., *J. Med. Chem.* 1992, 35, 407-422). This therapeutic potential has resulted in considerable recent research endeavour within the field of adenosine receptor agonists and antagonists (Bhagwhat, S. S.; Williams, M. *Exp. Opin. Ther. Patents* 1995, 5, 547-558).

Adenosine receptors represent a subclass ($P_1$) of the group of purine nucleotide and nucleoside receptors known as purinoreceptors. The main pharmacologically distinct adenosine receptor subtypes are known as $A_1$, $A_{2A}$, $A_{2B}$ (of high and low affinity) and $A_3$ (Fredholm, B. B., et al., *Pharmacol. Rev.* 1994, 46, 143-156). The adenosine receptors are present in the CNS (Fredholm, B. B., *News Physiol. Sci.,* 1995, 10, 122-128).

The design of $P_1$ receptor-mediated agents has been reviewed (Jacobson, K. A., Suzuki, F., *Drug Dev. Res.,* 1997, 39, 289-300; Baraldi, P. G. et al., *Curr. Med. Chem.* 1995, 2, 707-722), and such compounds are claimed to be useful in the treatment of cerebral ischemia or neurodegenerative disorders, such as Parkinson's disease (Williams, M. and Burnstock, G. *Purinergic Approaches Exp. Ther.* (1997), 3-26. Editor: Jacobson, Kenneth A.; Jarvis, Michael F. Publisher: Wiley-Liss, New York, N.Y.)

It has been speculated that xanthine derivatives such as caffeine may offer a form of treatment for attention-deficit hyperactivity disorder (ADHD). A number of studies have demonstrated a beneficial effect of caffeine on controlling the symptoms of ADHD (Garfinkel, B. D. et al., *Psychiatry,* 1981, 26, 395-401). Antagonism of adenosine receptors is thought to account for the majority of the behavioural effects of caffeine in humans and thus blockade of adenosine $A_{2A}$ receptors may account for the observed effects of caffeine in ADHD patients. Therefore a selective $A_{2A}$ receptor antagonist may provide an effective treatment for ADHD but without the unwanted side-effects associated with current therapy.

Adenosine receptors have been recognised to play an important role in regulation of sleep patterns, and indeed adenosine antagonists such as caffeine exert potent stimulant effects and can be used to prolong wakefulness (Porkka-Heiskanen, T. et al., *Science,* 1997, 276, 1265-1268). Recent evidence suggests that a substantial part of the actions of adenosine in regulating sleep is mediated through the adenosine $A_{2A}$ receptor (Satoh, S., et al., *Proc. Natl. Acad. Sci., USA,* 1996). Thus, a selective $A_{2A}$ receptor antagonist may be of benefit in counteracting excessive sleepiness in sleep disorders such as hypersomnia or narcolepsy.

It has recently been observed that patients with major depression demonstrate a blunted response to adenosine agonist-induced stimulation in platelets, suggesting that a dysregulation of $A_{2A}$ receptor function may occur during depression (Berk, M. et al, 2001, *Eur. Neuropsychopharmacol.* 11, 183-186). Experimental evidence in animal models has shown that blockade of $A_{2A}$ receptor function confers antidepressant activity (El Yacoubi, M et al. *Br. J. Pharmacol.* 2001, 134, 68-77). Thus, $A_{2A}$ receptor antagonists may offer a novel therapy for the treatment of major depression and other affective disorders in patients.

Also recently, from patent publication WO 2004/108137 (Kyowa Hakko Kogyo), it is now considered that adenosine $A_{2A}$ receptor antagonists are useful in the treatment of anxiety disorders, including panic disorder, agoraphobia, obsessive compulsive disorder, social phobia, post traumatic stress disorder, generalised anxiety disorder and specific phobia.

The pharmacology of adenosine $A_{2A}$ receptors has been reviewed (Ongini, E.; Fredholm, B. B. *Trends Pharmacol. Sci.* 1996, 17(10), 364-372). One potential underlying mechanism in the aforementioned treatment of movement disorders by the blockade of $A_2$ adenosine receptors is the evidence of a functional link between adenosine $A_{2A}$ receptors to dopamine $D_2$ receptors in the CNS. Some of the early studies (e.g. Ferre, S. et al., Stimulation of high-affinity adenosine $A_2$ receptors decreases the affinity of dopamine $D_2$ receptors in rat striatal membranes. *Proc. Natl. Acad. Sci. U.S.A.* 1991, 88, 7238-41) have been summarised in two more recent articles (Fuxe, K. et al., *Adenosine Adenine Nucleotides Mol. Biol. Integr. Physiol.*, [Proc. Int. Symp.], 5th (1995), 499-507. Editors: Belardinelli, Luiz; Pelleg, Amir. Publisher: Kluwer, Boston, Mass.; Ferre, S. et al., *Trends Neurosci.* 1997, 20, 482-487).

As a result of these investigations into the functional role of adenosine $A_{2A}$ receptors in the CNS, especially in vivo studies linking $A_2$ receptors with catalepsy (Ferre et al., *Neurosci. Lett.* 1991, 130, 162-4; Mandhane, S. N. et al., *Eur. J. Pharmacol.* 1997, 328, 135-141) investigations have been made into agents which selectively bind to adenosine $A_{2A}$ receptors as potentially effective treatments for Parkinson's disease.

While many of the potential drugs for treatment of Parkinson's disease have shown benefit in the treatment of movement disorders, an advantage of adenosine $A_{2A}$ antagonist therapy is that the underlying neurodegenerative disorder may also be treated. The neuroprotective effect of adenosine $A_{2A}$ antagonists has been reviewed (Ongini, E.; Adami, M.; Ferri, C.; Bertorelli, R., *Ann. N.Y. Acad. Sci.* 1997, 825 (Neuroprotective Agents), 30-48). In particular, compelling recent evidence suggests that blockade of $A_{2A}$ receptor function confers neuroprotection against MPTP-induced neurotoxicity in mice (Chen, J-F., *J. Neurosci.* 2001, 21, RC143). In addition, several recent studies have shown that consumption of dietary caffeine, a known adenosine $A_{2A}$ receptor antagonist, is associated with a reduced risk of Parkinson's disease in man (Ascherio, A. et al, *Ann Neurol.*, 2001, 50, 56-63; Ross G W, et al., *JAMA*, 2000, 283, 2674-9). Thus, $A_{2A}$ receptor antagonists may offer a novel treatment for conferring neuroprotection in neurodegenerative diseases such as Parkinson's disease.

Xanthine derivatives have been disclosed as adenosine $A_2$ receptor antagonists as useful for treating various diseases caused by hyperfunctioning of adenosine $A_2$ receptors, such as Parkinson's disease (see, for example, EP-A-565377).

One prominent xanthine-derived adenosine $A_{2A}$ selective antagonist is CSC [8-(3-chlorostyryl)caffeine] (Jacobson et al., *FEBS Lett*, 1993, 323, 141-144).

Theophylline (1,3-dimethylxanthine), a bronchodilator drug which is a mixed antagonist at adenosine $A_1$ and $A_{2A}$ receptors, has been studied clinically. To determine whether a formulation of this adenosine receptor antagonist would be of value in Parkinson's disease an open trial was conducted on 15 Parkinsonian patients, treated for up to 12 weeks with a slow release oral theophylline preparation (150 mg/day), yielding serum theophylline levels of 4.44 mg/L after one week. The patients exhibited significant improvements in mean objective disability scores and 11 reported moderate or marked subjective improvement (Mally, J., Stone, T. W. *J. Pharm. Pharmacol.* 1994, 46, 515-517).

KF 17837 [(E)-8-(3,4-dimethoxystyryl)-1,3-dipropyl-7-methylxanthine] is a selective adenosine $A_{2A}$ receptor antagonist which on oral administration significantly ameliorated the cataleptic responses induced by intracerebroventricular administration of an adenosine $A_{2A}$ receptor agonist, CGS 21680. KF 17837 also reduced the catalepsy induced by haloperidol and reserpine. Moreover, KF 17837 potentiated the anticataleptic effects of a subthreshold dose of L-DOPA plus benserazide, suggesting that KF 17837 is a centrally active adenosine $A_{2A}$ receptor antagonist and that the dopaminergic function of the nigrostriatal pathway is potentiated by adenosine $A_{2A}$ receptor antagonists (Kanda, T. et al., *Eur. J. Pharmacol.* 1994, 256, 263-268). The structure activity relationship (SAR) of KF 17837 has been published (Shimada, J. et al., *Bioorg. Med. Chem. Lett.* 1997, 7, 2349-2352). Recent data has also been provided on the $A_{2A}$ receptor antagonist KW-6002 (Kuwana, Y et al., *Soc. Neurosci. Abstr.* 1997, 23, 119.14; and Kanda, T. et al., *Ann. Neurol.* 1998, 43(4), 507-513).

New non-xanthine structures sharing these pharmacological properties include SCH 58261 and its derivatives (Baraldi, P. G. et al., Pyrazolo[4,3-e]-1,2,4-triazolo[1,5-c]pyrimidine Derivatives: Potent and Selective $A_{2A}$ Adenosine Antagonists. *J. Med. Chem.* 1996, 39, 1164-71). SCH 58261 (7-(2-phenylethyl)-5-amino-2-(2-furyl)-pyrazolo-[4,3-e]-1,2,4-triazolo[1,5-c]pyrimidine) is reported as effective in the treatment of movement disorders (Ongini, E. *Drug Dev. Res.* 1997, 42(2), 63-70) and has been followed up by a later series of compounds (Baraldi, P. G. et al., *J. Med. Chem.* 1998, 41(12), 2126-2133). WO-A-01/62233 discloses a series of cyclic heteroaromatic compounds containing at least one nitrogen atom and their use as adenosine receptor modulators. FR-2201083 discloses a series of phenylpyrimidines with analgesic activity.

The foregoing discussion indicates that a potentially effective treatment for movement disorders in humans would comprise agents which act as antagonists at adenosine $A_{2A}$ receptors.

It has now been found that the pyrimidine-4-carboxamide derivatives described herein, which are structurally unrelated to known adenosine receptor antagonists, exhibit unexpected antagonist binding affinity at adenosine ($P_1$) receptors, and in particular at the adenosine $A_{2A}$ receptor. Such compounds may therefore be useful for the treatment of disorders in which the blocking of purine receptors, particularly adenosine receptors and more particularly adenosine $A_{2A}$ receptors, is beneficial, for instance movement disorders, such as disorders of the basal ganglia which result in dyskinesias.

According to the present invention there is provided the use of a compound of formula (1):

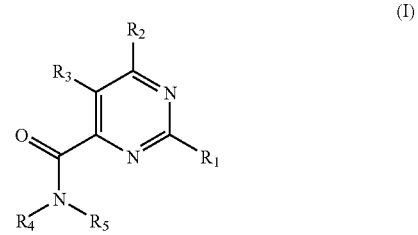

wherein $R_1$ is H or $NH_2$;

$R_2$ is optionally substituted aryl or heteroaryl attached via a carbon atom;

$R_3$ is H; optionally substituted $C_1$-$C_6$alkyl, $C_2$-$C_6$alkenyl, $C_2$-$C_6$alkynyl, or $C_3$-$C_7$ cycloalkyl, halogen; OH or $OR_{10}$;

$R_4$ is H, optionally substituted $C_1$-$C_6$alkyl, $C_3$-$C_6$alkenyl, $C_3$-$C_6$alkynyl, $C_3$-$C_7$ cycloalkyl, aryl or heteroaryl, $R_5$ is H or optionally substituted $C_1$-$C_6$alkyl, $C_3$-$C_6$alkenyl, $C_3$-$C_6$alkynyl, or $C_3$-$C_7$ cycloalkyl;

or $R_4$ and $R_5$ together form a 5 or 6-membered heterocyclic ring;

$R_{10}$ is optionally substituted $C_1$-$C_6$alkyl;

and pharmaceutically acceptable salts and prodrugs thereof, in the manufacture of a medicament for the treatment or prevention of a disorder in which the blocking of purine receptors is beneficial, PROVIDED THAT when $R_2$ is optionally substituted aryl the said use is not the manufacture of a medicament for the treatment or prevention of inflammatory pain.

The class of compounds (I) with which the invention is concerned are antagonists of the $A_{2A}$ receptor, and in many cases are selective antagonists of the $A_{2A}$ receptor over the other adenosine receptor subtypes described herein.

As used herein the term "carboxamide group" refers to a group of formula —$CONR_aR_b$, wherein —$NR_aR_b$ is an amino (including cyclic amino) group actually or notionally derived from ammonia or the amine $HNR_aR_b$.

As used herein, the term "$(C_a$-$C_b)$alkyl" wherein a and b are integers refers to a straight or branched chain alkyl radical having from a to b carbon atoms. Thus when a is 1 and b is 6, for example, the term includes methyl, ethyl, n-propyl, iso-propyl, n-butyl, isobutyl, sec-butyl, t-butyl, n-pentyl and n-hexyl.

As used herein the term "$(C_a$-$C_b)$alkenyl" wherein a and b are integers refers to a straight or branched chain alkenyl moiety having from a to b carbon atoms having at least one double bond of either E or Z stereochemistry where applicable. The term includes, for example, vinyl, allyl, 1- and 2-butenyl and 2-methyl-2-propenyl.

As used herein the term "cycloalkyl" refers to a saturated carbocyclic radical having from 3-8 carbon atoms and includes, for example, cyclopropyl, cyclobutyl, cyclopentyl, cyclohexyl, cycloheptyl and cyclooctyl.

As used herein the term "cycloalkenyl" refers to a carbocyclic radical having from 3-8 carbon atoms containing at least one double bond, and includes, for example, cyclopentenyl, cyclohexenyl, cycloheptenyl and cyclooctenyl.

As used herein the term "aryl" refers to a mono-, bi- or tri-cyclic carbocyclic aromatic radical and includes mono or bicyclic aromatic rings fused to a cycloalkyl ring. Illustrative of such radicals are phenyl, biphenyl and napthyl.

As used herein the term "carbocyclic" refers to a cyclic radical whose ring atoms are all carbon, and includes monocyclic aryl, cycloalkyl, and cycloalkenyl radicals.

As used herein the term "heteroaryl" refers to a mono-, bi- or tri-cyclic aromatic radical containing one or more heteroatoms selected from S, N and O, and includes mono or bicyclic of the foregoing type fused to a cycloalkyl ring. Illustrative of such radicals are thienyl, benzothienyl, furyl, benzofuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyrazinyl, triazinyl, indolyl and indazolyl.

As used herein the unqualified term "heterocyclyl" or "heterocyclic" includes "heteroaryl" as defined above, and in particular refers to a mono-, bi- or tri-cyclic non-aromatic radical containing one or more heteroatoms selected from S, N and O, and to groups consisting of a monocyclic non-aromatic radical containing one or more such heteroatoms which is covalently linked to another such radical or to a monocyclic carbocyclic radical. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzofuranyl, pyranyl, isoxazolyl, benzimidazolyl, methylenedioxyphenyl, ethylenedioxyphenyl, maleimido and succinimido groups.

Unless otherwise specified in the context in which it occurs, the term "substituted" as applied to any moiety herein means substituted with at least one substituent, for example selected from $(C_1$-$C_6)$alkyl, $(C_1$-$C_6)$alkoxy, hydroxy, hydroxy$(C_1$-$C_6)$alkyl, mercapto, mercapto$(C_1$-$C_6)$alkyl, $(C_1$-$C_6)$alkylthio, halo (including fluoro and chloro), trifluoromethyl, trifluoromethoxy, nitro, nitrile (—CN), oxo, phenyl, monocyclic heterocyclic having 5- or 6 ring members, —COOH, —COOR$^A$, —COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —NH$_2$, —NHR$^A$, —NR$^A$R$^B$, —OCONH$_2$, —OCONHR$^A$, —OCONR$^A$R$^B$, —NHCOR$^A$, —NR$^B$COR$^A$, —NHCOOR$^A$, —NR$^B$COOR$^A$, —NHSO$_2$R$^A$, —NR$^B$SO$_2$R$^A$, —NHCONH$_2$, —NR$^A$CONH$_2$, —NHCONHR$^B$, —NR$^A$CONHR$^B$, —NHCONR$^A$R$^B$ or —NR$^A$CONR$^A$R$^B$ wherein R$^A$ and R$^B$ are independently a $(C_1$-$C_6)$alkyl group. An "optional substituent" may be one of the foregoing substituent groups. Where the optional substituent is phenyl, monocyclic heterocyclic having 5- or 6 ring members, then it too may be substituted by any of the foregoing except phenyl and monocyclic heterocyclic having 5- or 6 ring members.

As used herein the term "salt" includes base addition, acid addition and quaternary salts. Compounds of the invention which are acidic can form salts, including pharmaceutically or veterinarily acceptable salts, with bases such as alkali metal hydroxides, e.g. sodium and potassium hydroxides; alkaline earth metal hydroxides e.g. calcium, barium and magnesium hydroxides; with organic bases e.g. N-ethyl piperidine, dibenzylamine and the like. Those compounds (I) which are basic can form salts, including pharmaceutically or veterinarily acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic and p-toluene sulphonic acids and the like.

For a review on suitable salts, see *Handbook of Pharmaceutical Salts: Properties, Selection, and Use* by Stahl and Wermuth (Wiley-VCH, Weinheim, Germany, 2002).

The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Compounds with which the invention is concerned which may exist in one or more stereoisomeric form, because of the presence of asymmetric atoms or rotational restrictions, can exist as a number of stereoisomers with R or S stereochemistry at each chiral centre or as atropisomers with R or S stereochemistry at each chiral axis. The invention includes all such enantiomers and diastereoisomers and mixtures thereof.

So-called 'pro-drugs' of the compounds of formula (I) are also within the scope of the invention. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in *Pro-drugs as Novel Delivery Systems*, Vol. 14, ACS Symposium Series (T. Higuchi and W. Stella) and *Bioreversible*

*Carriers in Drug Design*, Pergamon Press, 1987 (ed. E. B. Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in *Design of Prodrugs* by H. Bundgaard (Elsevier, 1985).

Also included within the scope of the invention are metabolites of compounds of formula (I), that is, compounds formed in vivo upon administration of the drug. Some examples of metabolites include (i) where the compound of formula (I) contains a methyl group, an hydroxymethyl derivative thereof ($-CH_3 \rightarrow -CH_2OH$):
(ii) where the compound of formula (I) contains an alkoxy group, an hydroxy derivative thereof ($-OR \rightarrow -OH$);
(iii) where the compound of formula (I) contains a tertiary amino group, a secondary amino derivative thereof ($-NR^1R^2 \rightarrow -NHR^1$ or $-NHR^2$);
(iv) where the compound of formula (I) contains a secondary amino group, a primary derivative thereof ($-NHR^1 \rightarrow -NH_2$);
(v) where the compound of formula (I) contains a phenyl moiety, a phenol derivative thereof (-Ph->-PhOH); and
(vi) where the compound of formula (I) contains an amide group, a carboxylic acid derivative thereof ($-CONH_2 \rightarrow -COOH$).

The Group $R_1$

In the compounds in accordance with the invention, $R_1$ is hydrogen or $NH_2$. At present, $NH_2$ is marginally preferred over hydrogen.

The Group $R_2$

In the compounds in accordance with the invention, $R_2$ is selected from aryl and heteroaryl attached via a carbon atom, including substituted aryl and heteroaryl. For example, $R_2$ may be optionally substituted phenyl or an optionally substituted monocyclic or bicyclic heteroaryl group such as optionally substituted furyl, thienyl, thiazolyl, oxazolyl, imidazolyl, pyridyl, indolyl or benzofuranyl. At present optionally substituted phenyl, furyl (preferably 2-furyl) and thiazolyl (preferably 2-thiazolyl) are preferred. Optional substituents which may be present in $R_2$ include $C_1$-$C_3$ alkyl such as methyl and ethyl, $C_1$-$C_3$ alkoxy such as methoxy and ethoxy, cyano ($-CN$), chloro, bromo, fluoro, trifluoromethyl, and carboxamide groups such as $-CONR^AR^B$ where $R^A$ and $R^B$ are independently hydrogen or $C_1$-$C_3$ alkyl. Where optional substituents are present in monocyclic $R_2$, mono or disubstitution are presently preferred, although of the disubstitution options ortho-ortho disubstitution is less preferred at present. Examples of particular $R_2$ groups are 2-furyl, 5-methyl-2 furyl, 2-thiazolyl, 4-methyl-2-thiazolyl, phenyl, 3-cyanophenyl and o-methyl-phenyl.

The Group $R_3$

In the compounds in accordance with the invention, $R_3$ is H; optionally substituted $C_1$-$C_6$alkyl, $C_2$-$C_6$alkenyl, $C_2$-$C_6$alkynyl, or $C_3$-$C_7$ cycloalkyl, halogen; OH or $OR_{10}$ wherein $R_{10}$ is optionally substituted $C_1$-$C_6$alkyl such as ethyl, methyl, or n- or iso-propyl. Presently it is preferred that $R_3$ is H, $C_1$-$C_6$alkyl, halo substituted $C_1$-$C_6$alkyl, $C_3$-$C_6$ cycloalkyl, or halogen. Specific $R_3$ groups include H, methyl, ethyl, n- and isopropyl, cyclopropyl, n-sec and tert-butyl, trifluoromethyl, chloro, bromo and fluoro, and of the foregoing, hydrogen, methyl, chloro and bromo are presently preferred.

The Group $R_4$

In the compounds in accordance with the invention, $R_4$ is H, optionally substituted $C_1$-$C_6$alkyl, $C_3$-$C_6$alkenyl, $C_3$-$C_6$alkynyl, $C_3$-$C_7$ cycloalkyl, aryl or heteroaryl, or together with $R_5$ forms a 5 or 6-membered heterocyclic ring.

Where $R_4$ is heteroaryl or includes a heteroaryl ring (for example where $R_4$ is heteroaryl($C_1$-$C_6$alkyl)-), such rings include optionally substituted pyridyl, furanyl, thienyl, isoxazolyl, thiazolyl, pyrrolyl, imidazolyl, pyrazolyl, pyrazinyl, pyrimidinyl, benzimidazolyl, indolyl, benzthiazolyl, benzthiadiazolyl, quinolyl, and isoquinolyl. Of the foregoing, optionally substituted pyridyl (especially 2-pyridyl), imidazolyl, pyrazolyl, and isoxazolyl are most preferred at present.

Presently it is preferred that $R_4$ be $C_1$-$C_6$alkyl, substituted by aryl or heteroaryl, with the aryl or heteroaryl ring itself being optionally substituted. Within this category of $R_4$ groups are included arylmethyl and heteroarylmethyl, again with optional substitution in the aryl and heteroaryl rings. Phenyl is a preferred aryl ring, and heteroaryl rings in this category of $R_4$ groups include those listed in the preceding paragraph.

As indicated above, an aryl or heteroaryl group constituting or present in $R_4$ may be optionally substituted. Typically, only one substituent group is present. Optional substituents in this context include any of those referred to herein including $C_1$-$C_3$ alkyl such as methyl and ethyl, $C_1$-$C_3$ alkoxy such as methoxy and ethoxy, $C_1$-$C_3$ alkoxy($C_1$-$C_3$ alkyl)- such as $C_1$-$C_3$ alkoxymethyl including methoxymethyl, ethoxymethyl, n- and iso-propoxymethyl, and methoxy-($C_1$-$C_3$ alkyl)- such as methoxyethyl, a chloro, bromo, fluoro, trifluoromethyl, amino groups such as $-NR^AR^B$, carboxamide groups such as $-CONR^AR^B$ and reverse carboxamide groups such as $-NR^ACOR^B$ where $R^A$ and $R^B$ are independently hydrogen or $C_1$-$C_3$ alkyl or together form a 5 or 6-membered heterocyclic ring wherein said heterocyclic ring may be saturated, partially unsaturated or aromatic, and is preferably saturated, and wherein said heterocyclic ring may contain one or more additional heteroatom(s) preferably selected from N, O and S, and in one embodiment contains no further heteroatoms, and in one embodiment is unsubstituted.

The Group $R_5$

In the compounds in accordance with the invention, $R_5$ is H or optionally substituted $C_1$-$C_6$alkyl, $C_2$-$C_6$alkenyl, $C_2$-$C_6$alkynyl, or $C_3$-$C_7$ cycloalkyl, or together with $R_4$ forms a 5 or 6-membered heterocyclic ring. Presently it is preferred that $R_5$ is hydrogen.

The Groups $R_4$ and $R_5$ Together

In the compounds in accordance with the invention, $R_4$ and $R_5$ may be linked to form a 5 or 6-membered heterocyclic ring, said heterocyclic ring may be saturated, partially unsaturated or aromatic, and is preferably saturated. Said heterocyclic ring may contain one or more additional heteroatom(s) preferably selected from N, O and S. In one embodiment, the heterocyclic ring contains no further heteroatoms, and in another the ring contains further heteroatoms as, for example, in morpholino, thiomorpholino, piperazino and piperazinyl substituted with, for example, $C_1$-$C_3$ alkyl on the second ring nitrogen. In one embodiment, the heterocyclic ring is unsubstituted. In one embodiment, the 5 or 6-membered heterocyclic ring may be fused to an aromatic ring system, particularly a monocyclic ring system (preferably containing 6 ring atoms, such as phenyl) to form a multicyclic moiety, such as dihydroindolyl, dihydroisoindolyl, tetrahydroquinolinyl or tetrahydroisoquinolinyl.

Where chiral the compounds of formula (I) may be in the form of a racemic mixture of pairs of enantiomers or in enantiomerically pure form.

According to a further aspect of the present invention there is provided a method of treating or preventing a disorder in which the blocking of purine receptors, particularly adenosine receptors and more particularly adenosine $A_{2A}$ receptors, is beneficial, the method comprising administration to a subject in need of such treatment an effective dose of a compound of formula (I) as defined above, or a pharmaceutically acceptable salt or prodrug thereof.

The disorder with which the use or method of the invention is concerned may be caused by the hyperfunctioning of the purine receptors.

The use or method of the invention may be employed in respect of a human or animal subject, more preferably a mammal, more preferably a human subject.

The disorders of particular interest in connection with the use or method of the invention is concerned are those in which the blocking of purine receptors, particularly adenosine receptors and more particularly adenosine $A_{2A}$ receptors, may be beneficial. These may include movement disorders such as Parkinson's disease, drug-induced Parkinsonism, post-encephalitic Parkinsonism, Parkinsonism induced by poisoning (for example MPTP, manganese, carbon monoxide) and post-traumatic Parkinson's disease (punch-drunk syndrome).

Other movement disorders in which the blocking of purine receptors, may be of benefit include progressive supernuclear palsy, Huntingtons disease, multiple system atrophy, corticobasal degeneration, Wilsons disease, Hallerrorden-Spatz disease, progressive pallidal atrophy, Dopa-responsive dystonia-Parkinsonism, spasticity or other disorders of the basal ganglia which result in abnormal movement or posture. The present invention may also be effective in treating Parkinson's with on-off phenomena; Parkinson's with freezing (end of dose deterioration); and Parkinson's with prominent dyskinesias.

Thus, according to a further aspect of the present invention, there is provided use of a compound of formula (I) as defined above, or a pharmaceutically acceptable salt or prodrug thereof in the manufacture of a medicament for the treatment or prevention of movement disorders in a subject.

According to a further aspect of the invention there is provided a method of treating or preventing movement disorders comprising administration to a subject in need of such treatment an effective dose of a compound of formula (I) or a pharmaceutically acceptable salt or prodrug thereof.

The compounds of formula (I) may be used or administered in combination with one or more additional drugs useful in the treatment of movement disorders, such as L-DOPA or a dopamine agonist, the components being in the same formulation or in separate formulations for administration simultaneously or sequentially.

Other disorders in which the blocking of purine receptors, particularly adenosine receptors and more particularly adenosine $A_{2A}$ receptors may be beneficial include anxiety disorders, including panic disorder, agoraphobia, obsessive compulsive disorder, social phobia, post traumatic stress disorder, generalised anxiety disorder and specific phobia.

The use and method of treatment of the invention is also applicable in the case of non-inflammatory pain, particularly neuropathic pain, including trigeminal neuralgia, phantom limb pain, spinal cord injury pain, post-herpetic pain and HIV pain.

The use and method of the invention may also be useful in the case of affective disorders including mood disorders such as bipolar disorder, seasonal affective disorder, depression, manic depression, atypical depression and monodepressive disease; central and peripheral nervous system degenerative disorders including corticobasal degeneration, demyelinating disease (multiple sclerosis, disseminated sclerosis), Freidrich's ataxia, motoneurone disease (amyotrophic lateral sclerosis, progressive bulbar atrophy), multiple system atrophy, myelopathy, radiculopathy, peripheral neuropathy (diabetic neuropathy, tabes dorsalis, drug-induced neuropathy, vitamin deficiency), systemic lupus erythamatosis, granulomatous disease, olivo-ponto-cerebellar atrophy, progressive pallidal atrophy, progressive supranuclear palsy, spasticity; schizophrenia and related psychoses; cognitive and/or memory impairment disorders including dementia, Alzheimers Disease, Frontotemporal dementia, multi-infarct dementia, AIDS dementia, dementia associated with Huntingtons Disease, Lewy body dementia, senile dementia, age-related memory impairment, cognitive impairment associated with dementia, Korsakoff syndrome, dementia pugilans; attention disorders such as attention-deficit hyperactivity disorder (ADHD), attention deficit disorder, minimal brain dysfunction, brain-injured child syndrome, hyperkinetic reaction childhood, and hyperactive child syndrome; central nervous system injury including traumatic brain injury, neurosurgery (surgical trauma), neuroprotection for head injury, raised intracranial pressure, cerebral oedema, hydrocephalus, spinal cord injury; cerebral ischaemia including transient ischaemic attack, stroke (thrombotic stroke, ischaemic stroke, embolic stroke, haemorrhagic stroke, lacunar stroke) subarachnoid haemorrhage, cerebral vasospasm, neuroprotection for stroke, perinatal asphyxia, drowning, cardiac arrest, subdural haematoma; myocardial ischaemia; muscle ischaemia; sleep disorders such as hypersomnia, narcolepsy and restless legs syndrome; eye disorders such as retinal ischaemia-reperfusion injury and diabetic neuropathy; cardiovascular disorders such as claudication and hypotension; and diabetes and its complications.

According to a further aspect of the invention there is provided use of a compound of formula (I) or a pharmaceutically acceptable salt or prodrug thereof in the manufacture of a medicament for neuroprotection in a subject.

According to a further aspect of the invention there is provided a method of neuroprotection comprising administration to a subject in need of such treatment an effective dose of a compound of formula (I) or a pharmaceutically acceptable salt or prodrug thereof.

The medicament for or method of neuroprotection may be of use in the treatment of subjects who are suffering from or at risk from a neurodegenerative disorder, such as a movement disorder.

The present invention also includes novel compounds forming a subset of the compounds of formula (I) as defined above. Accordingly, the invention also provides compounds of formula (I) PROVIDED THAT:
(a) $R_2$ is not an optionally substituted pyrazolopyridine ring system;
(b) when $R_1$, and $R_3$ are hydrogen and $R_2$ is unsubstituted phenyl then —$NR_4R_5$ is not —$NH_2$, $NHCH_3$ or —$N(CH_3)_2$; and
(c) when $R_1$ is —$NH_2$ and $R_3$ is hydrogen, then $R_2$ is not phenyl or phenyl substituted by one or more substituents selected from halogen, hydroxy, $C_1$-$C_6$ alkyl, $C_1$-$C_6$ alkoxy, nitro, —$NH_2$, or —$NHCOCH_3$.

Subject to the exclusions imposed by provisos (a)-(c), preferred substituent groups $R_2$-$R_5$ in the novel compounds of the invention are as discussed above, including the preferred and specific classes and examples of those substituents. In the case where $R_1$ is —$NH_2$ and $R_3$ is hydrogen, and $R_2$ is substituted phenyl, the substituent(s) in the phenyl ring may be selected from, for example, methylenedioxy, $C_1$-$C_6$ alkylthio, trifluoromethyl, trifluoromethoxy, nitrile (—CN), oxo, $COR^A$, —$CONHR^A$, —$CONR^AR^B$, $NHR^A$, $NR^AR^B$, —NH-$COR^C$, —$NHCOOR^A$, —$NR^BCOOR^A$ wherein $R^A$ and $R^B$ are independently a $C_1$-$C_6$ alkyl group such as methyl, ethyl, n- or iso-propyl, and wherein $R^C$ is a $C_2$-$C_6$ alkyl group such as ethyl, or n- or iso-propyl.

There are multiple synthetic strategies for the synthesis of the compounds (I) with which the present invention is concerned, but all rely on known chemistry, known to the synthetic organic chemist. Thus, compounds according to formula (I) can be synthesised according to procedures described in the standard literature and are well-known to the one skilled in the art. Typical literature sources are "*Advanced organic chemistry*", $4^{th}$ Edition (Wiley), J March, "*Comprehensive Organic Transformation*", $2^{nd}$ Edition (Wiley), R. C. Larock, "*Handbook of Heterocyclic Chemistry*", $2^{nd}$ Edition (Pergamon), A. R. Katritzky), review articles such as found in "*Synthesis*", "*Acc. Chem. Res.*", "*Chem. Rev*", or primary literature sources identified by standard literature searches online or from secondary sources such as "*Chemical Abstracts*" or "*Beilstein*". Suitable reaction schemes are as follows

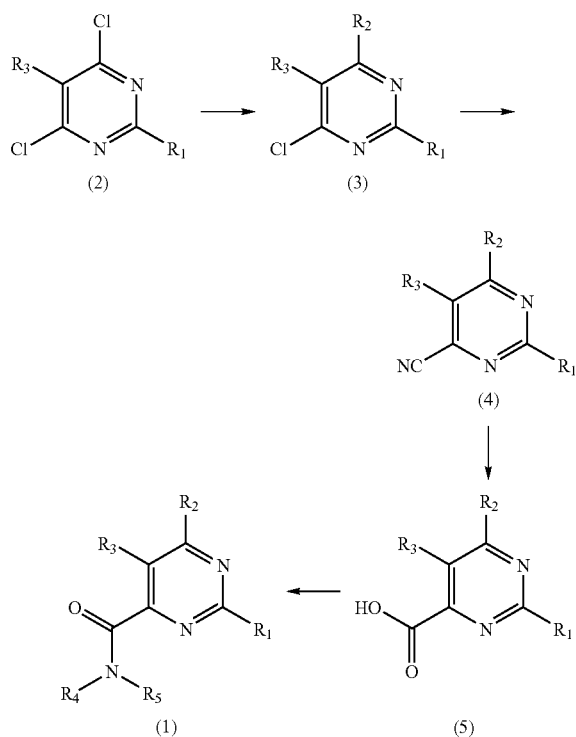

Compounds of formula (1) may be prepared from compounds of formula (5) by standard methods used for coupling carboxylic acids and amines. Such coupling reactions would include reaction of a carboxylic acid derivative such as an imidazolide prepared with N,N'-carbonyldiimidazole or a mixed anhydride prepared with an alkyl chloroformate and a trialkylamine base or an acyl chloride prepared from a chlorinating source such as oxalyl chloride with an appropriate amine, or by direct coupling of an appropriate amine in the presence of a standard coupling reagent such as dicyclohexylcarbodiimide and a nucleophilic catalyst such as 4-dimethylaminopyridine.

Compounds of formula (5) may be prepared from compounds of formula (4) by standard methods such as hydrolysis with a mineral acid such as sulfuric or hydrochloric acid.

Compounds of formula (4) may be prepared from compounds of formula (3) by standard methods such as cyanation with an alkali metal cyamide such as sodium cyamide or an organic source of cyamide such as tetraethylammonium cyamide in the presence of a tertiary amine base such as 1,4-diazabicyclo[2.2.2]octane or triethylamine.

Compounds of formula (3) are either known in the literature or may be prepared from the known compound of formula (2) by standard methods such as aryl or heteroaryl coupling reactions. Such aryl or heteroaryl coupling reactions would include reaction with an appropriate aryl or heteroarylboronic acid derivative, an aryl or heteroaryltrialkylstannane derivative or an aryl or heteroarylzinc halide derivative in the presence of a suitable catalyst such as a palladium complex.

In Reaction Scheme (1) compounds of formula (1), where $R_3$ is halogen, may be prepared from compounds of formula (1), where $R_3$ is H, by standard methods such as halogenation with N-bromo- or N-chlorosuccinimide.

Compounds of formula (5), where $R_3$ is H, may alternatively be synthesised by standard methods such as those illustrated in Reaction Scheme 2.

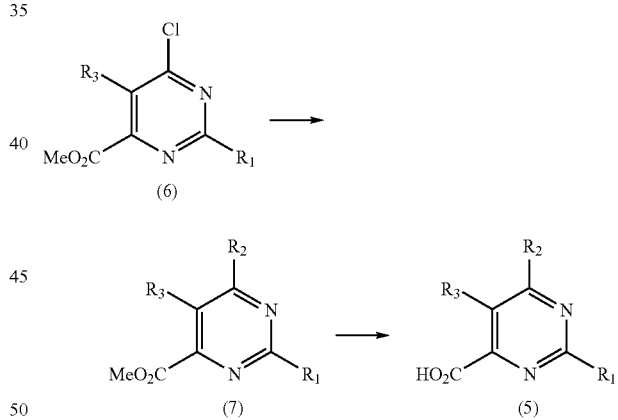

In Reaction Scheme (2) compounds of formula (5), where $R_3$ is H, may be prepared from compounds of formula (7), where $R_3$ is H, by standard methods such as hydrolysis with aqueous alkali such as lithium, sodium or potassium hydroxide.

Compounds of formula (7), where $R_3$ is H, may be prepared from compounds of formula (6), where $R_3$ is H, by standard methods such as aryl or heteroaryl coupling reactions as described above.

Compounds of formula (6), where $R_3$ is H, are known in the literature.

Compounds of formula (3), where $R_3$ is H or alkyl, may alternatively be synthesised by standard methods such as those illustrated in Reaction Scheme 3.

Reaction Scheme 3

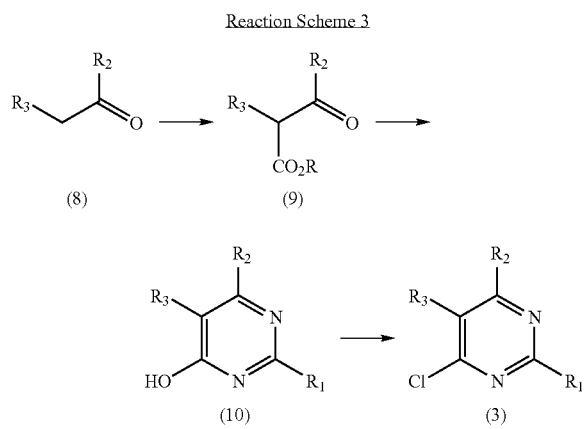

Compounds of formula (3), where $R_3$ is H or alkyl, may be prepared from compounds of formula (10), where $R_3$ is H or alkyl, by standard methods such as chlorination with $POCl_3$.

Compounds of formula (10), where $R_3$ is H or alkyl, may be prepared from compounds of formula (9), where $R_3$ is H or alkyl, by standard methods such as condensation with guanidine or formamidine Compounds of formula (9), where $R_3$ is H or alkyl, are known in the literature or may be prepared from compounds of formula (8), where $R_3$ is H or alkyl, by standard methods such as deprotonation with a base such as NaH followed by treatment with a carboxylating reagent such as diethyl carbonate.

Compounds of formula (8), where $R_3$ is H or alkyl, are either known in the literature or may be prepared by standard methods Compounds of formula (5), where $R_3$ is H or alkyl, may alternatively be synthesised by standard methods such as those illustrated in Reaction Scheme 4.

Reaction Scheme 4

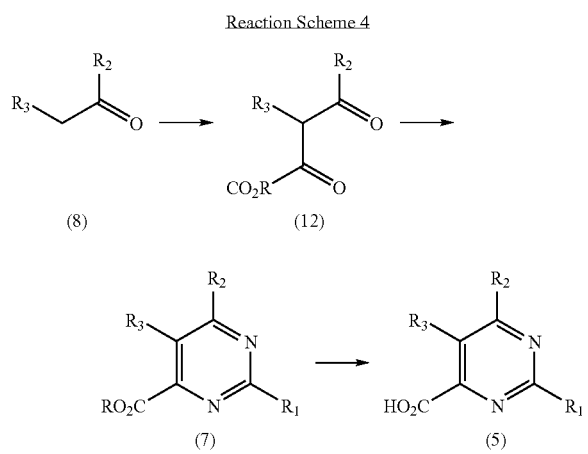

Compounds of formula (5), where $R_3$ is H or alkyl, may be synthesised from compounds of formula (7) as described above.

Compounds of formula (7), where $R_3$ is H or alkyl, may be prepared from compounds of formula (12), where $R_3$ is H or alkyl, by standard methods such as condensation with guanidine or formamidine.

Compounds of formula (12), where $R_3$ is H or alkyl, may be prepared from compounds of formula (8), where $R_3$ is H or alkyl, by standard methods such as deprotonation with a base such as NaH followed by treatment with a reagent such as diethyl oxalate.

Compounds with which the invention is concerned may be presented in a pharmaceutical composition comprising a compound of formula (I) as defined and discussed above in combination with a pharmaceutically acceptable carrier or excipient.

Any suitable route of administration may be employed for providing the patient with an effective dosage of a compound of formula (I). For example, oral, rectal, parenteral (intravenous, intramuscular), transdermal, subcutaneous, and the like may be employed. Dosage forms include tablets, troches, dispersions, suspensions, solutions, capsules, patches, and the like. The most suitable route in any given case will depend on the severity of the condition being treated. The most preferred route of administration of the present invention is the oral route. The compositions may be conveniently presented in unit dosage form and prepared by any of the methods well known in the art of pharmacy.

In practical use, the compounds of formula (I) can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (e.g. intravenous). In preparing the compositions for oral dosage form, any of the usual pharmaceutical media may be employed as carriers, such as, for example, water, glycols, oils, alcohols, flavouring agents, preservatives, colouring agents, and the like in the case of oral liquid preparations (such as suspensions, solutions and elixirs) or aerosols; or carriers such as starches, sugars, micro-crystalline cellulose, diluents, granulating agents, lubricants, binders, disintegrating agents, and the like may be used in the case of oral solid preparations such as, for example, powders, capsules, and tablets, with the solid oral preparations being preferred over the liquid preparations. The most preferred solid oral preparation is tablets.

Because of their ease of administration, tablets and capsules represent the most advantageous oral dosage unit form in which case solid pharmaceutical carriers are employed. If desired, tablets may be coated by standard aqueous or non-aqueous techniques.

In addition to the common dosage forms set out above, the compounds of formula (I) may also be administered by controlled release means and/or delivery devices such as those described in U.S. Pat. Nos. 3,845,770; 3,916,899; 3,536,809; 3,598,123; 3,630,200; 4,008,719; 4,687,660; and 4,769,027, the disclosures of which are hereby incorporated by reference.

Pharmaceutical compositions employed in the present invention suitable for oral administration may be presented as discrete units such as capsules, cachets, or tablets, or aerosol sprays each containing a predetermined amount of the active ingredient as a powder or granules, a solution or a suspension in an aqueous liquid, an oil-in-water emulsion, or a water-in-oil liquid emulsion. Such compositions may be prepared by any of the methods of pharmacy, but all methods include the step of bringing the active ingredient into association with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or moulding, optionally with one or more accessory ingredients. Compressed tablets may be prepared by compressing in a suitable machine the active ingredient in a free-flowing form such as powder or granules, optionally mixed with a binder, a lubricant, an inert diluent, and/or a surface active or dispersing agent. Moulded tablets may be made by moulding in a suitable machine a mixture of the powdered compound moistened with an inert liquid diluent.

The invention is further defined by reference to the following examples. It will be apparent to those skilled in the art that many modifications, both to materials and methods, may be practiced without departing from the purpose and interest of this invention.

EXAMPLES

Synthetic Examples

The invention is illustrated with reference to the following Examples, as set out in Table 1.

TABLE 1

| Example | Structure | Compound Name |
| --- | --- | --- |
| 1 | 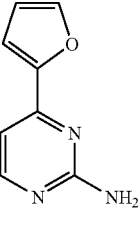 | 2-Amino-N-(2-fluorobenzyl)-6-(2-furyl)pyrimidine-4-carboxamide |
| 2 | 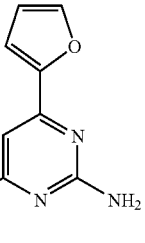 | 2-Amino-N-(3,4-difluorophenyl)-6-(2-furyl)pyrimidine-4-carboxamide |
| 3 | 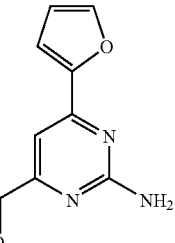 | 2-Amino-6-(2-furyl)-N-(3-methoxybenzyl)pyrimidine-4-carboxamide |
| 4 | 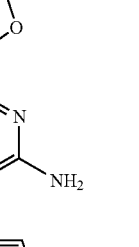 | 2-Amino-6-(2-furyl)-N,N-dimethylpyrimidine-4-carboxamide |
| 5 | 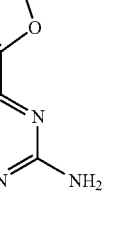 | 1-(2-Amino-6-(2-furyl)pyrimidin-4-ylcarbonyl)piperidine |

TABLE 1-continued

| Example | Structure | Compound Name |
|---|---|---|
| 6 | 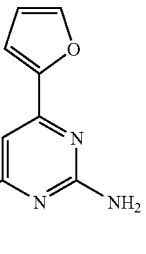 | 2-Amino-6-(2-furyl)-N-(2-methoxybenzyl)pyrimidine-4-carboxamide |
| 7 | 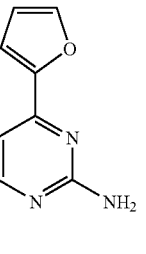 | 2-Amino-6-(2-furyl)-N-(2-furylmethyl)pyrimidine-4-carboxamide |
| 8 | 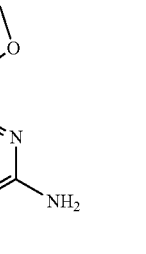 | 2-Amino-6-(2-furyl)pyrimidine-4-carboxamide |
| 9 | 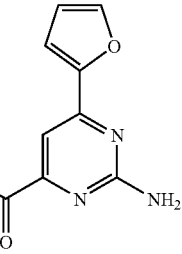 | 2-Amino-6-(2-furyl)-N-(4-dimethylaminobenzyl)pyrimidine-4-carboxamide |
| 10 | 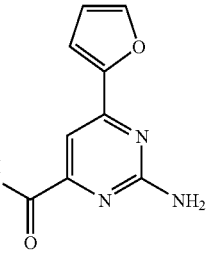 | 2-Amino-6-(2-furyl)-N-(6-methoxymethylpyridin-2-ylmethyl)pyrimidine-4-carboxamide |
| 11 | 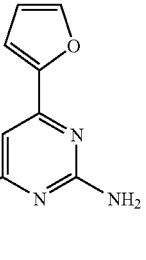 | 2-Amino-6-(2-furyl)-N-(3-methylpyridin-2-ylmethyl)pyrimidine-4-carboxamide |

TABLE 1-continued

| Example | Structure | Compound Name |
|---|---|---|
| 12 | 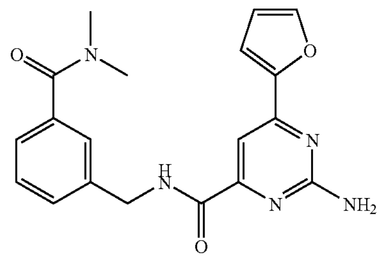 | 2-Amino-6-(2-furyl)-N-(3-(dimethylaminocarbonyl)benzyl)pyrimidine-4-carboxamide |
| 13 | 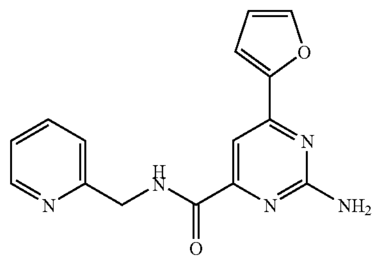 | 2-Amino-6-(2-furyl)-N-(2-pyridylmethyl)pyrimidine-4-carboxamide |
| 14 | 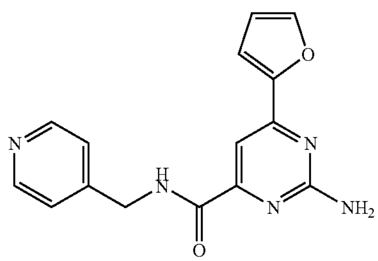 | 2-Amino-6-(2-furyl)-N-(4-pyridylmethyl)pyrimidine-4-carboxamide |
| 15 | 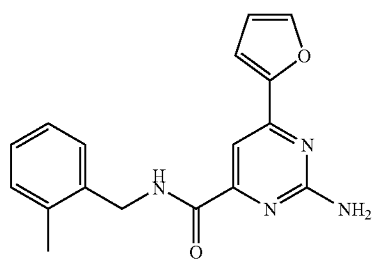 | 2-Amino-6-(2-furyl)-N-(2-methylbenzyl)pyrimidine-4-carboxamide |
| 16 | 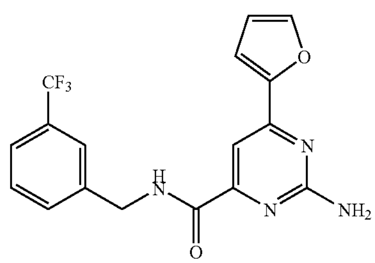 | 2-Amino-N-(3-trifluoromethylbenzyl)-6-(2-furyl)pyrimidine-4-carboxamide |
| 17 | 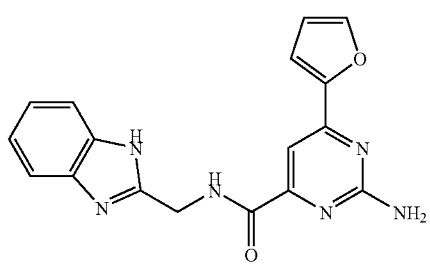 | 2-Amino-N-(1H-benzimidazol-2-ylmethyl)-6-(2-furyl)pyrimidine-4-carboxamide |

TABLE 1-continued

| Example | Structure | Compound Name |
|---|---|---|
| 18 | 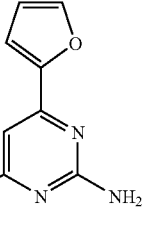 | 2-Amino-6-(2-furyl)-N-(3-pyridylmethyl)pyrimidine-4-carboxamide |
| 19 | 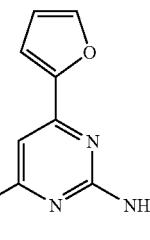 | 2-Amino-6-(2-furyl)-N-(3-methylbenzyl)pyrimidine-4-carboxamide |
| 20 | 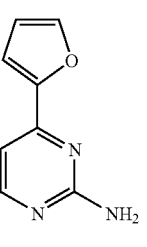 | 2-Amino-6-(2-furyl)-N-(3-methoxymethylpyridin-2-ylmethyl)pyrimidine-4-carboxamide |
| 21 | 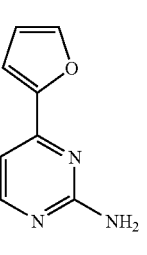 | 2-Amino-6-(2-furyl)-N-(3-dimethylaminomethylpyridin-2-ylmethyl)pyrimidine-4-carboxamide |
| 22 | 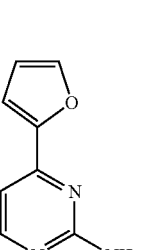 | 2-Amino-6-(2-furyl)-N-(3-(4-morpholinylmethyl)pyridin-2-ylmethyl)pyrimidine-4-carboxamide |
| 23 | 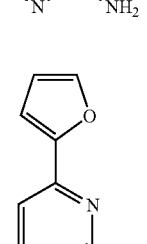 | 2-Amino-6-(2-furyl)-N-(3,6-dimethylpyridin-2-ylmethyl)pyrimidine-4-carboxamide |

TABLE 1-continued

| Example | Structure | Compound Name |
| --- | --- | --- |
| 24 | 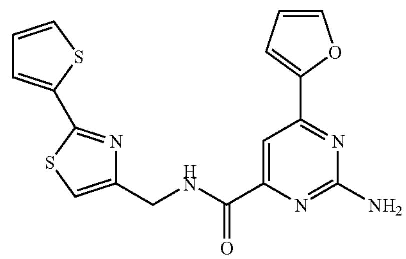 | 2-Amino-6-(2-furyl)-N-(2-(2-thienyl)thiazol-4-ylmethyl)pyrimidine-4-carboxamide |
| 25 | 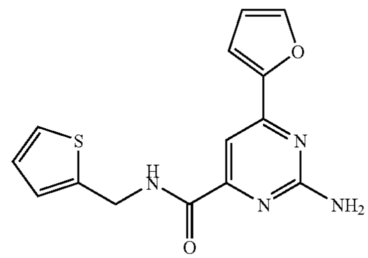 | 2-Amino-6-(2-furyl)-N-(2-thienylmethyl)pyrimidine-4-carboxamide |
| 26 | 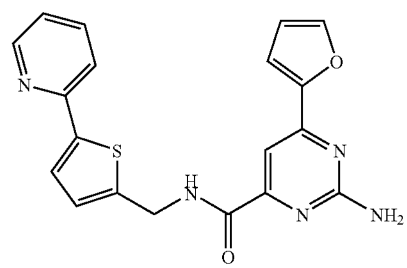 | 2-Amino-6-(2-furyl)-N-(5-(2-pyridyl)-2-thienylmethyl)pyrimidine-4-carboxamide |
| 27 | 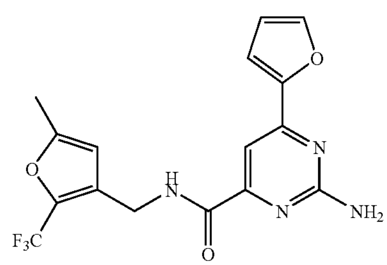 | 2-Amino-6-(2-furyl)-N-(5-methyl-2-trifluoromethylfuran-3-ylmethyl)pyrimidine-4-carboxamide |
| 28 | 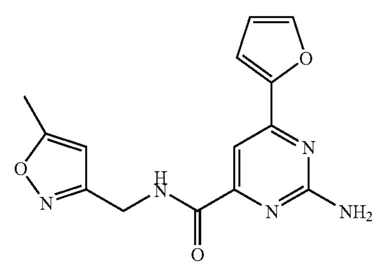 | 2-Amino-6-(2-furyl)-N-(5-methylisoxazol-3-ylmethyl)pyrimidine-4-carboxamide |
| 29 | 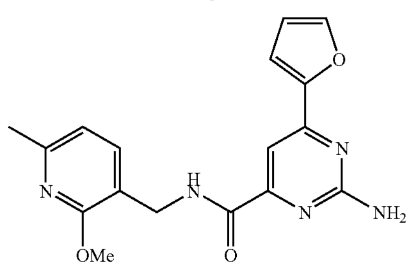 | 2-Amino-6-(2-furyl)-N-(2-methoxy-6-methylpyridin-3-ylmethyl)pyrimidine-4-carboxamide |

TABLE 1-continued

| Example | Structure | Compound Name |
|---|---|---|
| 30 | 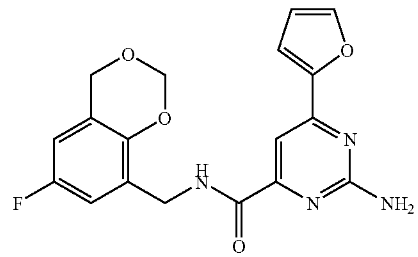 | 2-Amino-N-(6-fluoro[1,3]benzodioxin-8-ylmethyl)-6-(2-furyl)pyrimidine-4-carboxamide |
| 31 | 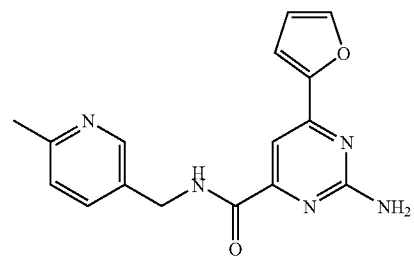 | 2-Amino-6-(2-furyl)-N-(6-methylpyridin-3-ylmethyl)pyrimidine-4-carboxamide |
| 32 | 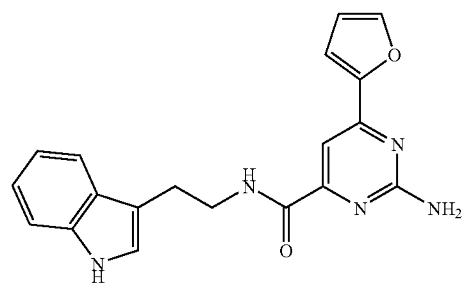 | 2-Amino-6-(2-furyl)-N-(3-indolylmethyl)pyrimidine-4-carboxamide |
| 33 | 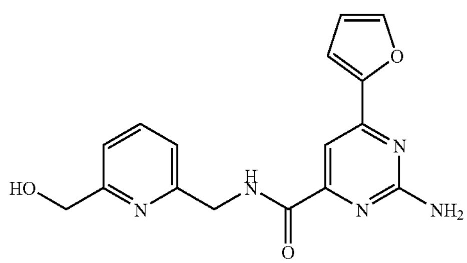 | 2-Amino-6-(2-furyl)-N-(6-hydroxymethylpyridin-2-ylmethyl)pyrimidine-4-carboxamide |
| 34 | 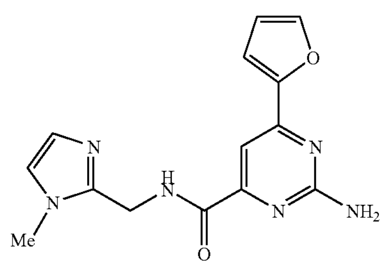 | 2-Amino-6-(2-furyl)-N-(1-methyl-1H-imidazol-2-ylmethyl)pyrimidine-4-carboxamide |
| 35 | 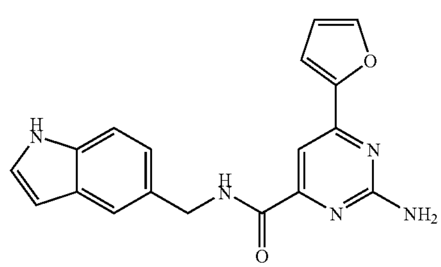 | 2-Amino-6-(2-furyl)-N-(5-indolylmethyl)pyrimidine-4-carboxamide |

TABLE 1-continued

| Example | Structure | Compound Name |
|---|---|---|
| 36 | 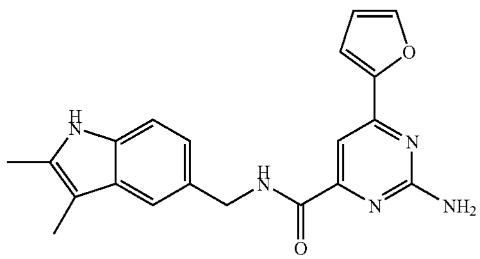 | 2-Amino-N-(2,3-dimethylindol-5-ylmethyl)-6-(2-furyl)pyrimidine-4-carboxamide |
| 37 | 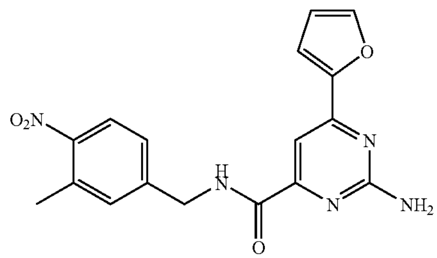 | 2-Amino-6-(2-furyl)-N-(3-methyl-4-nitrobenzyl)pyrimidine-4-carboxamide |
| 38 | 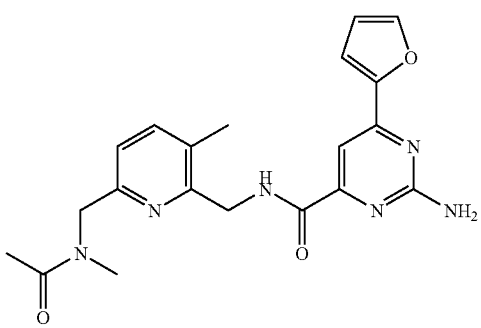 | N-(6-(N-Acetyl-N-methylaminomethyl)-3-methylpyridin-2-ylmethyl)-2-amino-6-(2-furyl)pyrimidine-4-carboxamide |
| 39 | 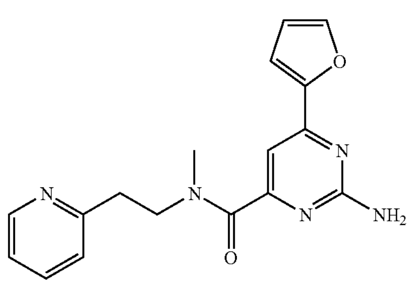 | 2-Amino-6-(2-furyl)-N-methyl-N-(2-(2-pyridyl)ethyl)pyrimidine-4-carboxamide |
| 40 | 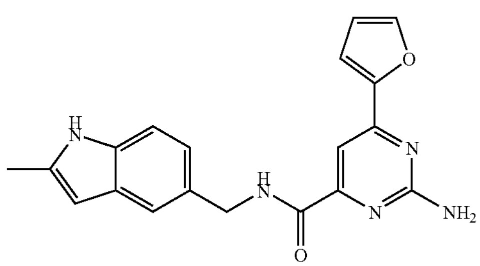 | 2-Amino-6-(2-furyl)-N-(2-methylindol-5-ylmethyl)pyrimidine-4-carboxamide |

TABLE 1-continued

| Example | Structure | Compound Name |
|---|---|---|
| 41 | 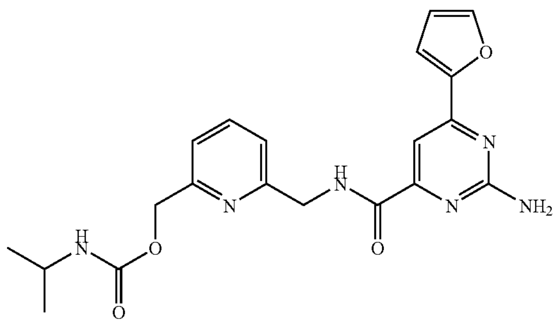 | 6-(2-Amino-6-(2-furyl)pyrimidine-4-carboxamidomethyl)pyridin-2-ylmethyl isopropylcarbamate |
| 42 | 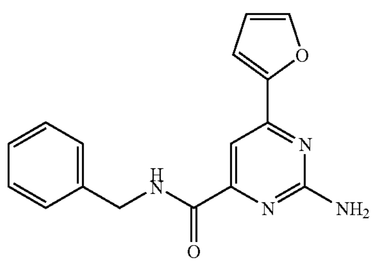 | 2-Amino-N-benzyl-6-(2-furyl)pyrimidine-4-carboxamide |
| 43 | 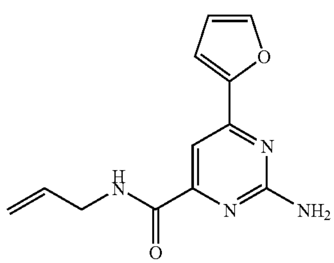 | N-Allyl-2-amino-6-(2-furyl)pyrimidine-4-carboxamide |
| 44 | 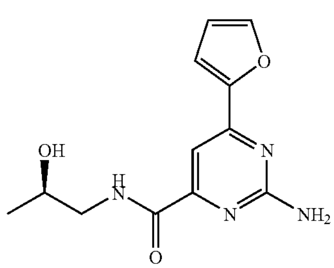 | (R)-2-Amino-6-(2-furyl)-N-(2-hydroxypropyl)pyrimidine-4-carboxamide |
| 45 | 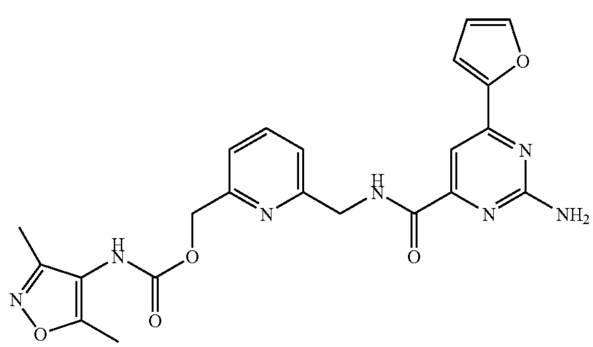 | 6-(2-Amino-6-(2-furyl)pyrimidine-4-carboxamidomethyl)pyridin-2-ylmethyl 3,5-dimethyloxazol-4-ylcarbamate |

TABLE 1-continued

| Example | Structure | Compound Name |
|---|---|---|
| 46 | 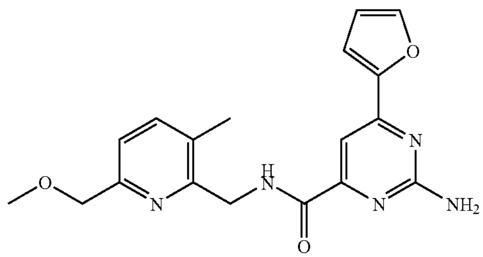 | 2-Amino-6-(2-furyl)-N-(6-methoxymethyl-3-methylpyridin-2-ylmethyl)pyrimidine-4-carboxamide |
| 47 | 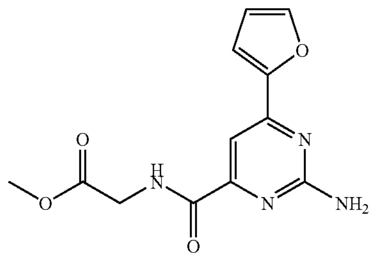 | Methyl 2-amino-6-(2-furyl)pyrimidine-4-carboxamidoacetate |
| 48 | 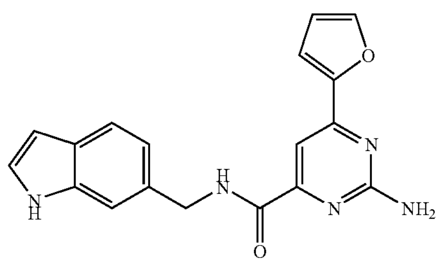 | 2-Amino-6-(2-furyl)-N-(6-indolylmethyl)pyrimidine-4-carboxamide |
| 49 | 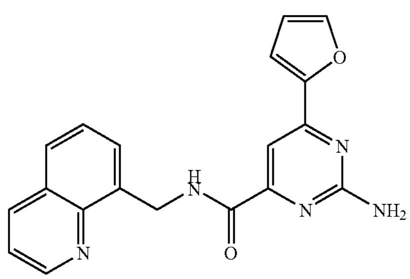 | 2-Amino-6-(2-furyl)-N-(quinolin-8-ylmethyl)pyrimidine-4-carboxamide |
| 50 | 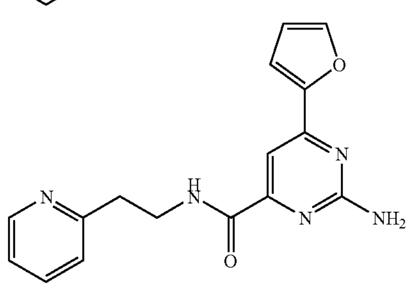 | 2-Amino-6-(2-furyl)-N-(2-(pyridin-2-yl)ethyl)pyrimidine-4-carboxamide |
| 51 | 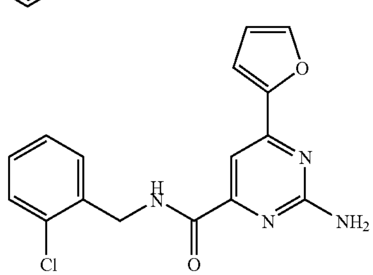 | 2-Amino-N-(2-chlorobenzyl)-6-(2-furyl)pyrimidine-4-carboxamide |

TABLE 1-continued

| Example | Structure | Compound Name |
|---|---|---|
| 52 | 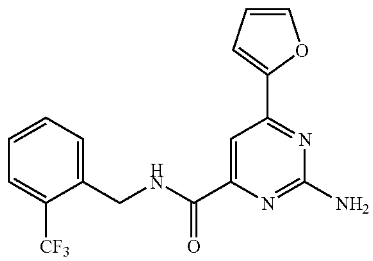 | 2-Amino-6-(2-furyl)-N-(2-trifluoromethylbenzyl)pyrimidine-4-carboxamide |
| 53 | 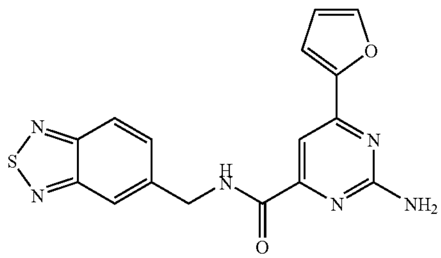 | 2-Amino-N-([2,1,3]benzothiadiazol-5-ylmethyl)-6-(2-furyl)pyrimidine-4-carboxamide |
| 54 | 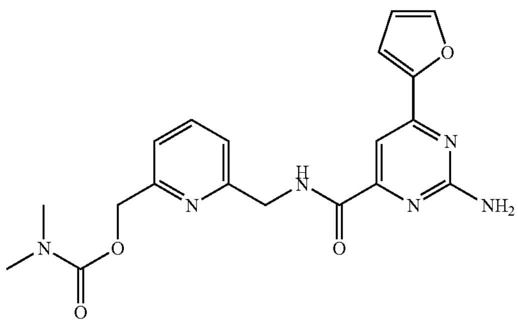 | 6-(2-Amino-6-(2-furyl)pyrimidine-4-carboxamidomethyl)pyridin-2-ylmethyl dimethylcarbamate |
| 55 | 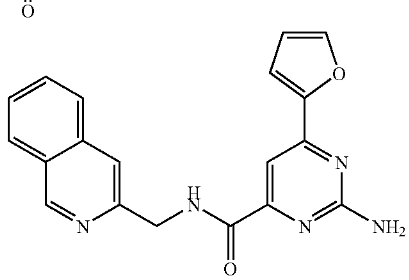 | 2-Amino-6-(2-furyl)-N-(isoquinolin-3-ylmethyl)pyrimidine-4-carboxamide |
| 56 | 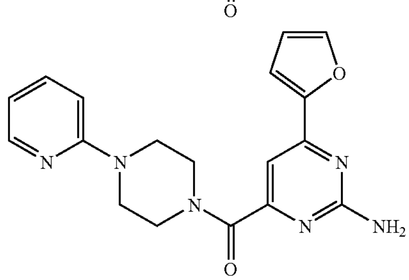 | 1-(2-Amino-6-(2-furyl)pyrimidin-4-ylcarbonyl)-4-(2-pyridyl)piperazine |
| 57 | 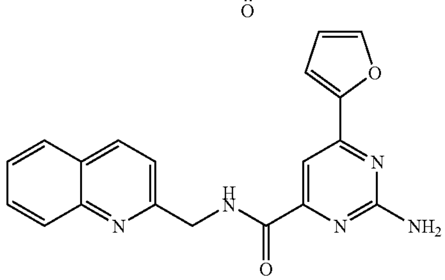 | 2-Amino-6-(2-furyl)-N-(quinolin-2-ylmethyl)pyrimidine-4-carboxamide |

TABLE 1-continued

| Example | Structure | Compound Name |
|---|---|---|
| 58 | 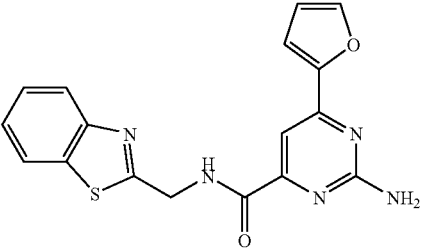 | 2-Amino-N-(benzothiazol-2-ylmethyl)-6-(2-furyl)pyrimidine-4-carboxamide |
| 59 | 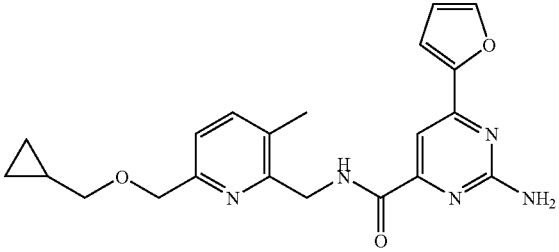 | 2-Amino-N-(6-cyclopropylmethoxymethyl-3-methylpyridin-2-ylmethyl)-6-(2-furyl)pyrimidine-4-carboxamide |
| 60 | 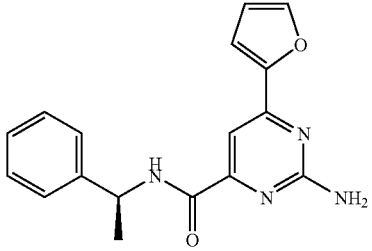 | (S)-2-Amino-6-(2-furyl)-N-(1-phenylethyl)pyrimidine-4-carboxamide |
| 61 | 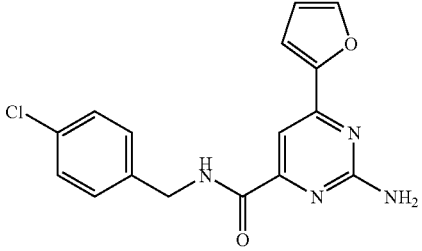 | 2-Amino-N-(4-chlorobenzyl)-6-(2-furyl)pyrimidine-4-carboxamide |
| 62 | 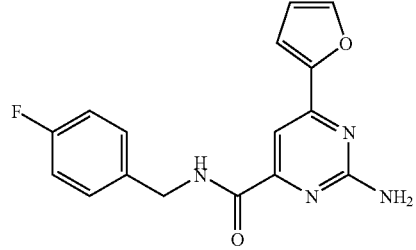 | 2-Amino-N-(4-fluorobenzyl)-6-(2-furyl)pyrimidine-4-carboxamide |
| 63 | 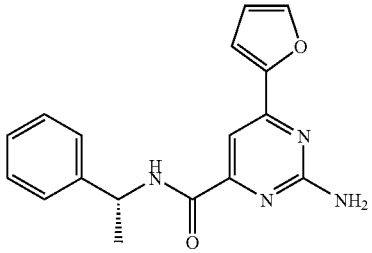 | (R)-2-Amino-6-(2-furyl)-N-(1-phenylethyl)pyrimidine-4-carboxamide |

TABLE 1-continued

| Example | Structure | Compound Name |
|---|---|---|
| 64 | 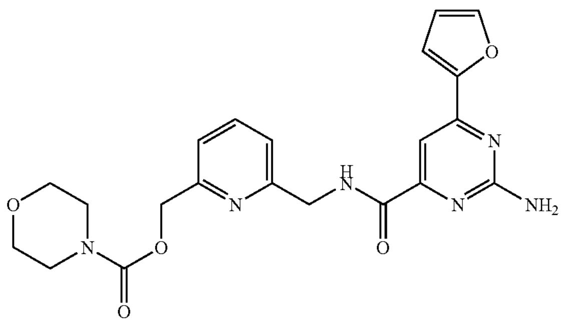 | 6-(2-Amino-6-(2-furyl)pyrimidine-4-carboxamidomethyl)pyridin-2-ylmethyl morpholine-1-carboxylate |
| 65 | 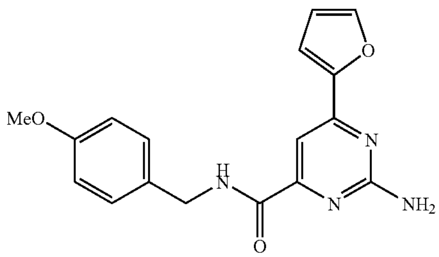 | 2-Amino-6-(2-furyl)-N-(4-methoxybenzyl)pyrimidine-4-carboxamide |
| 66 | 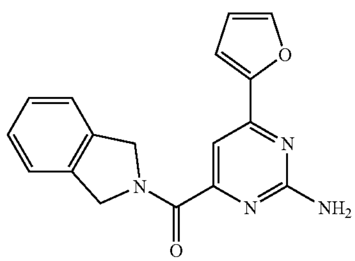 | 2-(2-Amino-6-(2-furyl)pyrimidin-4-ylcarbonyl)-2,3-dihydro-1H-isoindole |
| 67 | 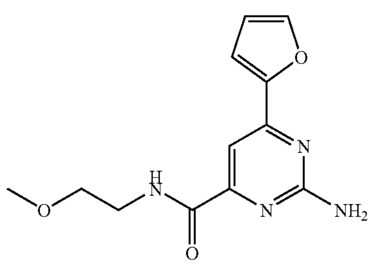 | 2-Amino-6-(2-furyl)-N-(2-methoxyethyl)pyrimidine-4-carboxamide |
| 68 | 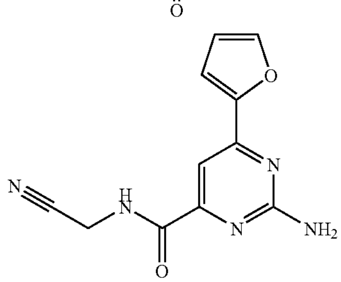 | 2-Amino-N-(cyanomethyl)-6-(2-furyl)pyrimidine-4-carboxamide |
| 69 | 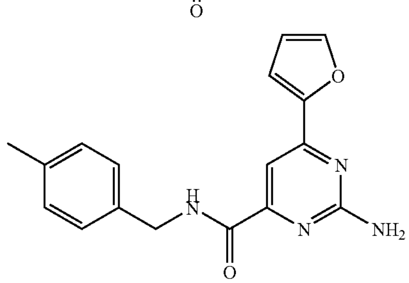 | 2-Amino-6-(2-furyl)-N-(4-methylbenzyl)pyrimidine-4-carboxamide |

TABLE 1-continued

| Example | Structure | Compound Name |
|---|---|---|
| 70 | 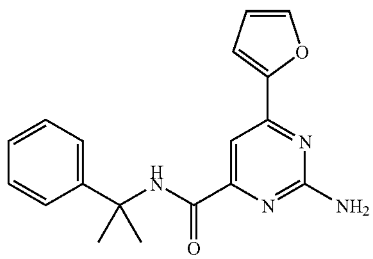 | 2-Amino-6-(2-furyl)-N-(1-phenylprop-1-yl)pyrimidine-4-carboxamide |
| 71 | 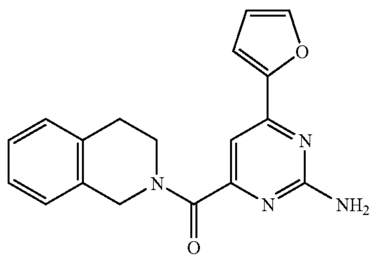 | 2-(2-Amino-6-(2-furyl)pyrimidin-4-ylcarbonyl)-1,2,3,4-tetrahydroisoquinoline |
| 72 | 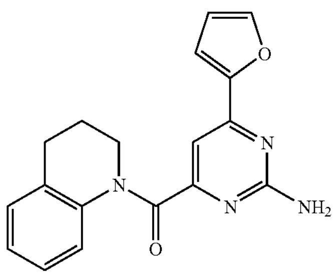 | 1-(2-Amino-6-(2-furyl)pyrimidin-4-ylcarbonyl)-1,2,3,4-tetrahydroquinoline |
| 73 | 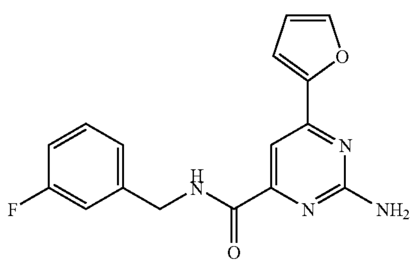 | 2-Amino-N-(3-fluorobenzyl)-6-(2-furyl)pyrimidine-4-carboxamide |
| 74 | 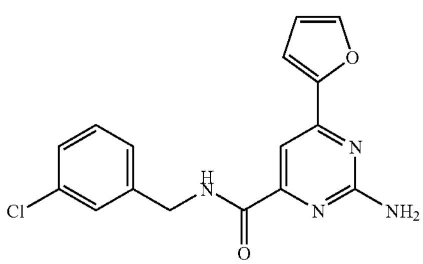 | 2-Amino-N-(3-chlorobenzyl)-6-(2-furyl)pyrimidine-4-carboxamide |
| 75 | 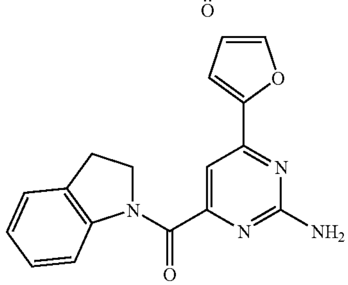 | 1-(2-Amino-6-(2-furyl)pyrimidin-4-ylcarbonyl)-2,3-dihydroindole |

TABLE 1-continued
| Example | Structure | Compound Name |
|---|---|---|
| 76 | 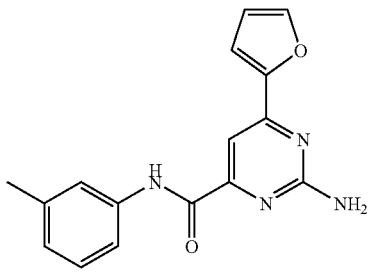 | 2-Amino-6-(2-furyl)-N-(3-methylphenyl)pyrimidine-4-carboxamide |
| 77 | 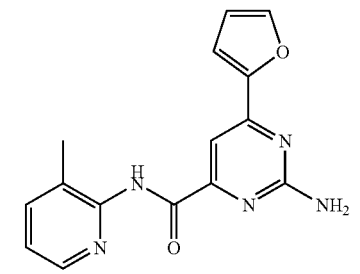 | 2-Amino-6-(2-furyl)-N-(3-methylpyridin-2-yl)pyrimidine-4-carboxamide |
| 78 | 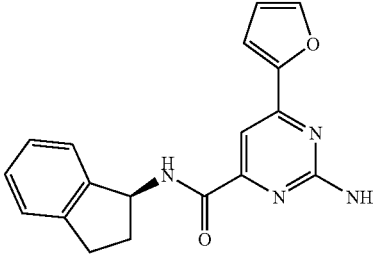 | (R)-2-Amino-6-(2-furyl)-N-(1-indanyl)pyrimidine-4-carboxamide |
| 79 | 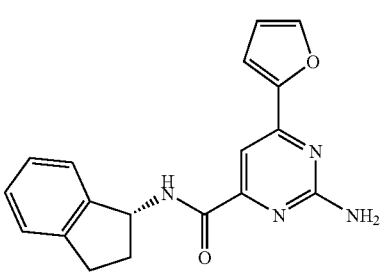 | (S)-2-Amino-6-(2-furyl)-N-(1-indanyl)pyrimidine-4-carboxamide |
| 80 | 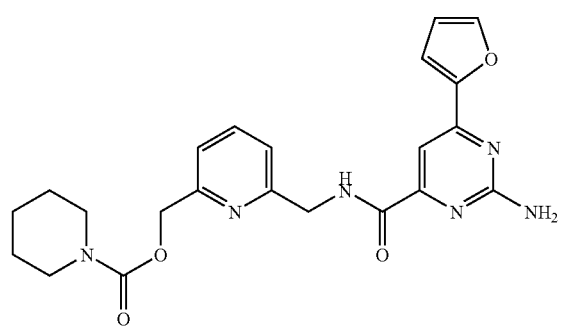 | 6-(2-Amino-6-(2-furyl)pyrimidine-4-carboxamidomethyl)pyridin-2-ylmethyl piperidine-1-carboxylate |

TABLE 1-continued

| Example | Structure | Compound Name |
| --- | --- | --- |
| 81 | 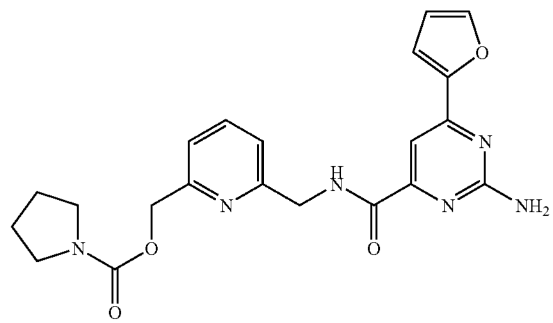 | 6-(2-Amino-6-(2-furyl)pyrimidine-4-carboxamidomethyl)pyridin-2-ylmethyl pyrrolidine-1-carboxylate |
| 82 | 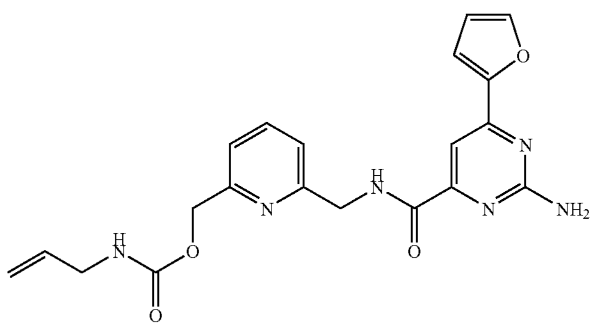 | 6-(2-Amino-6-(2-furyl)pyrimidine-4-carboxamidomethyl)pyridin-2-ylmethyl allylcarbamate |
| 83 | 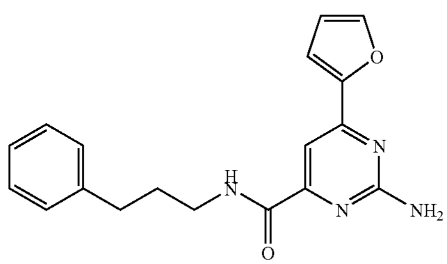 | 2-Amino-6-(2-furyl)-N-(3-phenylpropyl)pyrimidine-4-carboxamide |
| 84 | 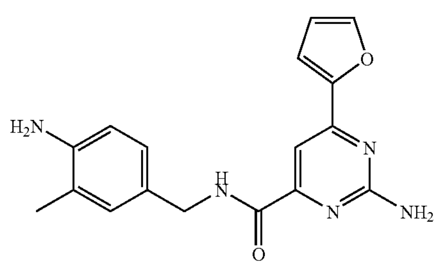 | 2-Amino-N-(4-amino-3-methylbenzyl)-6-(2-furyl)pyrimidine-4-carboxamide |
| 85 | 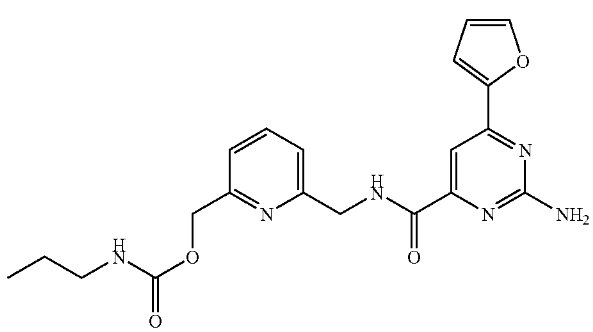 | 6-(2-Amino-6-(2-furyl)pyrimidine-4-carboxamidomethyl)pyridin-2-ylmethyl n-propylcarbamate |

TABLE 1-continued

| Example | Structure | Compound Name |
|---|---|---|
| 86 | 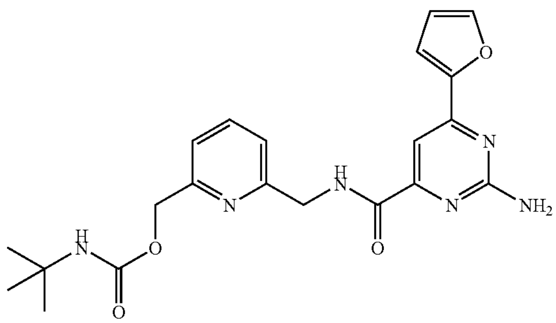 | 6-(2-Amino-6-(2-furyl)pyrimidine-4-carboxamidomethyl)pyridin-2-ylmethyl tert-butylcarbamate |
| 87 | 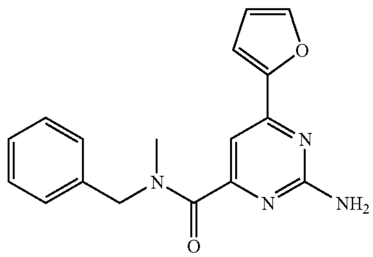 | 2-Amino-N-benzyl-6-(2-furyl)-N-methylpyrimidine-4-carboxamide |
| 88 | 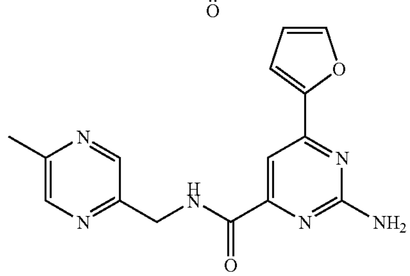 | 2-Amino-6-(2-furyl)-N-(5-methylpyrazin-2-ylmethyl)pyrimidine-4-carboxamide |
| 89 | 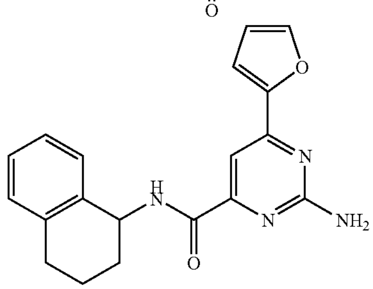 | (R,S)-2-Amino-6-(2-furyl)-N-(1,2,3,4-tetrahydro-1-naphthyl)pyrimidine-4-carboxamide |
| 90 | 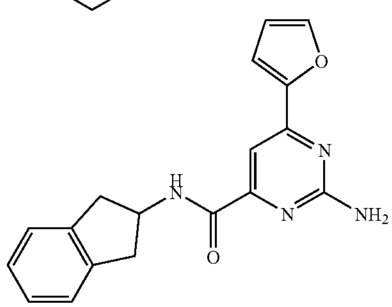 | 2-Amino-6-(2-furyl)-N-(2-indanyl)pyrimidine-4-carboxamide |
| 91 | 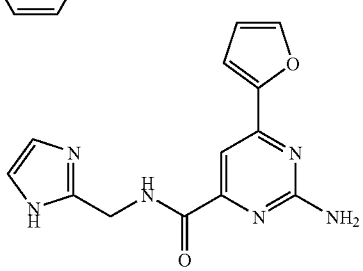 | 2-Amino-6-(2-furyl)-N-(1H-imidazol-2-ylmethyl)pyrimidine-4-carboxamide |

TABLE 1-continued

| Example | Structure | Compound Name |
|---|---|---|
| 92 | 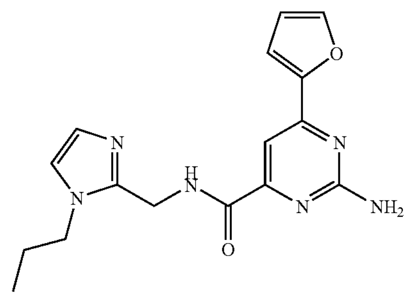 | 2-Amino-6-(2-furyl)-N-(1-n-propyl-1H-imidazol-2-ylmethyl)pyrimidine-4-carboxamide |
| 93 | 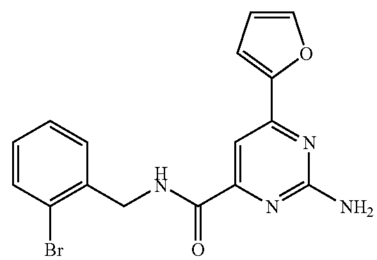 | 2-Amino-N-(2-bromobenzyl)-6-(2-furyl)pyrimidine-4-carboxamide |
| 94 | 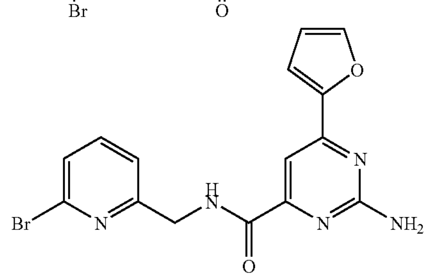 | 2-Amino-N-(6-bromopyridin-2-ylmethyl)-6-(2-furyl)pyrimidine-4-carboxamide |
| 95 | 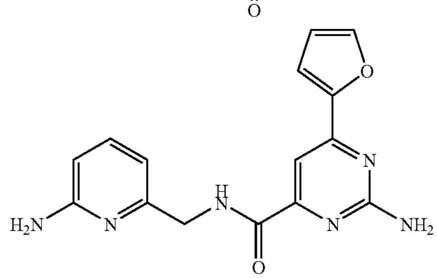 | 2-Amino-N-(6-aminopyridin-2-ylmethyl)-6-(2-furyl)pyrimidine-4-carboxamide |
| 96 | 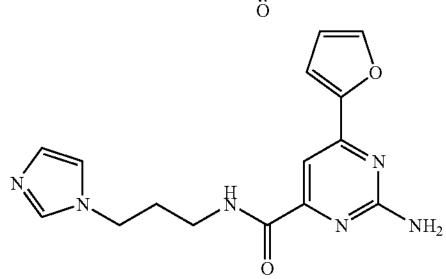 | 2-Amino-6-(2-furyl)-N-(3-(1H-imidazol-1-yl)propyl)pyrimidine-4-carboxamide |
| 97 | 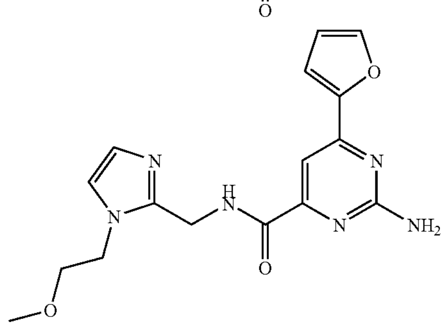 | 2-Amino-6-(2-furyl)-N-(2-methoxyethyl-1H-imidazol-2-ylmethyl)pyrimidine-4-carboxamide |

TABLE 1-continued

| Example | Structure | Compound Name |
|---|---|---|
| 98 | 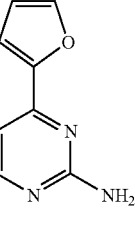 | 2-Amino-N-(1-ethyl-1H-imidazol-2-ylmethyl)-6-(2-furyl)pyrimidine-4-carboxamide |
| 99 | 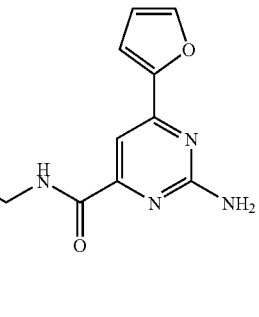 | 6-(2-Amino-6-(2-furyl)pyrimidine-4-carboxamidomethyl)pyridin-2-ylmethyl benzylcarbamate |
| 100 | 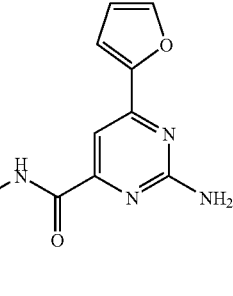 | 6-(2-Amino-6-(2-furyl)pyrimidine-4-carboxamidomethyl)pyridin-2-ylmethyl cyclopentylcarbamate |
| 101 | 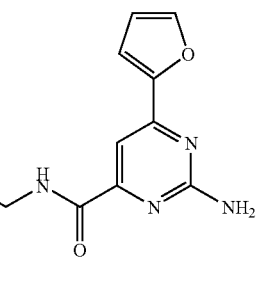 | 6-(2-Amino-6-(2-furyl)pyrimidine-4-carboxamidomethyl)pyridin-2-ylmethyl n-hexylcarbamate |
| 102 | 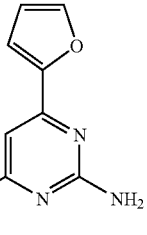 | 2-Amino-N-(2-dimethylamino-6-methylpyridin-3-ylmethyl)-6-(2-furyl)pyrimidine-4-carboxamide |

TABLE 1-continued

| Example | Structure | Compound Name |
| --- | --- | --- |
| 103 | 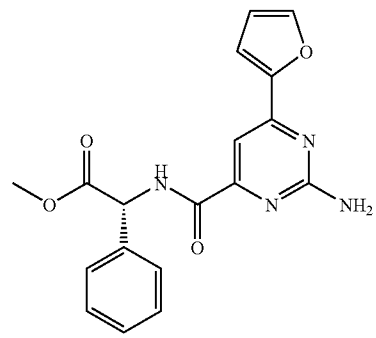 | (R)-Methyl 2-(6-(2-amino-6-(2-furyl)pyrimidine-4-carboxamido))phenylacetate |
| 104 | 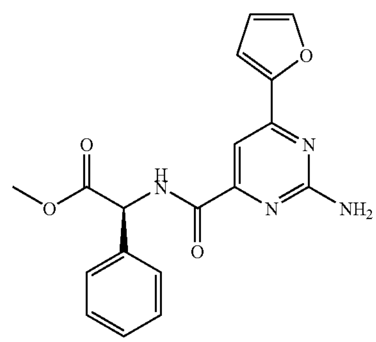 | (S)-Methyl 2-(6-(2-amino-6-(2-furyl)pyrimidine-4-carboxamido))phenylacetate |
| 105 | 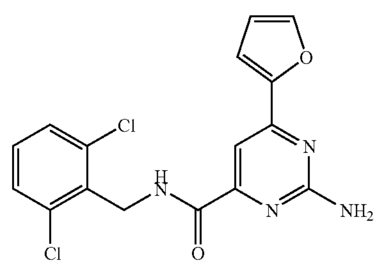 | 2-Amino-N-(2,6-dichlorobenzyl)-6-(2-furyl)pyrimidine-4-carboxamide |
| 106 | 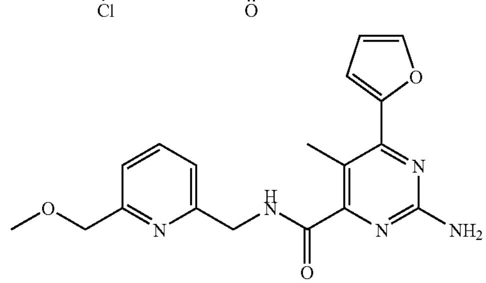 | 2-Amino-6-(2-furyl)-N-(6-methoxymethylpyridin-2-ylmethyl)-5-methylpyrimidine-4-carboxamide |
| 107 | 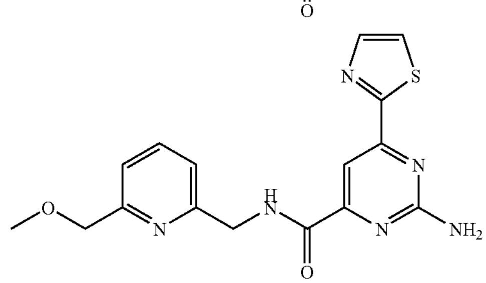 | 2-Amino-N-(6-methoxymethylpyridin-2-ylmethyl)-6-(thiazol-2-yl)pyrimidine-4-carboxamide |

TABLE 1-continued

| Example | Structure | Compound Name |
|---|---|---|
| 108 | 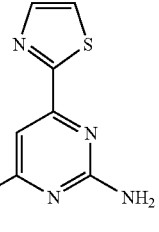 | 2-Amino-N-(3-methylpyridin-2-ylmethyl)-6-(thiazol-2-yl)pyrimidine-4-carboxamide |
| 109 | 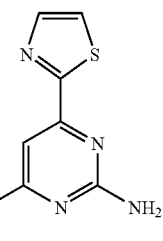 | 2-Amino-N-(6-n-propylpyridin-2-ylmethyl)-6-(thiazol-2-yl)pyrimidine-4-carboxamide |
| 110 | 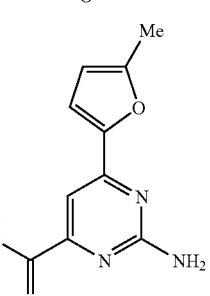 | 2-Amino-6-(5-methyl-2-furyl)-N-(2-trifluoromethylbenzyl)pyrimidine-4-carboxamide |
| 111 | 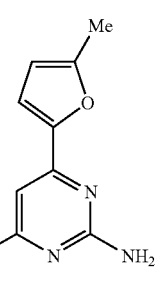 | 2-Amino-6-(5-methyl-2-furyl)-N-(2-pyridylmethyl)pyrimidine-4-carboxamide |
| 112 | 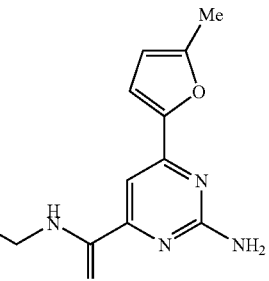 | 2-Amino-6-(5-methyl-2-furyl)-N-(1-methyl-1H-pyrrol-2-ylmethyl)pyrimidine-4-carboxamide |

TABLE 1-continued

| Example | Structure | Compound Name |
|---|---|---|
| 113 | 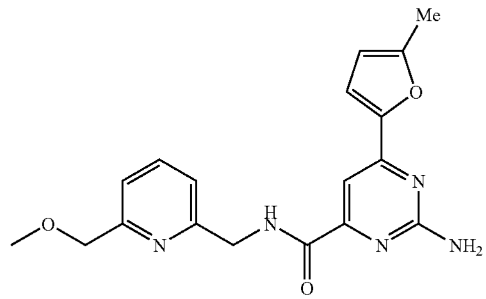 | 2-Amino-6-(5-methyl-2-furyl)-N-(6-methoxymethylpyridin-2-ylmethyl)pyrimidine-4-carboxamide |
| 114 | 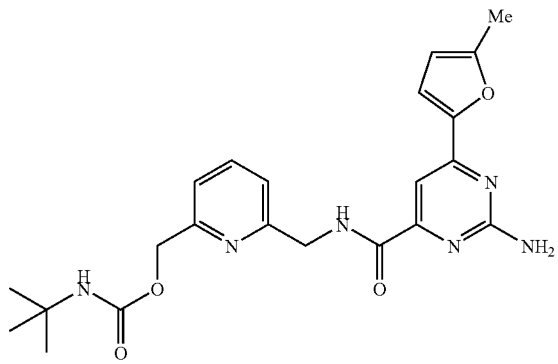 | 6-(2-Amino-6-(5-methyl-2-furyl)pyrimidine-4-carboxamidomethyl)pyridin-2-ylmethyl tert-butylcarbamate |
| 115 | 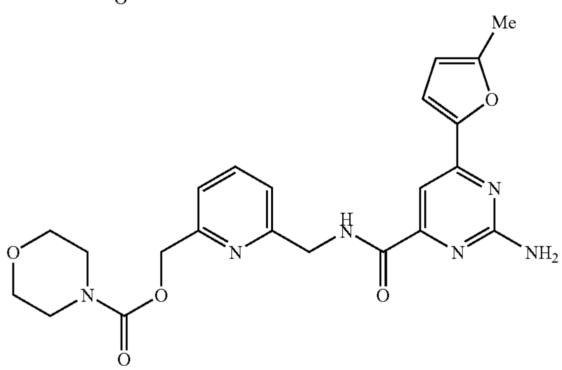 | 6-(2-Amino-6-(5-methyl-2-furyl)pyrimidine-4-carboxamidomethyl)pyridin-2-ylmethyl morpholine-1-carboxylate |
| 116 | 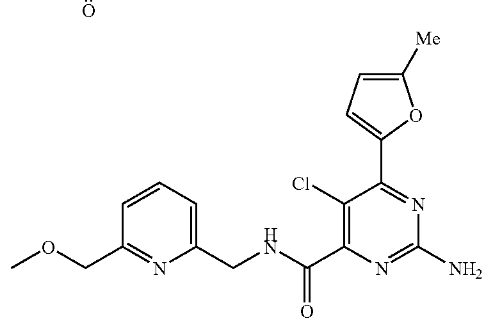 | 2-Amino-5-chloro-N-(6-methoxymethylpyridin-2-ylmethyl)-6-(5-methyl-2-furyl)pyrimidine-4-carboxamide |
| 117 | 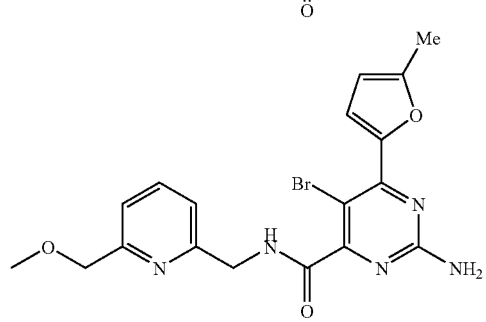 | 2-Amino-5-bromo-N-(6-methoxymethylpyridin-2-ylmethyl)-6-(5-methyl-2-furyl)pyrimidine-4-carboxamide |

TABLE 1-continued

| Example | Structure | Compound Name |
| --- | --- | --- |
| 118 | 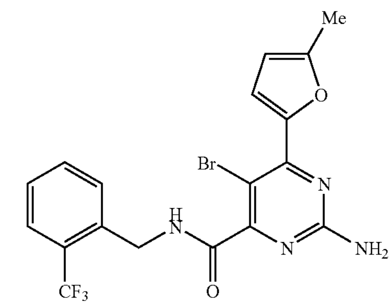 | 2-Amino-5-bromo-6-(5-methyl-2-furyl)-N-(2-trifluoromethylbenzyl)pyrimidine-4-carboxamide |
| 119 | 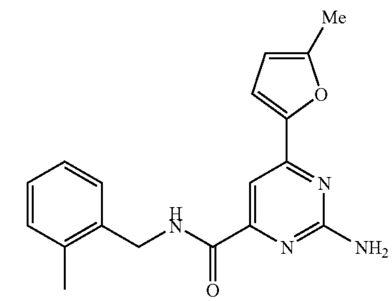 | 2-Amino-N-(2-methylbenzyl)-6-(5-methyl-2-furyl)pyrimidine-4-carboxamide |
| 120 | 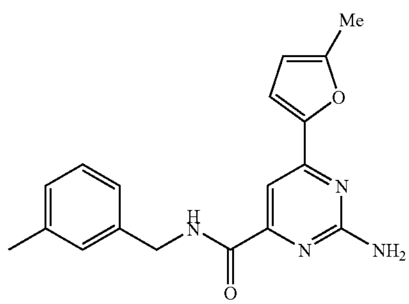 | 2-Amino-N-(3-methylbenzyl)-6-(5-methyl-2-furyl)pyrimidine-4-carboxamide |
| 121 | 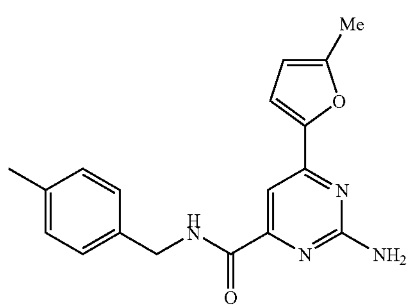 | 2-Amino-N-(4-methylbenzyl)-6-(5-methyl-2-furyl)pyrimidine-4-carboxamide |
| 122 | 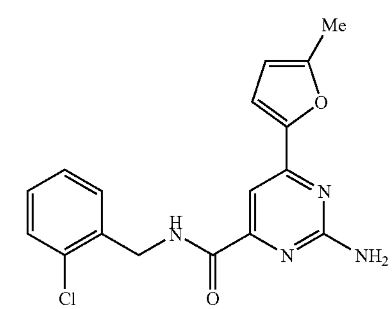 | 2-Amino-N-(2-chlorobenzyl)-6-(5-methyl-2-furyl)pyrimidine-4-carboxamide |

TABLE 1-continued
| Example | Structure | Compound Name |
|---|---|---|
| 123 | 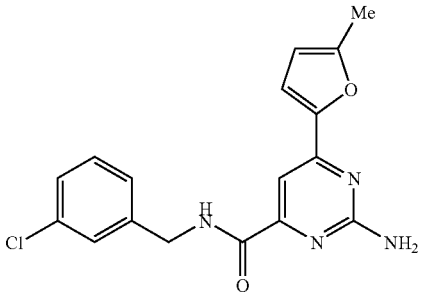 | 2-Amino-N-(3-chlorobenzyl)-6-(5-methyl-2-furyl)pyrimidine-4-carboxamide |
| 124 | 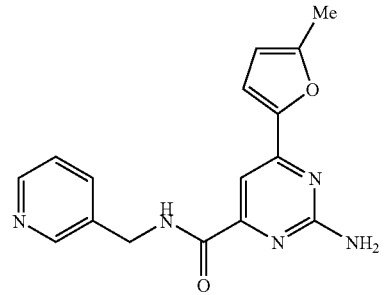 | 2-Amino-6-(5-methyl-2-furyl)-N-(3-pyridylmethyl)pyrimidine-4-carboxamide |
| 125 | 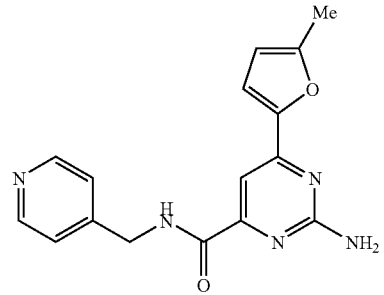 | 2-Amino-6-(5-methyl-2-furyl)-N-(4-pyridylmethyl)pyrimidine-4-carboxamide |
| 126 | 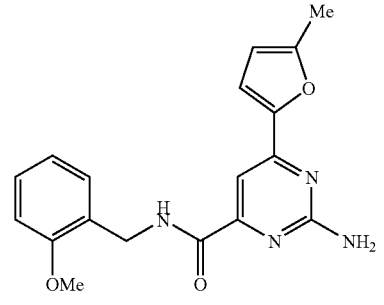 | 2-Amino-N-(2-methoxybenzyl)-6-(5-methyl-2-furyl)pyrimidine-4-carboxamide |
| 127 | 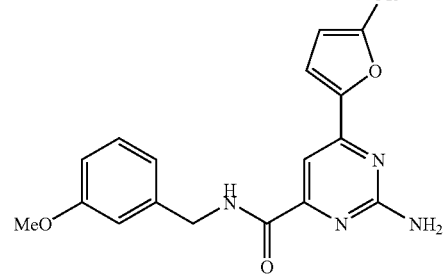 | 2-Amino-N-(3-methoxybenzyl)-6-(5-methyl-2-furyl)pyrimidine-4-carboxamide |

TABLE 1-continued

| Example | Structure | Compound Name |
| --- | --- | --- |
| 128 | 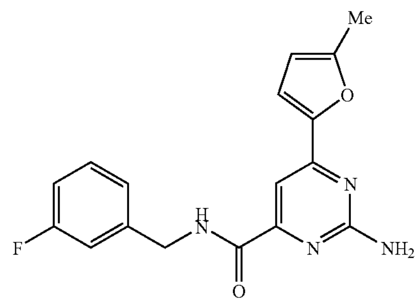 | 2-Amino-N-(3-fluorobenzyl)-6-(5-methyl-2-furyl)pyrimidine-4-caboxamide |
| 129 | 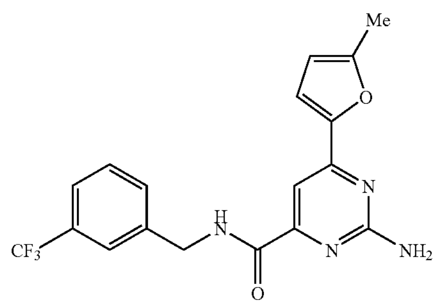 | 2-Amino-6-(5-methyl-2-furyl)-N-(3-trifluoromethylbenzyl)pyrimidine-4-carboxamide |
| 130 | 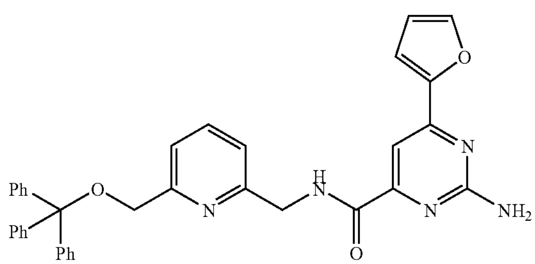 | 2-Amino-6-(2-furyl)-N-(6-(triphenylmethoxymethyl)pyridin-2-ylmethyl)pyrimidine-4-carboxamide |
| 131 | 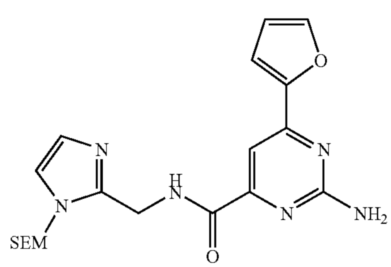 | 2-Amino-6-(2-furyl)-N-(1-(2-(trimethylsilyl)ethoxy)methyl-1H-imidazole-2-ylmethyl)pyrimidine-4-carboxamide |
| 132 | 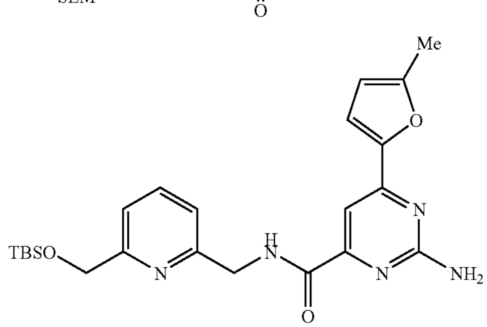 | 2-Amino-6-(5-methyl-2-furyl)-N-(6-(tert-butyldimethylsilyloxymethyl)pyridin-2-ylmethyl)pyrimidine-4-carboxamide |

TABLE 1-continued

| Example | Structure | Compound Name |
|---|---|---|
| 133 | 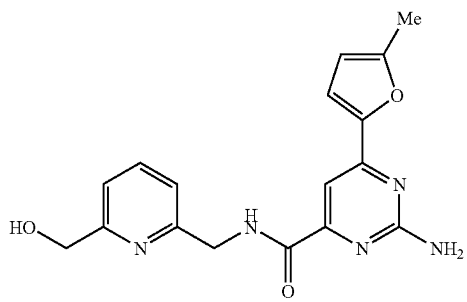 | 2-Amino-N-(6-hydroxymethylpyridin-2-ylmethyl)-6-(5-methyl-2-furyl)pyrimidine-4-carboxamide |
| 134 | 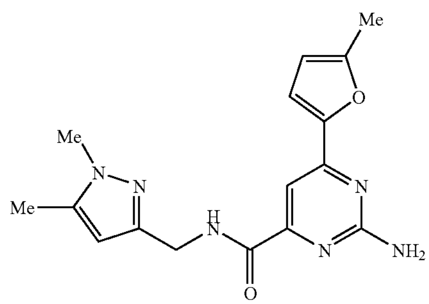 | 2-Amino-N-(1,5-dimethyl-1H-pyrazol-3-ylmethyl)-6-(5-methyl-2-furyl)pyrimidine-4-carboxamide |
| 135 | 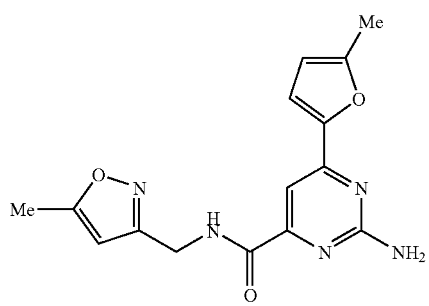 | 2-Amino-6-(5-methyl-2-furyl)-N-(5-methylisoxazol-3-ylmethyl)pyrimidine-4-carboxamide |
| 136 | 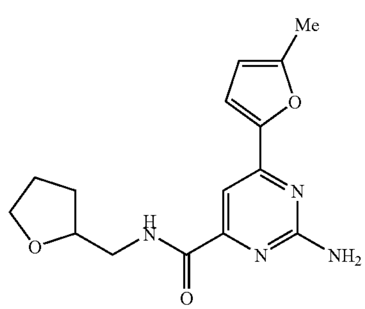 | 2-Amino-6-(5-methyl-2-furyl)-N-(tetrahydrofuran-2-ylmethyl)pyrimidine-4-carboxamide |
| 137 | 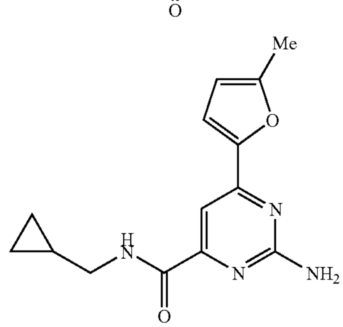 | 2-Amino-N-(cyclopropylmethyl)-6-(5-methyl-2-furyl)pyrimidine-4-carboxamide |

TABLE 1-continued

| Example | Structure | Compound Name |
| --- | --- | --- |
| 138 | 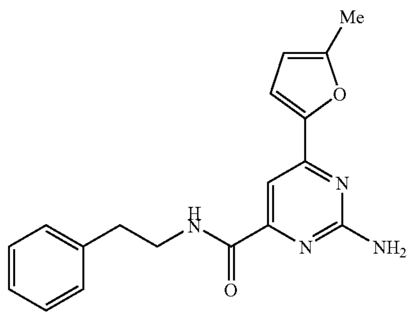 | 2-Amino-6-(5-methyl-2-furyl)-N-(2-phenylethyl)pyrimidine-4-carboxamide |
| 139 | 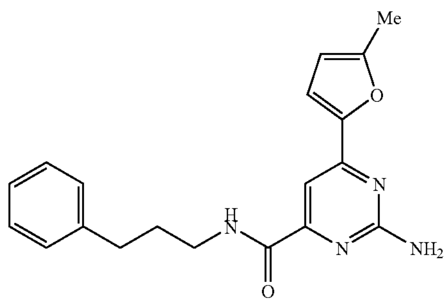 | 2-Amino-6-(5-methyl-2-furyl)-N-(3-phenylpropyl)pyrimidine-4-carboxamide |
| 140 | 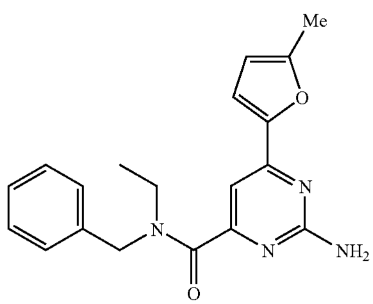 | 2-Amino-N-benzyl-N-ethyl-6-(5-methyl-2-furyl)pyrimidine-4-carboxamide |
| 141 | 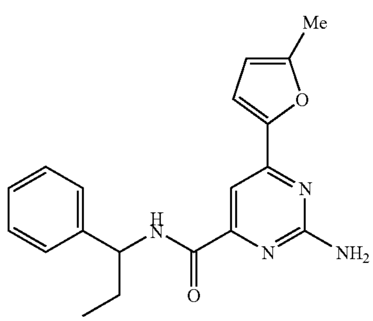 | (R,S)-2-Amino-6-(5-methyl-2-furyl)-N-(1-phenylpropyl)pyrimidine-4-carboxamide |
| 142 | 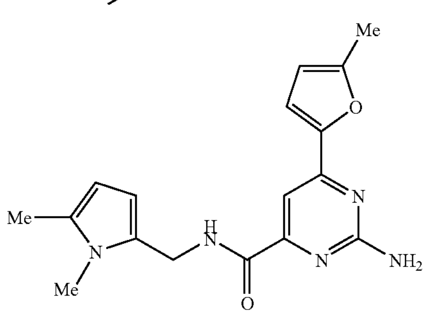 | 2-Amino-N-(1,5-dimethyl-1H-pyrrol-2-ylmethyl)-6-(5-methyl-2-furyl)pyrimidine-4-carboxamide |

TABLE 1-continued
| Example | Structure | Compound Name |
|---|---|---|
| 143 | 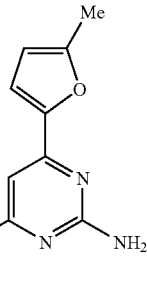 | (R,S)-2-Amino-6-(5-methyl-2-furyl)-N-(1-phenylethyl)pyrimidine-4-carboxamide |
| 144 | 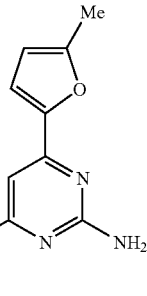 | (S)-2-Amino-N-methyl-6-(5-methyl-2-furyl)-N-(1-phenylethyl)pyrimidine-4-carboxamide |
| 145 | 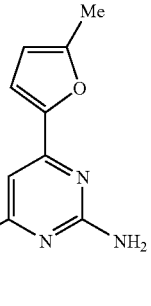 | 2-Amino-6-(5-methyl-2-furyl)-N-(1-phenylprop-2-yl)pyrimidine-4-carboxamide |
| 146 | 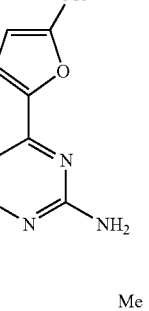 | 2-Amino-N-isobutyl-6-(5-methyl-2-furyl)pyrimidine-4-carboxamide |
| 147 | 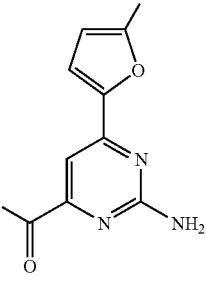 | 2-Amino-N-hexyl-6-(5-methyl-2-furyl)pyrimidine-4-carboxamide |

TABLE 1-continued

| Example | Structure | Compound Name |
|---|---|---|
| 148 | 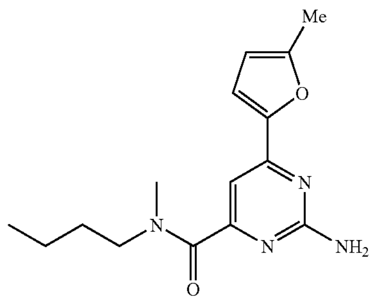 | 2-Amino-N-butyl-N-methyl-6-(5-methyl-2-furyl)pyrimidine-4-carboxamide |
| 149 | 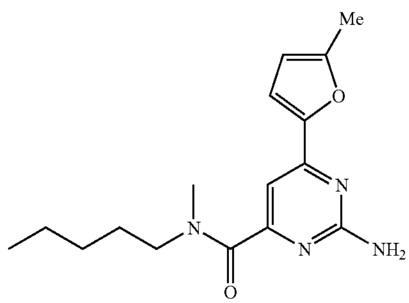 | 2-Amino-N-methyl-6-(5-methyl-2-furyl)-N-pentylpyrimidine-4-carboxamide |
| 150 | 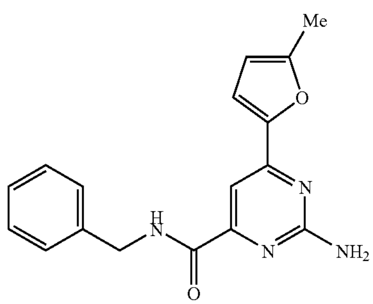 | 2-Amino-N-benzyl-6-(5-methyl-2-furyl)pyrimidine-4-carboxamide |
| 151 | 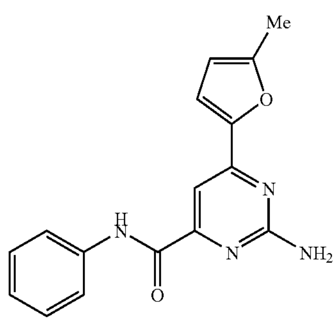 | 2-Amino-6-(5-methyl-2-furyl)-N-phenylpyrimidine-4-carboxamide |
| 152 | 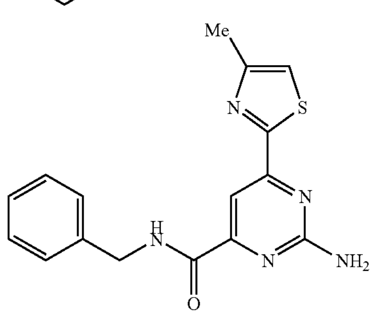 | 2-Amino-N-benzyl-6-(4-methylthiazol-2-yl)pyrimidine-4-carboxamide |

TABLE 1-continued

| Example | Structure | Compound Name |
|---|---|---|
| 153 | 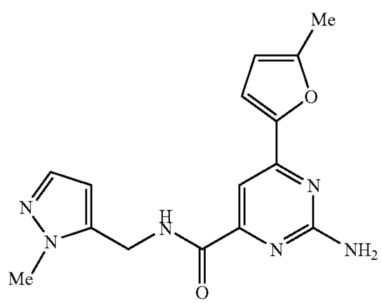 | 2-Amino-6-(5-methyl-2-furyl)-N-(1-methyl-1H-pyrazol-5-ylmethyl)pyrimidine-4-carboxamide |
| 154 | 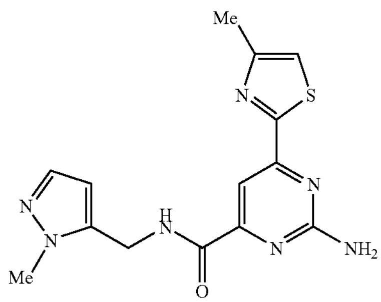 | 2-Amino-N-(1-methyl-1H-pyrazol-5-ylmethyl)-6-(4-methylthiazol-2-yl)pyrimidine-4-carboxamide |
| 155 | 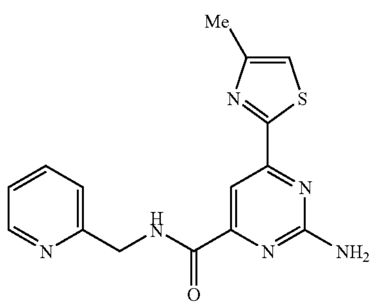 | 2-Amino-6-(4-methylthiazol-2-yl)-N-(pyridin-2-ylmethyl)pyrimidine-4-carboxamide |
| 156 | 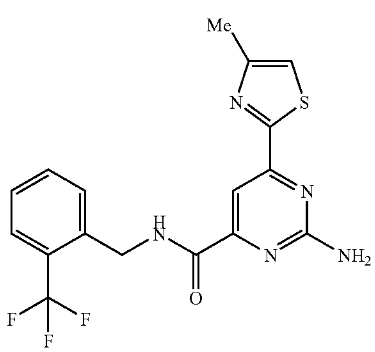 | 2-Amino-6-(4-methylthiazol-2-yl)-N-(2-trifluoromethylbenzyl)pyrimidine-4-carboxamide |
| 157 | 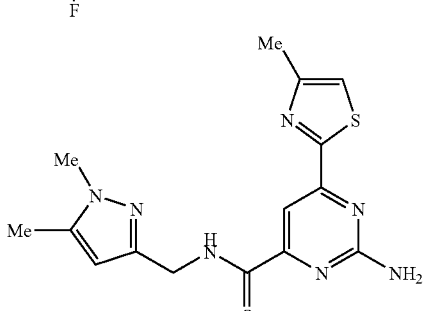 | 2-Amino-N-(1,5-dimethyl-1H-pyrazol-3-ylmethyl)-6-(4-methylthiazol-2-yl)pyrimidine-4-carboxamide |

TABLE 1-continued

| Example | Structure | Compound Name |
|---|---|---|
| 158 | 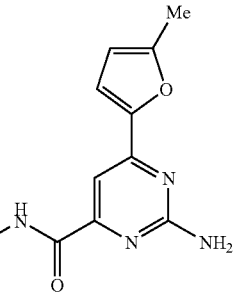 | 2-Amino-6-(5-methyl-2-furyl)-N-(1-methyl-1H-pyrazol-3-ylmethyl)pyrimidine-4-carboxamide |
| 159 | 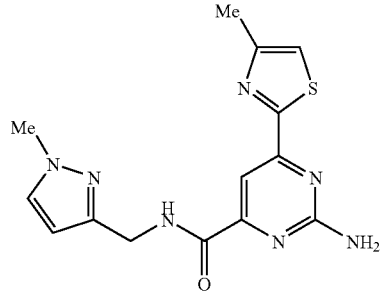 | 2-Amino-N-(1-methyl-1H-pyrazol-3-ylmethyl)-6-(4-methylthiazol-2-yl)pyrimidine-4-carboxamide |
| 160 | 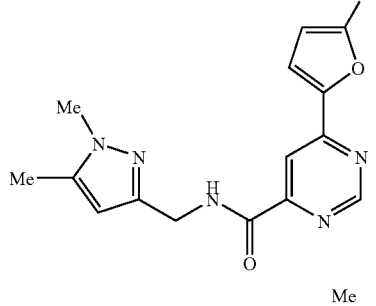 | N-(1,5-Dimethyl-1H-pyrazol-3-ylmethyl)-6-(5-methyl-2-furyl)pyrimidine-4-carboxamide |
| 161 | 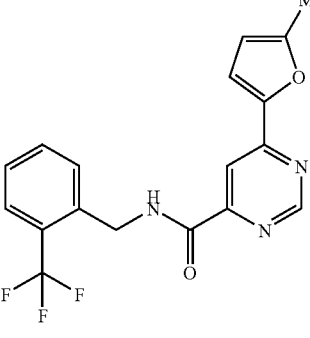 | 6-(5-Methyl-2-furyl)-N-(2-trifluoromethylbenzyl)pyrimidine-4-carboxamide |
| 162 | 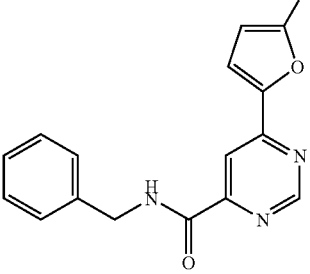 | N-Benzyl-6-(5-methyl-2-furyl)pyrimidine-4-carboxamide |

TABLE 1-continued

| Example | Structure | Compound Name |
| --- | --- | --- |
| 163 | 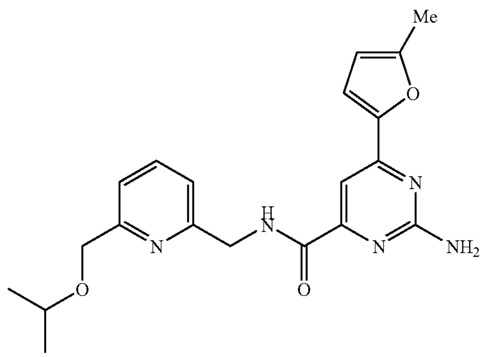 | 2-Amino-6-(5-methyl-2-furyl)-N-(6-(isopropyloxymethyl)pyridine-2-ylmethyl)pyrimidine-4-carboxamide |
| 164 | 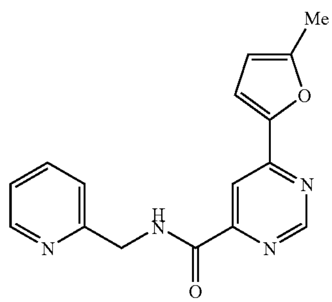 | 6-(5-Methyl-2-furyl)-N-(2-pyridylmethyl)pyrimidine-4-carboxamide |
| 165 | 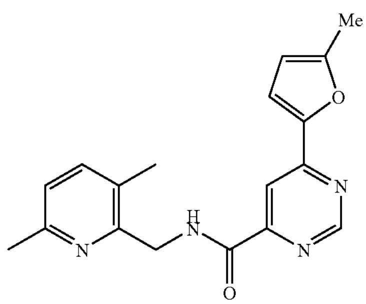 | N-(3,6-Dimethylpyridin-2-ylmethyl)-6-(5-methyl-2-furyl)pyrimidine-4-carboxamide |
| 166 | 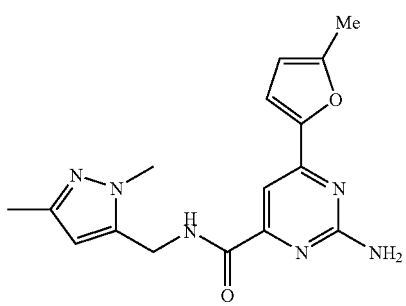 | 2-Amino-N-(1,3-dimethyl-1H-pyrazol-5-ylmethyl)-6-(5-methyl-2-furyl)pyrimidine-4-carboxamide |
| 167 | 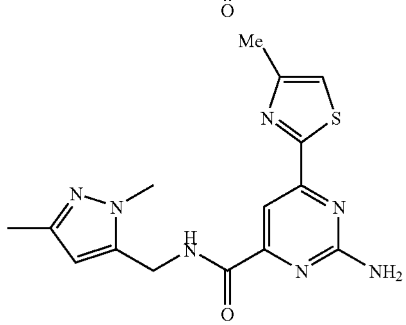 | 2-Amino-N-(1,3-dimethyl-1H-pyrazol-5-ylmethyl)-6-(4-methylthiazol-2-yl)pyrimidine-4-carboxamide |

TABLE 1-continued

| Example | Structure | Compound Name |
|---|---|---|
| 168 | 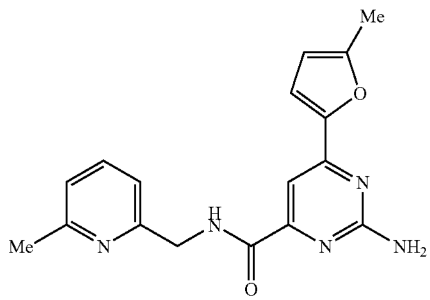 | 2-Amino-6-(5-methyl-2-furyl)-N-(6-methylpyridin-2-ylmethyl)pyrimidine-4-carboxamide |
| 169 | 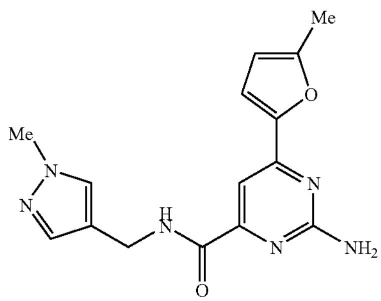 | 2-Amino-6-(5-methyl-2-furyl)-N-(1-methyl-1H-pyrazol-4-ylmethyl)pyrimidine-4-carboxamide |
| 170 | 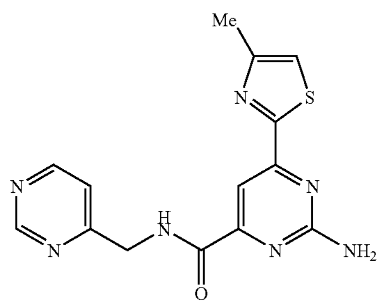 | 2-Amino-6-(4-methylthiazol-2-yl)-N-(pyrimidin-4-ylmethyl)pyrimidine-4-carboxamide |
| 171 | 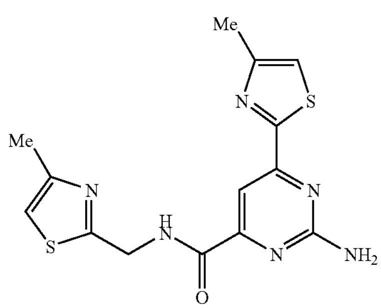 | 2-Amino-6-(4-methylthiazol-2-yl)-N-(4-methylthiazol-2-ylmethyl)pyrimidine-4 carboxamide |
| 172 | 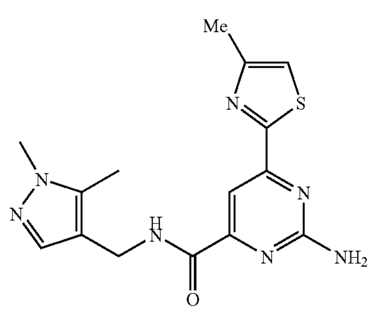 | 2-Amino-N-(1,5-dimethyl-1H-pyrazol-4-ylmethyl)-6-(4-methylthiazol-2-yl)pyrimidine-4-carboxamide |

TABLE 1-continued

| Example | Structure | Compound Name |
|---|---|---|
| 173 | 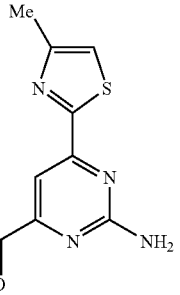 | 2-Amino-N-(1,3-dimethyl-1H-pyrazol-4-ylmethyl)-6-(4-methylthiazol-2-yl)pyrimidine-4-carboxamide |
| 174 | 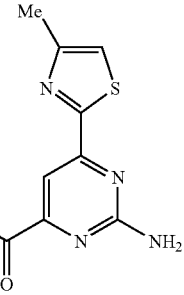 | 2-Amino-6-(4-methylthiazol-2-yl)-N-(pyridin-3-ylmethyl)pyrimidine-4-carboxamide |
| 175 | 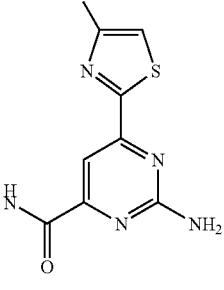 | 2-Amino-6-(4-methylthiazol-2-yl)-N-(3-trifluoromethylbenzyl)pyrimidine-4-carboxamide |
| 176 | 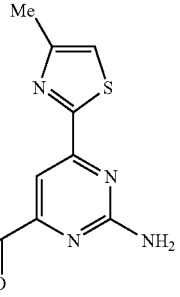 | 2-Amino-N-(2-methylbenzyl)-6-(4-methylthiazol-2-yl)pyrimidine-4-carboxamide |
| 177 | 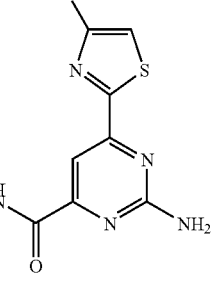 | 2-Amino-N-(6-methoxymethylpyridin-2-ylmethyl)-6-(4-methylthiazol-2-yl)pyrimidine-4-carboxamide |

TABLE 1-continued

| Example | Structure | Compound Name |
| --- | --- | --- |
| 178 | 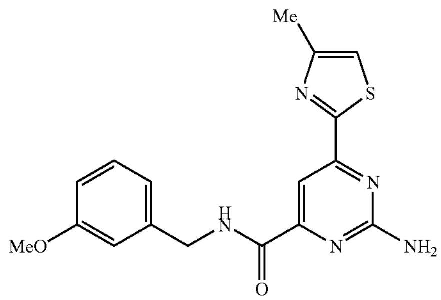 | 2-Amino-N-(3-methoxybenzyl)-6-(4-methylthiazol-2-yl)pyrimidine-4-carboxamide |
| 179 | 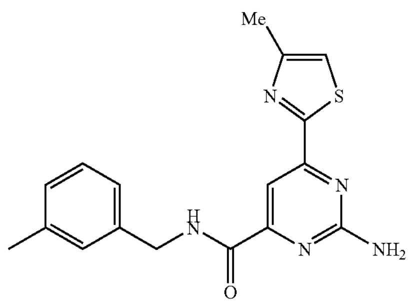 | 2-Amino-N-(3-methylbenzyl)-6-(4-methylthiazol-2-yl)pyrimidine-4-carboxamide |
| 180 | 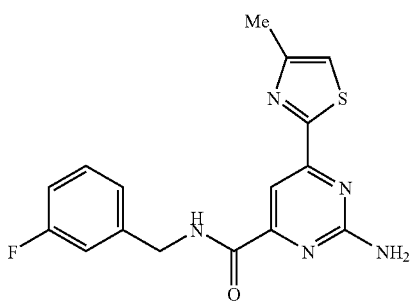 | 2-Amino-N-(3-fluorobenzyl)-6-(4-methylthiazol-2-yl)pyrimidine-4-carboxamide |
| 181 | 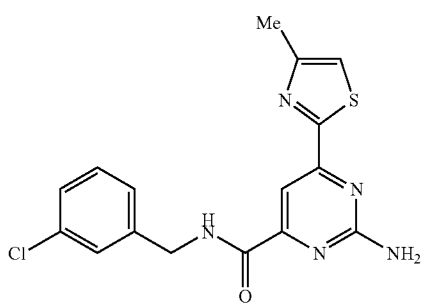 | 2-Amino-N-(3-chlorobenzyl)-6-(4-methylthiazol-2-yl)pyrimidine-4-carboxamide |
| 182 | 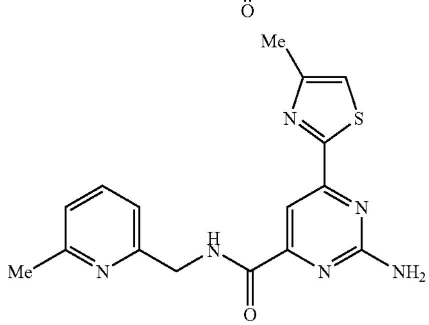 | 2-Amino-N-(6-methylpyridin-2-ylmethyl)-6-(4-methylthiazol-2-yl)pyrimidine-4-carboxamide |

TABLE 1-continued

| Example | Structure | Compound Name |
| --- | --- | --- |
| 183 | 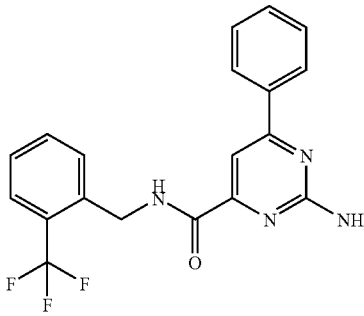 | 2-Amino-6-phenyl-N-(2-trifluoromethylbenzyl)pyrimidine-4-carboxamide |
| 184 | 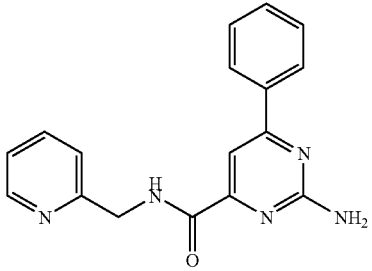 | 2-Amino-6-phenyl-N-(pyridin-2-ylmethyl)pyrimidine-4-carboxamide |
| 185 | 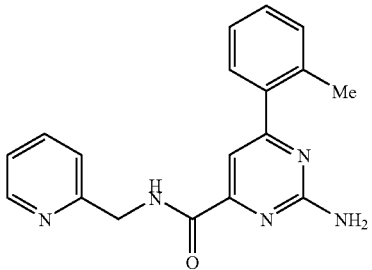 | 2-Amino-6-(2-methylphenyl)-N-(pyridin-2-ylmethyl)pyrimidine-4-carboxamide |
| 186 | 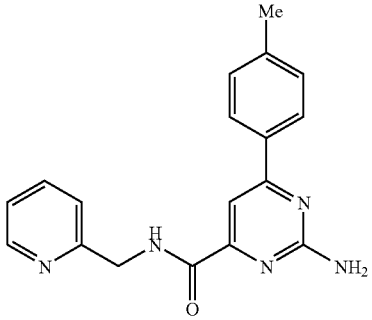 | 2-Amino-6-(4-methylphenyl)-N-(pyridin-2-ylmethyl)pyrimidine-4-carboxamide |
| 187 | 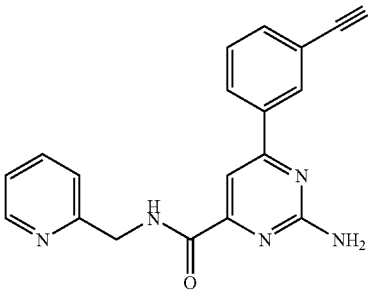 | 2-Amino-6-(3-cyanophenyl)-N-(pyridin-2-ylmethyl)pyrimidine-4-carboxamide |

TABLE 1-continued

| Example | Structure | Compound Name |
|---|---|---|
| 188 | 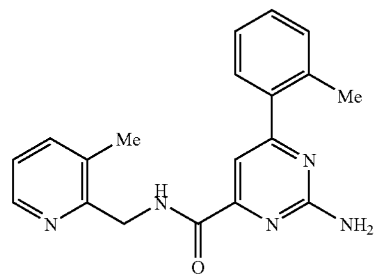 | 2-Amino-6-(2-methylphenyl)-N-(3-methylpyridin-2-ylmethyl)pyrimidine-4-carboxamide |
| 189 | 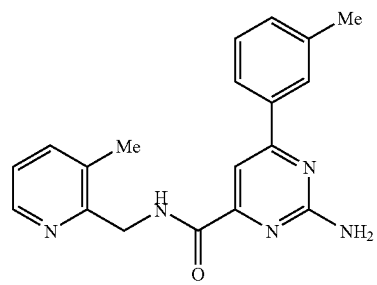 | 2-Amino-6-(3-methylphenyl)-N-(3-methylpyridin-2-ylmethyl)pyrimidine-4-carboxamide |
| 190 | 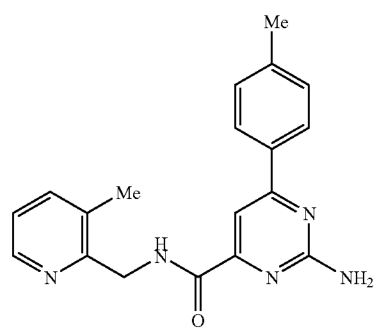 | 2-Amino-6-(4-methylphenyl)-N-(3-methylpyridin-2-ylmethyl)pyrimidine-4-carboxamide |
| 191 | 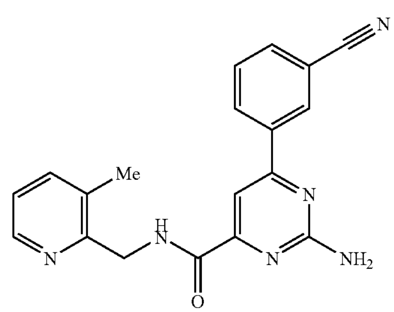 | 2-Amino-6-(3-cyanophenyl)-N-(3-methylpyridin-2-ylmethyl)pyrimidine-4-carboxamide |
| 192 | 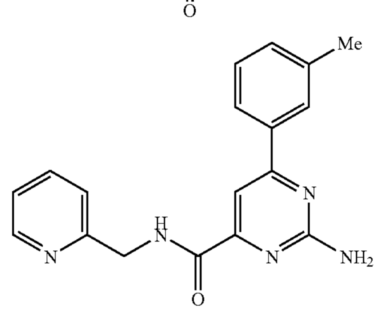 | 2-Amino-6-(3-methylphenyl)-N-(pyridin-2-ylmethyl)pyrimidine-4-carboxamide |

TABLE 1-continued

| Example | Structure | Compound Name |
| --- | --- | --- |
| 193 | 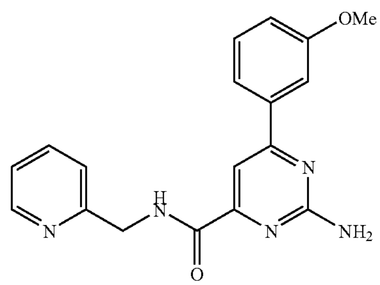 | 2-Amino-6-(3-methoxyphenyl)-N-(pyridin-2-ylmethyl)pyrimidine-4-carboxamide |
| 194 | 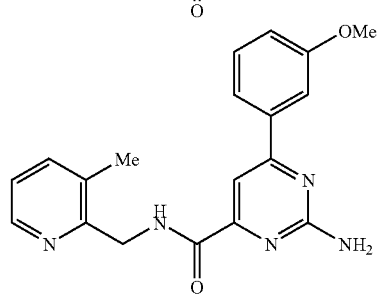 | 2-Amino-6-(3-methoxyphenyl)-N-(3-methylpyridin-2-ylmethyl)pyrimidine-4-carboxamide |
| 195 | 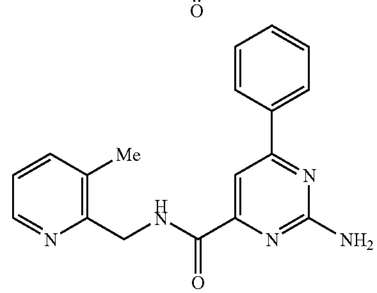 | 2-Amino-N-(3-methylpyridin-2-ylmethyl)-6-phenylpyrimidine-4-carboxamide |

The general synthetic methods used for the preparation of these Examples are set out below as Methods A to AK. Table 2 sets out the Method used and yield obtained for each Example, together with the analytical data.

Method A

2-Amino-4-chloro-6-(2-furyl)pyrimidine

A solution of 2-(tributylstannyl)furan (35.7 g, 100 mmol) in DMF (100 mL) was treated with 2-amino-4,6-dichloropyrimidine (16.4 g, 100 mmol) and dichlorobis(triphenylphosphine)palladium (II) (3.51 g, 5.0 mmol). The suspension was stirred at 80° C. for 18 h, allowed to cool to room temperature and poured onto ice (400 g). The solid precipitate was filtered off, washed with water, dried in air, and the filtrate was extracted with EtOAc (300 mL), washed with water (100 mL), mixed with the solid precipitate and concentrated. The crude product was purified by chromatography [$SiO_2$; EtOAc:toluene (0:1-1:9-2:3)] and the material with $R_f$ 0.23 (isopropyl ether) was triturated with isohexane to give the title compound (11.1 g, 57%) as a yellow solid; mp. 133-140° C.; NMR $\delta_H$ (400 MHz, DMSO) 6.70 (1H, q, J 2.0 Hz), 6.95 (1H, s), 7.16 (2H, br s), 7.27 (1H, d, J 3.6 Hz) and 7.92 (1H, t, J 1.0 Hz).

Method B

2-Amino-6-(2-furyl)pyrimidine-4-carbonitrile

A solution of 2-amino-4-chloro-6-(2-furyl)pyrimidine (9.78 g, 50.0 mmol) in DMSO (200 mL) was treated with sodium cyamide (14.7 g, 300 mmol) and 1,4-diazabicyclo[2.2.2]octane (DABCO) (0.56 g, 5.0 mmol). The suspension was stirred for 4 days, and more DABCO (5.04 g, 45 mmol) and DMSO (100 mL) were added. The suspension was stirred for a further 2 days, poured onto a mixture of ice (750 g) and water (750 mL), the crude product was filtered off, washed with water and MeCN, and dried in air to give the title compound (7.1 g, 77%) as a brown solid; m.p. 193-194° C.; NMR $\delta_H$ (400 MHz, DMSO) 6.74 (1H, q, J 1.6 Hz), 7.32 (2H, br s), 7.39 (1H, d, J 3.6 Hz), 7.43 (1H, s) and 7.98 (1H, d, J 1.2 Hz); M/Z 187 (M+H)$^+$.

The following novel nitriles were synthesised from the appropriate 4-chloropyrimidine by Method B.

2-Amino-6-(5-methyl-2-furyl)pyrimidine-4-carbonitrile

NMR $\delta_H$ (400 MHz, DMSO) 2.38 (3H, s), 6.37-6.38 (1H, m), 7.28 (2H, s), 7.32 (1H, d, J 3.5 Hz) and 7.37 (1H, s); M/Z 201 (M+H)$^+$

2-Amino-6-(2-thiazolyl)pyrimidine-4-carbonitrile

IR $v_{max}$ (DR)/cm$^{-1}$ 3457, 3325, 3223, 3110, 2246, 1646, 1572, 1435, 1388, 1348 and 1241; NMR $\delta_H$ (400 MHz, DMSO) 7.57 (2H, br s), 7.62 (1H, s), 8.07 (1H, d, J 3.1 Hz) and 8.12 (1H, d, J 3.0 Hz)

Method C

2-Amino-6-(2-furyl)pyrimidine-4-carboxylic acid

A suspension of 2-amino-6-(2-furyl)pyrimidine-4-carbonitrile (7.06 g, 37.9 mmol) in water (30 mL) was treated carefully with concentrated sulfuric acid (30 mL), stirred at 100° C. for 2 h, allowed to cool to room temperature and poured onto a mixture of ice (150 g) and water (150 mL). After standing for 1 h the crude product was filtered off, washed with water and MeCN, and dried in air to give the title compound (7.02 g, 90%) as a brown solid; NMR $\delta_H$ (400 MHz, DMSO) 6.71 (1H, dd, J 1.6, 3.6 Hz), 7.04 (2H, br s), 7.30 (1H, d, J 3.6 Hz), 7.36 (1H, s) and 7.94 (1H, d, J 1.2 Hz); Anal. Calc for $C_9H_7N_3O_3.1.6H_2O$: C, 46.20; H, 4.39; N, 17.96. Found: C, 46.22; H, 4.22; N, 17.82.

The following novel carboxylic acids were synthesised from the appropriate pyrimidine-4-carbonitrile by Method C.

2-Amino-6-(5-methyl-2-furyl)pyrimidine-4-carboxylic acid

NMR $\delta_H$ (400 MHz, DMSO) 2.38 (3H, s), 6.33-6.34 (1H, m), 6.97 (2H, s), 7.21 (1H, d, J 3.0 Hz), 7.30 (1H, s) and 13.12 (1H, s); M/Z 220 (M+H)$^+$

2-Amino-6-(2-thiazolyl)pyrimidine-4-carboxylic acid

IR $v_{max}$ (DR)/cm$^{-1}$ 3125 br, 1748, 1673, 1625, 1481, 1427, 1356 and 1275; NMR $\delta_H$ (400 MHz, DMSO) 7.69 (1H, s), 8.01 (1H, d, J 3.1 Hz), 8.09 (1H, d, J 3.2 Hz); M/Z 223 (M+H)$^+$

2-Amino-6-(4-methylthiazol-2-yl)pyrimidine-4-carboxylic acid

IR $v_{max}$ (DR)/cm$^{-1}$ 3418, 3333, 3225, 1656, 1589, 1515, 1451, 1352 and 1225; NMR $\delta_H$ (400 MHz, DMSO) 2.46 (3H, s), 7.21 (2H, br s), 7.56 (1H, s) and 7.65 (1H, s); M/Z 237 (M+H)$^+$ Method D

2-Amino-6-(2-furyl)-N-(3-methylpyridin-2-yl)methylpyrimidine-4-carboxamide (Example 11)

A suspension of 2-amino-6-(2-furyl)pyrimidine-4-carboxylic acid (206 mg, 1.0 mmol) in DMF (5 mL) was treated with N,N'-carbonyldiimidazole (162 mg, 1.0 mmol), stirred for 2 h, treated with 3-methylpyridine-2-methanamine (244 mg, 2.0 mmol), stirred for 2 h, poured onto water (50 mL) and extracted with EtOAc (2×25 mL). The extracts were washed with water, concentrated in vacuo, and the crude product was triturated with ether to give the title compound (109 mg, 35%) as a yellow solid.

Method E

2-[(6-Methoxymethyl)pyridin-2-yl]methylisoindole-1,3(2H)-dione

A solution of 2-[(6-hydroxymethyl)pyridin-2-yl]methylisoindole-1,3(2H)-dione (4.02 g, 15.0 mmol) in DMF (20 mL) at 0° C. was treated with NaH (60% dispersion in mineral oil, 600 mg, 15.0 mmol), stirred for 15 min at 0° C., treated with methyl iodide (1.03 ml, 16.5 mmol), warmed to room temperature and stirred for 2 days. The reaction mixture was poured onto water (100 mL), extracted with EtOAc (3×100 mL), dried (MgSO$_4$), concentrated in vacuo and purified by chromatography [SiO$_2$; isohexane:EtOAc (1:4)] to give the title compound (1.11 g, 26%) as a white solid; NMR $\delta_H$ (400 MHz, CDCl$_3$) 3.42 (3H, s), 4.51 (2H, s), 5.01 (2H, s), 7.10 (1H, d, J 8.0 Hz), 7.30 (1H, d, J 8.0 Hz), 7.63 (1H, t, J 7.5 Hz), 7.73-7.76 (2H, m) and 7.87-7.91 (2H, m); R$_f$(EtOAc)=0.77.

Method F

6-Methoxymethylpyridine-2-methanamine

A solution of 2-[(6-methoxymethyl)pyridin-2-yl]methylisoindole-1,3(2H)-dione (1.11 g, 3.94 mmol) in EtOH (75 mL) was treated with hydrazine hydrate (0.95 mL, 19.5 mmol), stirred at 80° C. overnight, cooled to room temperature, filtered through Celite and concentrated in vacuo to give the title compound (265 mg, 44%) as a yellow oil; NMR $\delta_H$ (400 MHz, CDCl$_3$) 2.10 (2H, br s), 3.48 (3H, s), 3.97 (2H, s), 4.57 (2H, s), 7.18 (1H, d, J 8.0 Hz), 7.28 (1H, d, J 8.0 Hz) and 7.66 (1H, t, J 7.5 Hz).

Method G

3-Methoxymethylpyridine-2-carbonitrile

A stirred solution of 3-bromomethylpyridine-2-carbonitrile (591 mg, 3.0 mmol) in MeOH (10 mL) at 0° C. was treated with NaOMe (324 mg, 6.0 mmol), warmed to room temperature, stirred for 2 h, concentrated in vacuo and partitioned between EtOAc (50 mL) and water (30 mL). The organic phase was dried (MgSO$_4$), concentrated in vacuo and purified by chromatography [SiO$_2$; hexane:EtOAc (9:1-4:1)] to give the title compound (297 mg, 67%) as a clear oil; NMR $\delta_H$ (400 MHz, CDCl$_3$) 3.51 (3H, s), 4.68 (2H, s), 7.50-7.55 (1H, m), 7.92-7.96 (1H, m) and 8.63 (1H, dd, J 5.0, 1.5 Hz); R$_f$[isohexane:EtOAc (4:1)]=0.65.

The following novel nitriles were synthesised from 6-bromomethyl-3-methylpyridine-2-carbonitrile by Method G.

6-Methoxymethyl-3-methylpyridine-2-carbonitrile

NMR $\delta_H$ (400 MHz, CDCl$_3$) 2.55 (3H, s), 3.47 (3H, s), 4.56 (2H, s), 7.56 (1H, d, J 8.0 Hz) and 7.67 (1H, d, J 8.5 Hz); HPLC 1.6 min. (20/50).

6-Cyclopropylmethoxymethyl-3-methylpyridine-2-carbonitrile

NMR $\delta_H$ (400 MHz, CDCl$_3$) 0.24-0.28 (2H, m), 0.56-0.61 (2H, m), 1.09-1.18 (1H, m), 2.57 (3H, s), 3.42 (2H, d, J 7.0 Hz), 4.66 (2H, s), 7.63 (1H, d, J 8.0 Hz) and 7.68 (1H, d, J 8.0 Hz); HPLC 1.2 min. (50/80).

Method H

3-(N,N-Dimethylamino)methylpyridine-2-carbonitrile

A solution of 3-bromomethylpyridine-2-carbonitrile (591 mg, 3.0 mmol) in MeCN (10 mL) was treated with dimethylamine (7.9-M in water, 1.9 mL, 15 mmol) and heated at 50° C. for 4 h. The solution was treated with MP-carbonate (2.0 g, 6.0 mmol), stirred for 30 min, filtered through Celite and the residue was washed with EtOAc. The filtrate was concentrated in vacuo, and the crude product was purified by chromatography [SiO$_2$; MeOH:EtOAc:isohexane (0:4:1-1:9:0)] to give the title compound (541 mg, 96%) as an orange oil; NMR δ$_H$ (400 MHz, CDCl$_3$) 2.31 (6H, s), 3.67 (2H, s), 7.50 (1H, dd, J 8.0, 4.5 Hz), 7.94 (1H, dd, J 8.0, 1.5 Hz) and 8.61 (1H, dd, J 4.5, 1.5 Hz); M/Z 162 (M+H)$^+$.

The following novel compound was synthesised from 3-bromomethylpyridine-2-carbonitrile and morpholine by Method H.

3-(4-Morpholinyl)methylpyridine-2-carbonitrile

NMR δ$_H$ (400 MHz, CDCl$_3$) 2.50-2.55 (4H, m), 3.68-3.74 (6H, m), 7.50 (1H, dd, J 8.0, 5.0 Hz), 7.92-7.95 (1H, m) and 8.62 (1H, dd, J 4.5, 1.5 Hz); M/Z 204 (M+H)$^+$.

Method I

3,6-Dimethylpyridine-2-methanamine

A solution of 3,6-dimethylpyridine-2-carbonitrile (264 mg, 2.00 mmol) in EtOH (10 mL) was treated with Raney-Ni (approximately 100 mg) and stirred under an atmosphere of hydrogen for 4 h at room temperature. The mixture was filtered through Celite and concentrated in vacuo to give the title compound (270 mg, 99%) as a yellow oil; NMR δ$_H$ (400 MHz, CDCl$_3$) 2.31 (3H, s), 2.51 (3H, s), 4.17 (2H, s), 7.00 (1H, d, J 7.5 Hz) and 7.37 (1H, d, J 7.5 Hz); M/Z 137 (M+H)$^+$.

The following novel amines were also synthesised by Method I from the appropriate nitrile.

3-Methoxymethylpyridine-2-methanamine

M/Z 153 (M+H)$^+$.

3-(N,N-Dimethylamino)methylpyridine-2-methanamine

M/Z 166 (M+H)$^+$.

3-(4-Morpholinyl)methylpyridine-2-methanamine

NMR δ$_H$ (400 MHz, CDCl$_3$) 2.41-2.47 (4H, m), 3.50 (2H, s), 3.68 (4H, t, J 4.5 Hz), 4.02 (2H, s), 7.14 (1H, dd, J 7.5, 4.5 Hz), 7.54 (1H, dd, J 7.5, 1.5 Hz) and 8.49 (1H, dd, J 5.0, 1.5 Hz); M/Z 208 (M+H)$^+$.

2-Dimethylamino-6-methylpyridine-3-methanamine

NMR δ$_H$ (400 MHz, CDCl$_3$) 1.79 (2H, s), 2.45 (3H, s), 2.85 (6H, s), 3.96 (2H, s), 6.74 (1H, d, J 7.5 Hz) and 7.46 (1H, d, J 7.5 Hz).

6-Methoxymethyl-3-methylpyridine-2-methanamine

NMR δ$_H$ (400 MHz, CDCl$_3$) 1.74 (2H, s), 2.28 (3H, s), 3.47 (3H, s), 3.94 (2H, s), 4.55 (2H, s), 7.18-7.20 (1H, m) and 7.41-7.44 (1H, m); M/Z 167 (M+H)$^+$

6-Cyclopropylmethoxymethyl-3-methylpyridine-2-methanamine

NMR δ$_H$ (400 MHz, CDCl$_3$) 0.22-0.28 (2H, m), 0.54-0.61 (2H, m), 1.08-1.19 (1H, m), 1.76 (2H, s), 2.30 (3H, s), 3.41-3.43 (2H, m), 3.96 (2H, s), 4.65 (2H, d, J 4.0 Hz), 7.25-7.27 (1H, m) and 7.42-7.45 (1H, m); HPLC 0.73 min. (20/50).

3-Aminomethyl-N,N-dimethylbenzamide

NMR δ$_H$ (400 MHz, DMSO) 1.92-3.54 (2H, s), 2.94 (6H, d, J 26.0 Hz), 3.71 (2H, s) and 7.05-7.48 (4H, m)

1-(2-(Trimethylsilyl)ethoxy)methyl-1H-imidazole-2-methanamine dihydrochloride NMR δ$_H$ (400 MHz, DMSO) 0.00 (9H, s), 0.93-0.89 (2H, m), 3.55-3.59 (2H, m), 4.40 (2H, s), 5.64 (2H, s), 7.57 (1H, s), 7.75 (1H, s) and 8.94 (2H, br s); M/Z 228 (M+H)$^+$

N-(6-Aminomethyl-5-methylpyridine-2-ylmethyl)-N-methylacetamide

NMR δ$_H$ (400 MHz, DMSO) (1:1 mixture of rotamers) 2.16 (1.5H, s), 2.17 (1.5H, s), 2.25 (1.5H, s), 2.27 (1.5H, s), 2.98 (1.5H, s), 3.07 (1.5H, s), 3.92 (1H, s), 3.94 (1H, s), 4.58 (1H, s), 4.67 (1H, s), 6.93 (0.5H, d, J 7.5 Hz), 7.03 (0.5H, d, J 7.5 Hz), 7.37 (0.5H, d, J 7.5 Hz) and 7.42 (0.5H, d, J 7.5 Hz); M/Z 208 (M+H)$^+$

6-(Isopropoxymethyl)pyridine-2-methanamine

NMR δ$_H$ (400 MHz, CDCl$_3$) 1.17 (6H, br m), 3.70 (1H, m), 3.80 (2H, br m), 4.50 (2H, s), 7.20-7.40 (2H, m) and 7.70-7.80 (1H, m); M/Z 183 (M+H)$^+$

6-n-Propylpyridine-2-methanamine

NMR δ$_H$ (400 MHz, CDCl$_3$) 0.92 (3H, m), 1.76 (2H, m), 2.94 (2H, m), 4.38 (2H, m), 7.65 (1H, d, J 8.0 Hz), 7.83 (1H, d, J 8.0 Hz), 8.22 (2H, t, J 8.0 Hz) and 8.95 (2H, br s)

1-Methyl-1H-pyrazole-5-methanamine

NMR δ$_H$ (400 MHz, DMSO) 3.80 (3H, s), 3.99 (2H, s), 6.09 (2H, s), 6.27 (1H, d, J 1.5 Hz) and 7.35 (1H, d, J 1.5 Hz)

Method J

2-Amino-6-(2-furyl)-N-(5-indolylmethyl)pyrimidine-4-carboxamide (Example 35)

A mixture consisting of 2-amino-6-(2-furyl)pyrimidine-4-carboxylic acid (206 mg, 1.0 mmol), indole-5-methanamine (146 mg, 1.0 mmol), polymer supported carbodiimide (Argonaut Technologies, loading 1.38 mmol/g, 1.10 g, 1.5 mmol) and 1-hydroxybenzotriazole hydrate (203 mg, 1.5 mmol) in DMF (5 mL) was stirred at room temperature for 24 hr. The mixture was filtered through a pad of Celite, washing through with EtOAc. The filtrate was washed successively with H$_2$O (10 mL), 2-M Na$_2$CO$_3$ (2×10 mL) and H$_2$O (10 mL), dried (MgSO$_4$) and concentrated in vacuo. The resulting oil was dissolved in MeOH (1.0 mL), added dropwise with stirring to H$_2$O (2 mL) and the resulting precipitate filtered to give the title compound (198 mg, 59%) as a cream solid.

Method K

2-Amino-N-benzyl-6-(2-furyl)pyrimidine-4-carboxamide (Example 42)

A solution of 2-amino-6-(2-furyl)pyrimidine-4-carboxylic acid (103 mg, 0.5 mmol) in DMF (2 mL) was treated with benzylamine (59 mg, 0.55 mmol), EDCl (104 mg, 0.54 mmol) and 4-dimethylaminopyridine (66 mg, 0.54 mmol), stirred at room temperature for 17 h, poured into water (25 mL) and extracted with EtOAc (2×25 mL). The combined organic phase was washed with water (25 mL), dried (MgSO$_4$), concentrated in vacuo and purified by chromatography [SiO$_2$; isopropyl ether:EtOAc, (100:0-0:100)] to give the title compound (52 mg, 40%) as an off-white solid.

Method L

2-Bromomethyl-6-(triphenylmethoxymethyl)pyridine

A solution of 6-(triphenylmethoxymethyl)pyridine-2-methanol (16.8 g, 44 mmol) in $CH_2Cl_2$ at 0° C. was treated with triphenylphosphine (17.3 g, 66 mmol) and carbon tetrabromide (17.5 g, 52.8 mmol), stirred at 0° C. for 2.5 h then concentrated in vacuo to approximately a quarter of the original volume. The resulting solution was filtered through a pad of silica, washed with hexane:EtOAc (1:1) and the filtrate concentrated in vacuo to give the title compound (16.8 g, 86%) as a cream solid; NMR $\delta_H$(400 MHz, DMSO) 4.14 (2H, s), 4.61 (2H, s), 7.27-7.48 (16H, m), 7.68 (1H, d, J 7.5 Hz) and 7.90 (1H, t, J 7.5 Hz); $R_f$(Hexane:EtOAc (2:1))=0.84

The following novel bromides were also synthesised by Method L from the appropriate alcohol.

6-Bromomethyl-3-methylpyridine-2-carbonitrile

NMR $\delta_H$(400 MHz, DMSO) 2.57 (3H, s), 4.52 (2H, s) 7.58 (1H, d, J 8.5 Hz) and 7.68 (1H, d, J 8.5 Hz); M/Z 211 and 213 (M+H)$^+$ Method M 2-(Azidomethyl)-6-(triphenylmethoxymethyl)pyridine A solution of 2-bromomethyl-6-(triphenylmethoxymethyl)pyridine (3.04 g, 6.84 mmol) in DMF (25 mL) was treated with sodium azide (650 mg, 10 mmol) and stirred at room temperature for 20 h. The reaction was poured into water (100 mL), extracted with EtOAc (2×50 mL) and the combined organic phase was washed with brine (25 mL), dried ($MgSO_4$) and concentrated in vacuo to give the product (2.75 g, 99%) as a yellow oil; IR $\nu_{max}$ (Film)/cm$^{-1}$ 3060, 2103, 1679, 1594, 1448, 1096 and 706; NMR $\delta_H$ (400 MHz, $CDCl_3$) 4.36 (2H, s), 4.39 (2H, s), 7.20-7.33 (10H, m), 7.49-7.52 (6H, m) and 7.72-7.80 (2H, m)

Method N 6-(Triphenylmethoxymethyl)pyridine-2-methanamine

A solution of 2-(azidomethyl)-6-(triphenylmethoxymethyl)pyridine (2.78 g, 6.8 mmol) in THF (25 mL) was treated with triphenylphosphine (1.96 g, 7.5 mmol), stirred at room temperature for 3 h, treated with water (184 µl, 10.2 mmol), stirred at room temperature for a further 7 days and concentrated in vacuo. The resulting oil was purified by chromatography [$SiO_2$; EtOAc:MeOH:$NH_3$ (1:0:0) to (9:1:0.2)] to give the title compound (2.33 g, 90%) as a yellow oil; NMR $\delta_H$ (400 MHz, $CDCl_3$) 1.74 (2H, s), 3.90 (2H, s), 4.34 (2H, s), 7.14-7.33 (10H, m), 7.50-7.52 (6H, m) and 7.65-7.74 (2H, m); M/Z 381 (M+H)$^+$ Method O 2-Amino-6-(2-furyl)-N-(6-hydroxymethylpyridin-2-ylmethyl)pyrimidine-4-carboxamide (Example 33)

A solution of 2-amino-6-(2-furyl)-N-(6-(triphenylmethoxymethyl)pyridin-2-ylmethyl)pyrimidine-4-carboxamide (3.41 g, 6 mmol) in MeOH (50 mL) was treated with 4-M HCl in dioxane (7.5 mL, 30 mmol), stirred at room temperature for 20 h and concentrated in vacuo. The residue was diluted with water (50 mL) basified with 5-M NaOH, extracted with EtOAc (2×25 mL) and the combined organic phase washed with brine (25 mL), dried ($MgSO_4$) and concentrated in vacuo to give the title compound (1.19 g, 61%) as a cream solid.

Method P

2-Amino-6-(2-furyl)-N-(1H-imidazol-2-ylmethyl)pyrimidine-4-carboxamide (Example 91)

A solution of 2-amino-6-(2-furyl)-N-(1-(2-(trimethylsilyl)ethoxy)methyl-1H-imidazol-2-ylmethyl)pyrimidine-4-carboxamide (340 mg, 0.82 mmol) in MeOH (20 mL) at 0° C. was treated dropwise with conc HCl (4 mL), stirred at 80° C. for 1 h, cooled to room temperature and concentrated in vacuo. The residue was triturated with diethyl ether and the resulting dihydrochloride salt (230 mg, 78%) filtered, washed with diethyl ether, stirred with saturated aqueous $NaHCO_3$ (5 mL), filtered and washed with water to give the title compound (165 mg, 71%) as a yellow solid.

Method Q

2-Amino-6-(2-furyl)-N-(1-methyl-1H-imidazol-2-ylmethyl)pyrimidine-4-carboxamide (Example 34)

A solution of 2-amino-6-(2-furyl)-N-(1H-imidazol-2-ylmethyl)pyrimidine-4-carboxamide (300 mg, 1.06 mmol) in DMF (15 mL) at room temperature was treated with NaH (44 mg, 1.11 mmol), stirred for 20 min, treated with MeI (99 µl, 1.58 mmol) and stirred at room temperature for 16 h. The mixture was poured into water (30 mL), extracted with EtOAc (3×10 mL) and the combined organic phase was dried ($MgSO_4$), concentrated in vacuo and purified by chromatography [$SiO_2$; EtOAc] to give the title compound (180 mg, 57%) as a yellow solid.

Method R

6-Hydroxymethyl-3-methylpyridine-2-carbonitrile

A solution of 3,6-dimethylpyridine-2-carbonitrile (4.44 g, 30.0 mmol) and conc. $H_2SO_4$ (2 drops) in acetic anhydride (30 mL) was stirred at 100° C. for 16 h, cooled to room temperature, poured into water (100 mL) and basified to pH 8 with saturated aqueous $NaHCO_3$. The mixture was extracted with EtOAc (3×25 mL) and the combined organic phase dried ($MgSO_4$) and concentrated in vacuo. The residue was treated with MeOH (100 mL), water (40 mL) and $K_2CO_3$ (8.8 g), stirred at room temperature for 1 h, concentrated in vacuo and partitioned between EtOAc and water. The organic phase was dried ($MgSO_4$) and concentrated in vacuo to give the title compound (2.4 g, 51%) as a yellow oil; NMR $\delta_H$ (400 MHz, $CDCl_3$) 2.57 (3H, s), 4.78 (2H, s), 7.42 (1H, d, J 8.5 Hz) and 7.67 (1H, d, J 8.5 Hz); M/Z 149 (M+H)$^+$ Method S N-(6-Cyano-5-methylpyridine-2-ylmethyl)-N-methylacetamide A solution of N-methylacetamide (416 mg, 5.69 mmol) in THF (15 mL) at room temperature was treated with NaH (228 mg, 5.69 mmol), stirred for 15 min, treated with 6-bromomethyl-3-methylpyridine-2-carbonitrile (1.0 g, 4.74 mmol), stirred for 16 h, poured into water (50 mL), extracted with EtOAc (3×15 mL) and the combined organic phase was dried ($MgSO_4$) and concentrated in vacuo to give the title compound (665 mg, 69%) as a yellow oil; NMR $\delta_H$ (400 MHz, CDCl$_3$) 2.15 (3H, s), 2.53 (3H, s), 3.09 (3H, s), 4.65 (2H, s), 7.43 (1H, d, J 8.0 Hz) and 7.61 (1H, d, J 8.0 Hz); M/Z 204 (M+H)$^+$ Method T 6-(2-Amino-6-(2-furyl)pyrimidine-4-carboxyamidomethyl)pyridin-2-ylmethyl isopropylcarbamate (Example 41)

A solution of 2-amino-6-(2-furyl)-N-(6-hydroxymethylpyridin-2-ylmethyl)pyrimidine-4-carboxamide (200 mg, 0.61 mmol) in DMF (10 mL) was treated with iso-propyl isocyanate (86 µl, 0.915 mmol) and triethylamine (one drop) and shaken at 90° C. for 20 h. The incomplete reaction was treated with iso-propyl isocyanate (57 µl, 0.61 mmol) and shaken at 90° C. for a further 20 h, concentrated in vacuo and purified by preparative HPLC to give the title compound (70 mg, 28%) as a beige solid.

Method U 6-(2-Amino-6-(2-furyl)pyrimidine-4-carboxyamidomethyl)pyridin-2-ylmethyl dimethylcarbamate (Example 54)

A stirred solution of 2-amino-6-(2-furyl)-N-(6-hydroxymethylpyridin-2-ylmethyl)pyrimidine-4-carboxamide (50 mg, 0.15 mmol) in DMF (5 mL) at 0° C. was treated with NaH (6 mg, 0.15 mmol), stirred for 5 min, treated with dimethylcarbamyl chloride (14 µl, 0.15 mmol), stirred at room temperature for 1 h, diluted with water and the resulting precipitate filtered to give the title compound (35 mg, 58%) as a cream solid.

Method V

2-Amino-N-(4-amino-3-methylbenzyl)-6-(2-furyl)pyrimidine-4-carboxamide hydrochloride (Example 84)

A suspension of 2-amino-6-(2-furyl)-N-(3-methyl-4-nitrobenzyl)pyrimidine-4-carboxamide (101 mg, 0.29 mmol) in EtOH (3 mL) at 50° C. was treated dropwise with a freshly prepared solution of SnCl$_2$ dihydrate (193 mg, 0.857 mmol) in concentrated HCl (0.7 mL) and heated at 70° C. for 24 h, cooled, filtered and the resulting solid washed with a little EtOH. The resulting HCl salt was slurried with 2.5-M NaOH solution, filtered and the solid dissolved in hot THF, filtered through a pad of silica, and the filtrate concentrated in vacuo to give the free base as a yellow oil. The oil was dissolved in MeOH, treated with HCl solution (4-M in dioxane, 0.5 mL), stirred for 24 h and filtered to give the title compound (31 mg, 35%) as a grey solid.

Method W

2-Amino-N-(6-amino-2-pyridylmethyl)-6-(2-furyl)pyrimidine-4-carboxamide (Example 95)

A mixture of 2-amino-N-(6-bromo-2-pyridylmethyl)-6-(2-furyl)pyrimidine-4-carboxamide (350 mg, 0.93 mmol) and copper(I)oxide (6.7 mg, 0.046 mmol) in 4-M NH$_4$OH in ethylene glycol (20.23 ml, 80.92 mmol) was heated in a sealed tube at 90° C. for 20 h, cooled, poured into water (100 mL) and extracted with EtOAc (2×25 mL). The combined organic phase was washed with brine (10 mL), dried (MgSO$_4$), concentrated in vacuo and purified by chromatography [SiO$_2$; Hexane:EtOAc (1:4)-(0:1)] to give the title compound (65 mg, 22%) as a cream solid.

Method X

2-Amino-6-(2-furyl)-5-methylpyrimidine-4-carbonitrile

A solution of 4-chloro-6-(2-furyl)-5-methylpyrimidine-2-amine (80 mg, 0.38 mmol) in acetonitrile (4 mL) was treated with polymer supported cyamide (0.636 mg, 1.91 mmol), stirred at 140° C. in the microwave for 30 min, filtered to remove the resin and the filter cake washed with acetonitrile. The filtrate was concentrated in vacuo to give the title compound (50 mg, 65%) as off-white solid; NMR $\delta_H$ (400 MHz, DMSO) 2.48 (3H, s), 6.75 (1H, dd, J 1.7, 3.5 Hz), 7.04 (2H br s), 7.28 (1H, dd, J 0.7, 3.5 Hz) and 8.00 (1H, dd, J 0.7, 1.7 Hz); M/Z 201 (M=H)$^+$; HPLC 1.1 min. (50/80).

Method Y

4-Hydroxy-6-(2-thiazolyl)pyrimidine-2-amine

Guanidine carbonate (3.48 g, 19.32 mmol) was suspended in EtOH (100 mL) and toluene (20 mL) and 50 mL of the solvent was distilled off using a Dean & Stark apparatus. The suspension was cooled to 40° C., treated with a solution of ethyl D-oxo-2-thiazolepropionate (7.7 g, 38.65 mmol) in EtOH (20 mL), refluxed for 40 h, cooled, treated with water (50 mL) and refluxed for 30 min. The suspension was cooled to 0° C., treated with a solution of conc. HCl (4 mL) in water (40 mL), stirred at 0° C. for 30 min and the resulting precipitate filtered, washed with water (2×25 mL) and MeCN (2×25 mL) and air dried to give the title compound (2.7 g, 36%) as a yellow solid; IR $\nu_{max}$ (DR)/cm$^{-1}$ 3188 br, 1664, 1609, 1460, 1437, 1376 and 1245; NMR $\delta_H$ (400 MHz, DMSO) 6.27 (1H, s), 6.79 (2H, br s), 7.90 (1H, d, J 3.2 Hz) and 7.98 (1H, d, J 3.2 Hz)

The following novel compound was also synthesised by Method Y from ethyl 4-methyl-β-oxo-2-thiazolepropionate.

4-Hydroxy-6-(4-methylthiazol-2-yl)pyrimidine-2-amine

NMR $\delta_H$ (400 MHz, DMSO) 2.42 (3H, s), 6.21 (1H, s), 6.75 (2H, br s), 7.45 (1H, s) and 10.90 (1H, br s); M/Z 209 (M+H)$^+$; Anal. Calc for C$_8$H$_8$N$_4$OS: C, 46.14; H, 3.87; N, 26.89. Found: C, 46.04; H, 3.91; N, 26.53.

Method Z

4-Chloro-6-(2-thiazolyl)pyrimidine-2-amine

A suspension of the 4-hydroxy-6-(2-thiazolyl)pyrimidine-2-amine (2.64 g, 13.6 mmol) in POCl$_3$ (30 mL) was heated at 120° C. for 3 h, cooled and concentrated in vacuo. The resulting brown solid was added to ice/water (200 g), basified with NH$_4$OH (8 mL), filtered and purified by chromatography [SiO$_2$; EtOAc:isohexane (2:3-1:0)] to give the title compound (1.73 g, 60%) as a pale yellow solid; NMR $\delta_H$ (400 MHz, DMSO) 7.22 (1H, s), 7.40 (2H, br s), 8.01 (1H, d, J 3.2 Hz) and 8.07 (1H, d, J 3.2 Hz); M/Z 213, 215 (M+H)$^+$ Method AA Ethyl 4-methyl-β-oxo-2-thiazolepropionate NaH (60% in oil, 1.34 g, 33.5 mmol) was washed with isohexane (2×14 mL), suspended in toluene (25 mL), treated with diethyl carbonate (4.7 mL, 4.6 g, 38.8 mmol), heated to 80° C., treated dropwise over 20 min with a solution of 2-acetyl-4-methylthiazole (2.72 g, 19.2 mmol) in toluene (5 mL) and stirred at 80° C. for 2 h. The mixture was cooled to 0° C., treated dropwise with HOAc (4.65 mL, 4.9 g, 81 mmol) followed by ice (25 g) and water (50 mL) and stirred for 30 min. The aqueous phase was extracted with toluene (50 mL), the combined organic phase was washed with water (50 mL), dried (MgSO$_4$) and concentrated in vacuo to give the crude product (3 g, 74%) as a dark red oil, used in the next step without further purification; NMR $\delta_H$ (400 MHz, CDCl$_3$) 1.26 (3H, t, J 7.2 Hz), 2.92 (3H, s), 4.14 (2H, s), 4.18-4.25 (2H, m) and 7.31 (1H, s).

Method AB

4-Chloro-6-(5-methyl-2-furyl)pyrimidine-2-amine

A solution of 2-methylfuran (11 mL, 122 mmol) and N,N,N',N'-tetramethylethylenediamine (18.4 mL, 122 mmol) in anhydrous THF (500 mL) at −78° C. under nitrogen was treated with n-butyl lithium (48.8 mL, 122 mmol), stirred at −78° C. for 20 min, warmed to 0° C. for 30 min and then warmed to room temperature for 15 min. The reaction was cooled to −78° C., treated with trimethyl borate (27.4 ml, 244 mmol), warmed to room temperature, treated with MeOH (100 mL) and water (5 mL), stirred at room temperature for 30 min and concentrated in vacuo. The residue was treated with MeOH (3×100 mL) and concentrated in vacuo after each addition to give the boronic ester as an orange gum. A solution of 2-amino-4,6-dichloropyrimidine (20 g, 122 mmol) in THF (1 L) was treated with saturated aqueous NaHCO$_3$ (250 mL), a solution of the above boronic ester (122 mmol) in THF (50 mL) and tetrakis(triphenylphosphine)palladium (6.93 g, 6 mmol), stirred at 70° C. for 20 h, cooled, extracted with EtOAc (2×100 mL), washed with water (200 mL) and the combined organic phase dried (MgSO$_4$) and concentrated in vacuo to give the product (24.5 g, 96%) as a yellow solid; NMR $\delta_H$ (400 MHz, DMSO) 2.37 (3H, s), 6.32-6.33 (1H, m), 6.89 (1H, s), 7.11 (2H, s) and 7.18-7.19 (1H, m).

Method AC 6-(Tert-butyldimethylsilyloxymethyl)pyridine-2-methanamine

A solution of 6-aminomethypyridine-2-methanol (5 g, 36.2 mmol) in anhydrous DMF (25 mL) at 0° C. was treated with tert-butyldimethylsilyl chloride (5.728 g, 38 mmol) and imidazole (2.584 g, 38 mmol), stirred at room temperature for 20 h, poured into 1.5-M aqueous NaOH (100 mL) and extracted with EtOAc (3×20 mL). The combined organic phase was washed with water (4×10 mL), brine (2×20 mL), dried (MgSO$_4$) and concentrated in vacuo to give the title compound as a yellow oil; NMR $\delta_H$ (400 MHz, CDCl$_3$) 0.82 (9H, s), 0.87 (6H, s), 1.81 (2H, s), 3.84 (2H, s), 4.73 (2H, s), 7.03 (1H, d, J 8.0 Hz), 7.28 (1H, d, J 7.5 Hz) and 7.57 (1H, t, J 8.0 Hz); M/Z 253 (M+H)$^+$ Method AD 2-Amino-6-(5-methyl-2-furyl)-N-(6-hydroxymethylpyridin-2-ylmethyl)pyrimidine-4-carboxamide (Example 133)

A solution of 2-amino-6-(5-methyl-2-furyl)-N-(6-(tert-butyldimethylsilyloxymethyl)pyridin-2-ylmethyl)pyrimidine-4-carboxamide (614 mg, 1.36 mmol) in acetic acid (9 mL) water (3 mL) and THF (3 mL) was stirred at room temperature for 4 days, neutralised with saturated aqueous NaHCO$_3$ and extracted with EtOAc. The combined organic phase was dried (MgSO$_4$), concentrated in vacuo, and the resulting solid triturated with MeOH and filtered to give the title compound (536 mg, 49%) as a cream solid.

Method AE

2-Amino-5-chloro-N-(6-methoxymethyl-2-pyridylmethyl)-6-(5-methyl-2-furyl)pyrimidine-4-carboxamide (Example 116)

A solution of 2-amino-N-(6-methoxymethyl-2-pyridylmethyl)-6-(5-methyl-2-furyl)pyrimidine-4-carboxamide (50 mg, 0.142 mmol) in acetic acid (10 mL) at room temperature was treated with N-chlorosuccinimide (24 mg, 0.156 mmol), stirred at 100° C. for 2 h, cooled to room temperature, concentrated in vacuo and partitioned between EtOAc (20 mL) and saturated aqueous NaHCO$_3$ (20 mL). The organic phase was dried (MgSO$_4$), concentrated in vacuo and the resulting solid was triturated with diethyl ether and filtered to give the title compound (30 mg, 54%) as a beige solid.

Method AF

2-Amino-5-bromo-N-(6-methoxymethyl-2-pyridylmethyl)-6-(5-methyl-2-furyl)pyrimidine-4-carboxamide (Example 117)

A solution of 2-amino-N-(6-methoxymethyl-2-pyridylmethyl)-6-(5-methyl-2-furyl)pyrimidine-4-carboxamide (50 mg, 0.142 mmol) in acetic acid (10 mL) at room temperature was treated with N-bromosuccinimide (28 mg, 0.156 mmol), stirred for 2 h, concentrated in vacuo and partitioned between EtOAc (20 mL) and saturated aqueous NaHCO$_3$ (20 mL). The organic phase was dried (MgSO$_4$), concentrated in vacuo and the resulting solid was triturated with diethyl ether and filtered to give the title compound (50 mg, 82%) as a beige solid.

Method AG 2-(Isopropoxymethyl)pyridine-N-oxide

A stirred solution of 2-isopropoxymethylpyridine (18.4 g, 0.121 mol) in dichloromethane (200 mL) at room temperature was treated portionwise with meta-chloroperoxybenzoic acid (42.1 g, 0.121 mol), stirred for 3 h, poured into CHCl$_3$ (450 mL) and washed with 2.5-M aqueous NaOH solution (2×250 mL). The organic phase was dried (MgSO$_4$) and concentrated in vacuo to give the title compound as a pale yellow oil; NMR $\delta_H$ (400 MHz, CDCl$_3$), 1.19-1.21 (6H, d, J=6 Hz), 3.71-3.80 (1H, sept, J 6.5 Hz), 4.58 (2H, s), 7.37 (2H, m), 7.47-7.49 (1H, d, J 7 Hz) and 8.25-8.27 (1H, d, J 7.5 Hz)

Method AH 6-(Isopropoxymethyl)pyridine-2-carbonitrile

A stirred solution of 2-(isopropoxymethyl)pyridine-N-oxide (17.8 g, 0.11 mol) in dichloromethane (200 mL) at room temperature was treated with trimethylsilyl cyanide (17.65 mL, 0.132 mol) and dimethylcarbamyl chloride (12.18 mL, 0.132 mol), heated to 40° C. for 18 h, quenched with 2-M aqueous Na$_2$CO$_3$ solution (400 mL) and stirred for 2 h. The mixture was extracted with dichloromethane (2×200 mL), dried (MgSO$_4$) and concentrated in vacuo to give the title compound as an orange oil; NMR $\delta_H$ (400 MHz, CDCl$_3$) 1.17-1.18 (6H, d, J 6 Hz), 3.67-3.76 (1H, sept J 6 Hz), 4.58

(2H, s), 7.74-7.76 (1H, d, J 8 Hz), 7.92-7.94 (1H, d, J 7.5 Hz) and 8.04-8.08 (1H, t, J 7.5 Hz)

Method AI

4-Chloro-N-methyl-6-(5-methylfuran-2-yl)pyrimidine-2-amine

A solution of 2,4-dichloro-6-(5-methylfuran-2-yl)pyrimidine (0.70 g, 3.07 mmol) in MeOH (5 mL) was treated with 2-M methylamine in EtOH (2 mL, 4 mmol), heated at 80° C. for 30 min, cooled, concentrated in vacuo and purified by chromatography [$SiO_2$; hexane:EtOAc (100:0-90:10)] to give the title compound (0.17 g, 22%) as a white solid; NMR $\delta_H$ (400 MHz, $CD_3OD$) 2.38 (3H, s), 2.93 (3H, s), 6.22-6.23 (1H, m), 6.83 (1H, s) and 7.12-7.13 (1H, m); M/Z 224, 226 $(M+H)^+$ Method AJ

2-Dimethylamino-6(5-methylfuran-2-yl)pyrimidine-4-carboxylic acid lithium salt A mixture of 2-dimethylamino-6-(5-methylfuran-2-yl)pyrimidine-4-carbonitrile (0.68 g, 2.98 mmol) in 6-M HCl (40 mL) and THF (10 mL) was refluxed for 6 h, cooled, concentrated in vacuo and the residue subjected to ion-exchange column chromatography (Isolute® Flash SCX-2; DCM; MeOH then 1-M $NH_3$:MeOH). The resulting mixture of methyl ester and carboxylic acid (0.42 g) was treated with MeOH (15 mL), water (15 mL) and LiOH (72 mg, 1.81 mmol), stirred at room temperature for 1 h and concentrated in vacuo to give the title compound (0.48 g, 98%) as a white solid: NMR $\delta_H$ (400 MHz, $CD_3OD$) 2.38 (3H, s), 3.23 (6H, s), 6.19-6.20 (1H, m), 7.08-7.09 (1H, m) and 7.31 (1H, s); M/Z 248 $(M+H)^+$ Method AK

2-Amino-6-phenylpyrimidine-4-carboxylic acid

A solution of methyl 2-amino-6-chloropyrimidine-4-carboxylate (0.2 g, 1.07 mmol) and phenylboronic acid (0.16 g, 1.3 mmol) in THF (10 mL) was treated with saturated aqueous $NaHCO_3$ (1.6 mL). Nitrogen was bubbled through the solution for 5 min then tetrakis(triphenylphosphine)palladium(0) (0.04 g) was added and the mixture refluxed under nitrogen overnight. The mixture was treated with aqueous LiOH (1-M, 1 mL), heated at 90° C. for 2 h, concentrated in vacuo and partitioned between ethyl acetate and water. The aqueous layer was acidified to pH 1 with 2-N HCl, the resulting suspension centrifuged, the liquors decanted and the resulting solid dried to give the title compound (0.17 g, 72%) as a white powder which was used directly in the next step without further purification; M/Z 216 $(M+H)^+$; retention time 1.60 min (Method AM).

The following novel intermediates were also synthesized by Method AK from methyl 2-amino-6-chloropyrimidine-4-carboxylate and the appropriate arylboronic acid.

2-Amino-6-(2-methylphenyl)pyrimidine-4-carboxylic acid

M/Z 230 $(M+H)^+$; retention time 1.69 min (Method AM).

2-Amino-6-(3-methylphenyl)pyrimidine-4-carboxylic acid

M/Z 230 $(M+H)^+$; retention time 1.77 min (Method AM).

2-Amino-6-(4-methylphenyl)pyrimidine-4-carboxylic acid

M/Z 230 $(M+H)^+$; retention time 1.75 min (Method AM).

2-Amino-6-(3-methoxyphenyl)pyrimidine-4-carboxylic acid

M/Z 246 $(M+H)^+$; retention time 1.69 min (Method AM).

2-Amino-6-(3-cyanophenyl)pyrimidine-4-carboxylic acid

M/Z 241 $(M+H)^+$; retention time 1.64 min (Method AM).

Method AL

General Method for Preparative LC-MS

Preparative LC-MS was performed at ambient temperature on a Waters FractionLynx MS autopurification system using a Luna 5 μm, C18(2), 100 mm×21.2 mm i.d. column from Phenomenex. Solvent A: water+0.08% v/v formic acid, solvent B: 95% methanol-water+0.08% v/v formic acid, flow rate: 20 ml $min^{-1}$. The instrument incorporated a photo diode array detector (210-400 nm) and a MicroMass ZQ mass spectrometer. The ionisation method was positive ion electrospray and the molecular weight scan range was 150-1000. Collection was triggered by detection of the selected mass ion.

Method AM

General Method for Analytical LC-MS

| HPLC: | HP1100 |
| --- | --- |
| Column: | Luna 3 μm, C18(2), 30 mm × 4.6 mm i.d. from Phenomenex |
| Temperature: | 22° C. |
| Solvents: | A - Water + 10 mmol $NH_4OAc$ + 0.08% (v/v) formic acid |
| | B - 95% Acetonitrile/5% Solvent A + 0.08% (v/v) formic acid |
| Flow rate: | 2 ml/min |

| Gradient Total acquisition time is 3.75 minutes | | | |
| --- | --- | --- | --- |
| Time (mins) | % Solvent A | % Solvent B | Flow (ml/min) |
| 0 | 95 | 5 | 2 |
| 0.25 | 95 | 5 | 2 |
| 2.50 | 5 | 95 | 2 |
| 2.55 | 5 | 95 | 3 |
| 3.60 | 5 | 95 | 3 |
| 3.65 | 5 | 95 | 3 |
| 3.70 | 5 | 95 | 2 |
| 3.75 | 95 | 5 | 2 |

| Detection: | UV detection at 230 nm, 254 nm and 270 nm |
| --- | --- |
| Mass Spec: | HP1100 MSD, Series A |
| | Ionisation is positive or negative ion electrospray |
| | Molecular weight scan range is 120-1000 |

Results for observed molecular ions and HPLC retention times are given.

Method AN

General Method for Analytical HPLC

HPLC is carried out using the following conditions: Column. Waters Xterra RP 18 (50×4.6 mm); Particle size 5 µM; Mobile phase MeOH: 10 mM aq NH$_4$OAc (pH 7 buffer); Gradient 50:50 isocratic for 1 min. then linear gradient 50:50 to 80:20 over 5 min. then 80:20 isocratic for 3 min.; Flow rate 2.0 mL/min.; Detection wavelength λ=230 nM. Retention times are provided in Table 2.

Alternatively HPLC is carried out using the following conditions: Column. Supelcosil ABZ$^+$ (170×4.6 mm), particle size 5 µM, mobile phase MeOH: 10 mM aq NH$_4$OAc (80:20), (80:50), (70:30), (60:40) or (50:20) (specified in Table 2), flow rate 1.0 mL/min., detection wavelength λ=230 nM. Retention times and mobile phase ratio are provided in Table 2.

Method AO

General Method for Analytical TLC

Analytical tlc. Is carried out using Merck TLC glass plates coated with silica gel 60 F$_{254}$. R$_f$ values are quoted relative to the solvent front for the given solvent.

TABLE 2

| Example | Method | Yield (%) | Physical Data |
|---|---|---|---|
| 1 | D | 26 | Mp 200.0-205.9° C.; IR v$_{max}$ (DR)/cm$^{-1}$ 3374, 3209, 2107, 1676, 1636, 1541, 1489 and 1232; NMR δ$_H$ (400 MHz, DMSO) 4.55(2H, d, J 6.0 Hz), 6.71(1H, s), 6.90(2H, s), 7.10-7.49(6H, m), 7.94(1H, s) and 8.79(1H, t, J 5.5 Hz); LC 3.7 min. (50/80) |
| 2 | D | 23 | IR v$_{max}$ (DR)/cm$^{-1}$ 3318, 3210, 1686, 1644, 1557, 1471 and 1215; NMR δ$_H$ (400 MHz, DMSO) 6.73(1H, s), 6.98(2H, s), 7.34(1H, s), 7.46(2H, s), 7.62(1H, s), 7.90-8.05(2H, m) and 10.53(1H, s); LC 5.8 min. (50/80) |
| 3 | D | 36 | Mp 229.2-234.5° C.; IR v$_{max}$ (DR)/cm$^{-1}$ 4004, 3465, 3368, 3204, 3091, 2930, 2832, 1675, 1592, 1354 and 1252; NMR δ$_H$ (400 MHz, DMSO) 3.74(3H, s), 4.47(2H, s), 6.71(1H, s), 6.72-7.10(5H, m), 7.18-7.36(2H, m), 7.41(1H, s), 7.94(1H, s) and 8.78(1H, s); LC 3.4 min. (50/80) |
| 4 | D | 4 | IR v$_{max}$ (DR)/cm$^{-1}$ 3329, 3193, 2936, 1633, 1539, 1471 and 1224; NMR δ$_H$ (400 MHz, DMSO) 2.93(3H, s), 2.97(3H, s), 6.67-6.70(1H, m), 6.86(2H, s), 6.90(1H, s), 7.24(1H, d, J 3.5 Hz) and 7.88-7.91(1H, m); LC 1.25 min. (50/80) |
| 5 | D | 13 | Mp 139.5-143.0° C.; IR v$_{max}$ (DR)/cm$^{-1}$ 3331, 3212, 2937, 2858, 1627, 1539, 1471, 1264 and 1216; NMR δ$_H$ (400 MHz, DMSO) 1.43-1.67(6H, m), 3.24-3.30(2H, m), 3.55(2H, t, J 5.5 Hz), 6.68-6.70(1H, m), 6.88(1H, s), 6.89(2H, s), 7.25(1H, dd, J 3.5, 1.0 Hz) and 7.89-7.91(1H, m); LC 1.1 min. (50/80) |
| 6 | D | 19 | IR v$_{max}$ (DR)/cm$^{-1}$ 3361, 3196, 2956, 2835, 1674, 1538 and 1248; NMR δ$_H$ (400 MHz, DMSO) 4.47(2H, d, J 6.5 Hz), 6.69-6.73(1H, m), 6.86-6.97(3H, m), 7.02(1H, d, J 7.5 Hz), 7.20(1H, dd, J 7.5, 2.0 Hz), 7.24-7.31(2H, m), 7.41(1H, s), 7.92-7.96(1H, m) and 8.56(1H, t, J 6.5 Hz); LC 4.5 min. (50/80) |
| 7 | D | 12 | IR v$_{max}$ (DR)/cm$^{-1}$ 3381, 3201, 2923, 1681, 1555, 1342 and 1255; NMR δ$_H$ (400 MHz, DMSO) 4.50(2H, d, J 6.0 Hz), 6.27-6.35(1H, m), 6.40(1H, s), 6.71(1H, s), 6.89(2H, s), 7.29(1H, d, J 3.5 Hz), 7.40(1H, s), 7.58(1H, s), 7.93(1H, s) and 8.63(1H, t, J 6.0 Hz); LC 1.8 min. (50/80) |
| 8 | D | 15 | Mp 218.0-219.8° C.; IR v$_{max}$ (DR)/cm$^{-1}$ 3443, 3193, 1698, 1599, 1486, 1322 and 1245; NMR δ$_H$ (400 MHz, DMSO) 6.68-6.72(1H, m), 6.84(2H, s), 7.27(1H, d, J 3.5 Hz), 7.39(1H, s), 7.72(2H, d, J 10.5 Hz) and 7.91-7.94(1H, m); LC 0.6 min. (50/80) |
| 9 | D | 37 | Mp 202.4-202.9° C.; IR v$_{max}$ (DR)/cm$^{-1}$ 3366, 3192, 2872, 1637, 1509, 1351 and 1218; NMR δ$_H$ (400 MHz, DMSO) 2.86(6H, s), 4.36(2H, d, J 6.0 Hz), 6.66-6.72(3H, m), 6.89(2H, s), 7.13-7.19(2H, m), 7.29(1H, dd, J 3.5, 1.0 Hz), 7.41(1H, s), 7.93-7.95(1H, m) and 8.52(1H, t, J 6.0 Hz); LC 3.1 min. (50/80) |
| 10 | D | 35 | Mp 108.2-117.4° C.; IR v$_{max}$ (DR)/cm$^{-1}$ 4005, 3336, 2929, 2101, 1633 and 1228; NMR δ$_H$ (400 MHz, DMSO) 3.38(3H, s), 4.51(2H, s), 4.59(2H, d, J 6.0 Hz), 6.70-6.73(1H, m), 7.24(1H, d, J 7.5 Hz), 7.29-7.33(2H, m), 7.43(1H, s), 7.79(1H, t, J 8.0 Hz), 7.93-7.95(1H, m) and 8.98(1H, t, J 6.0 Hz); LC 1.1 min. (50/80) |
| 11 | D | 35 | Mp 200.2-200.3° C.; IR v$_{max}$ (DR)/cm$^{-1}$ 3347, 1646, 1503 and 1246; NMR δ$_H$ (400 MHz, DMSO) 2.33(3H, s), 4.63(2H, d, J 5.0 Hz), 6.70-6.73(1H, m), 7.01(2H, s), 7.27(1H, dd, J 7.5, 4.5 Hz), 7.31(1H, d, J 3.5 Hz), 7.46(1H, s), 7.64(1H, dt, J 7.5, 1.0 Hz), 7.94-7.96(1H, m) and 8.41(1H, dd, J 4.5, 1.0 Hz); LC 1.5 min. (50/80) |
| 12 | D | 39 | IR v$_{max}$ (DR)/cm$^{-1}$ 3413, 3097, 2931, 1635, 1550 and 1261; NMR δ$_H$ (400 MHz, DMSO) 2.89(3H, s), 2.97(3H, s), 4.52(2H, d, J 6.0 Hz), 6.69-6.73(1H, m), 6.88(2H, s), 7.25-7.32(2H, m), 7.34(1H, s), 7.36-7.44(3H, m), 7.94(1H, s) and 8.92(1H, t, J 6.0 Hz); LC 0.9 min. (50/80) |
| 13 | D | 44 | Mp 209.1-209.2° C.; IR v$_{max}$ (DR)/cm$^{-1}$ 3380, 3107, 1681, 1651, 1514, 1485 and 1230; NMR δ$_H$ (400 MHz, DMSO) 4.62(2H, d, J 6.0 Hz), 6.68-6.75(1H, m), 6.94(2H, s), 7.26-7.33(2H, m), 7.35(1H, d, J 7.5 Hz), 7.43(1H, s), 7.78(1H, dt, J 7.5, 1.5 Hz), 7.94(1H, s), 8.54(1H, d, J 4.5 Hz) and 8.96(1H, t, J 6.0 Hz); LC 5.4 min. (20/50) |
| 14 | D | 41 | Mp 195.4-196.3° C.; IR v$_{max}$ (DR)/cm$^{-1}$ 3328, 2937, 1519, 1416, 1353 and 1217; NMR δ$_H$ (400 MHz, DMSO) 4.51(2H, d, J 6.5 Hz), 6.70-6.72(1H, m), 6.87(2H, s), 7.27-7.31(3H, m), 7.41(1H, s), 7.94(1H, |

TABLE 2-continued

| Example | Method | Yield (%) | Physical Data |
|---|---|---|---|
| | | | d, J 1.0 Hz), 8.48-8.52(2H, m) and 9.03(1H, t, J 6.0 Hz); LC 5.2 min. (20/50) |
| 15 | D | 46 | Mp 151.1-152.2° C.; IR $\nu_{max}$ (DR)/cm$^{-1}$ 3377, 3201, 2918, 1681, 1519, 1355 and 1221; NMR $\delta_H$ (400 MHz, DMSO) 2.31(3H, s), 4.49(2H, d, J 6.0 Hz), 6.70-6.72(1H, m), 6.91(2H, s), 7.14-7.21(3H, m), 7.22-7.27(1H, m), 7.30(1H, d, J 3.5 Hz), 7.42(1H, s), 7.93-7.95(1H, m) and 8.59(1H, t, J 6.0 Hz); LC 3.8 min. (50/80) |
| 16 | D | 50 | Mp 170.6-170.7° C.; IR $\nu_{max}$ (DR)/cm$^{-1}$ 3487, 3316, 2919, 1633, 1520 and 1333; NMR $\delta_H$ (400 MHz, DMSO) 4.57(2H, d, J 6.0 Hz), 6.70-6.72(1H, m), 6.87(2H, s), 7.30(1H, dd, J 3.5, 1.0 Hz), 7.41(1H, s), 7.55-7.66(3H, m), 7.69(1H, s), 7.93-7.95(1H, m) and 9.04(1H, t, J 6.5 Hz); LC 4.9 min. (50/80) |
| 17 | D | 38 | Mp 290.9-291.3° C.; IR $\nu_{max}$ (DR)/cm$^{-1}$ 3425, 3277, 1671, 1599, 1510, 1459, 1323 and 1202; NMR $\delta_H$ (400 MHz, DMSO) 4.74(2H, d, J 6.0 Hz), 6.70-6.74(1H, m), 6.95(2H, s), 7.11-7.19(2H, m), 7.31(1H, d, J 3.5 Hz), 7.42-7.60(3H, m), 7.95(1H, d, J 1.5 Hz), 8.92(1H, t, J 6.0 Hz) and 12.30(1H, s); LC 1.8 min. (50/80) |
| 18 | D | 35 | Mp 162.0-170.0° C.; IR $\nu_{max}$ (DR)/cm$^{-1}$ 3197, 2216, 1633, 1513, 1352 and 1219; NMR $\delta_H$ (400 MHz, DMSO) 4.51(2H, d, J 6.5 Hz), 6.69-6.73(1H, m), 6.86(2H, s), 7.29(1H, d, J 3.0 Hz), 7.36(1H, dd, J 7.5, 4.5 Hz), 7.40(1H, s), 7.73(1H, d, J 7.5 Hz), 7.94(1H, s), 8.47(1H, d, J 4.0 Hz), 8.56(1H, s) and 8.98(1H, t, J 6.0 Hz); LC 5.3 min. (20/50) |
| 19 | D | 13 | Mp 143.2-143.7° C.; IR $\nu_{max}$ (DR)/cm$^{-1}$ 3324, 3210, 2922, 1673, 1633, 1520, 1342 and 1249; NMR $\delta_H$ (400 MHz, DMSO) 2.29(3H, s), 4.45(2H, d, J 6.0 Hz), 6.68-6.74(1H, m), 6.88(2H, s), 7.04-7.17(3H, m), 7.22(1H, t, J 7.5 Hz), 7.29(1H, d, J 3.0 Hz), 7.42(1H, s), 7.94(1H, s) and 8.76(1H, t, J 6.0 Hz); LC 3.9 min. (50/80) |
| 20 | D | 14 | NMR $\delta_H$ (400 MHz, DMSO) 3.36(3H, s), 4.56(2H, s), 4.67(2H, d, J 5.5 Hz), 6.70-6.73(1H, m), 6.99(2H, s), 7.30(1H, dd, J 3.5, 1.0 Hz), 7.36(1H, dd, J 7.5, 5.0 Hz), 7.45(1H, s), 7.79(1H, dd, J 7.5, 1.5 Hz), 7.93-7.95(1H, m), 8.52(1H, dd, J 4.5, 2.0 Hz) and 8.99(1H, t, J 5.0 Hz); M/Z 340(M+H)$^+$; LC 1.2 min. (50/80) |
| 21 | D | 7 | IR $\nu_{max}$ (DR)/cm$^{-1}$ 3509, 3346, 2814, 2764, 1667, 1589, 1503, 1338 and 1239; NMR $\delta_H$ (400 MHz, DMSO) 2.19(6H, s), 3.49(2H, s), 4.75(2H, d, J 5.5 Hz), 6.70-6.72(1H, m), 6.94(2H, s), 7.29(1H, d, J 3.5 Hz), 7.33(1H, dd, J 7.0, 4.5 Hz), 7.44(1H, s), 7.70(1H, d, J 7.0 Hz), 7.93-7.96(1H, m), 8.49(1H, d, J 3.5 Hz) and 9.20(1H, t, J 5.0 Hz); LC 1.1 min. (50/80) |
| 22 | D | 34 | Mp 195.5-197.5° C.; IR $\nu_{max}$ (DR)/cm$^{-1}$ 3314, 2821, 1675, 1633, 1543, 1345, 1226 and 1114; NMR $\delta_H$ (400 MHz, DMSO) 2.39(4H, t, J 4.5 Hz), 3.55-3.59(6H, m), 4.78(2H, d, J 5.0 Hz), 6.70-6.73(1H, m), 6.97(2H, s), 7.30(1H, dd, J 3.5, 1.0 Hz), 7.33(1H, dd, J 7.5, 5.0 Hz), 7.45(1H, s), 7.72(1H, dd, J 7.5, 2.0 Hz), 7.94-7.96(1H, m), 8.49(1H, dd, J 4.5, 2.0 Hz) and 9.00(1H, t, J 5.0 Hz); LC 1.3 min. (50/80) |
| 23 | D | 28 | IR $\nu_{max}$ (DR)/cm$^{-1}$ 3353, 3207, 2975, 1643, 1502 and 1243; NMR $\delta_H$ (400 MHz, DMSO) 2.27(3H, s), 2.51(3H, s), 4.56(2H, d, J 4.5 Hz), 6.71-6.72(1H, m), 7.02(2H, s), 7.12(1H, d, J 8.0 Hz), 7.31(1H, dd, J 3.5, 1.0 Hz), 7.45(1H, s), 7.51(1H, d, J 7.5 Hz), 7.94-7.96(1H, m) and 9.11(1H, t, J 5.0 Hz); LC 2.1 min. (50/80) |
| 24 | D | 17 | IR $\nu_{max}$ (DR)/cm$^{-1}$ 3509, 3366, 2920, 1750, 1682, 1519, 1418, 1356 and 1229; NMR $\delta_H$ (400 MHz, DMSO) 4.60(2H, d, J 6.0 Hz), 6.70-6.73(1H, m), 6.94(2H, s), 7.17(1H, dd, J 5.0, 3.5 Hz), 7.30(1H, d, J 3.5 Hz), 7.43(2H, s), 7.66(1H, dd, J 3.5, 1.0 Hz), 7.72(1H, dd, J 5.0, 1.0 Hz), 7.94-7.97(1H, m) and 8.84(1H, t, J 6.0 Hz); LC 3.6 min. (50/80) |
| 25 | D | 15 | IR $\nu_{max}$ (DR)/cm$^{-1}$ 3354, 3191, 1678, 1635, 1514, 1328, 1256 and 1231; NMR $\delta_H$ (400 MHz, DMSO) 4.65(2H, d, J 6.0 Hz), 6.70-6.73(1H, m), 6.90(2H, s), 6.97(1H, dd, J 5.0, 3.5 Hz), 7.03-7.06(1H, m), 7.29-7.31(1H, m), 7.39-7.42(1H, m), 7.41(1H, s), 7.94-7.95(1H, m) and 8.88(1H, t, J 6.5 Hz); LC 1.9 min. (50/80) |
| 26 | D | 17 | IR $\nu_{max}$ (DR)/cm$^{-1}$ 3474, 3353, 3203, 1687, 1628, 1521, 1367 and 1217; NMR $\delta_H$ (400 MHz, DMSO) 4.66(2H, d, J 6.0 Hz), 6.70-6.73(1H m), 6.91(2H, s), 7.06(1H, d, J 4.0 Hz), 7.22-7.26(1H, m), 7.31(1H, dd, J 3.5, 1.0 Hz), 7.42(1H, s), 7.63(1H, d, J 4.0 Hz), 7.77-7.88(2H, m), 7.94-7.96(1H, m), 8.46-8.50(1H, m) and 8.97(1H, t, J 6.0 Hz); LC 2.7 min. (50/80) |
| 27 | D | 19 | IR $\nu_{max}$ (DR)/cm$^{-1}$ 3491, 3321, 1659, 1527, 1455 and 1318; NMR $\delta_H$ (400 MHz, DMSO) 2.29(3H, s), 4.42(2H, d, J 6.0 Hz), 6.28(1H, s), 6.70-6.73(1H, m), 6.89(2H, s), 7.30(1H, dd, J 3.5, 1.0 Hz), 7.40(1H, s), 7.94-7.96(1H, m) and 8.89(1H, t, J 6.0 Hz); LC 4.4 min. (50/80) |
| 28 | D | 17 | IR $\nu_{max}$ (DR)/cm$^{-1}$ 3460, 3319, 1679, 1520, 1398, 1360 and 1217; NMR $\delta_H$ (400 MHz, DMSO) 2.37(3H, s), 4.49(2H, d, J 6.0 Hz), 6.17(1H, s), 6.70-6.73(1H, m), 6.91(2H, s), 7.30(1H, d, J 3.5 Hz), 7.40(1H, s), 7.94-7.96(1H, m) and 8.89(1H, t, J 6.0 Hz); LC 1.0 min. (50/80) |
| 29 | D | 27 | Mp 178.0-178.1° C.; IR $\nu_{max}$ (DR)/cm$^{-1}$ 3317, 3211, 1635, 1543, 1466, 1360 and 1250; NMR $\delta_H$ (400 MHz, DMSO) 2.37(3H, s), 3.91(3H, s), 4.39(2H, d, J 6.0 Hz), 6.70-6.72(1H, m), 6.81(1H, d, J 7.5 Hz), |

TABLE 2-continued

| Example | Method | Yield (%) | Physical Data |
|---|---|---|---|
| | | | 6.93(2H, s), 7.30(1H, d, J 3.5 Hz), 7.40(1H, s), 7.43(1H, d, J 7.5 Hz), 7.93-7.95(1H, m) and 8.67(1H, t, J 6.0 Hz); LC 2.8 min. (50/80) |
| 30 | D | 14 | IR $\nu_{max}$ (DR)/cm$^{-1}$ 3335, 2862, 1674, 1515, 1339 and 1223; NMR $\delta_H$ (400 MHz, DMSO) 4.44(2H, d, J 6.0 Hz), 4.89(2H, s), 5.32(2H, s), 6.71-6.72(1H, m), 6.84-7.00(4H, m), 7.30(1H, dd, J 3.5, 1.0 Hz), 7.40(1H, s), 7.93-7.96(1H, m) and 8.75(1H, t, J 6.0 Hz); LC 2.9 min. (50/80) |
| 31 | M | 13 | NMR $\delta_H$ (400 MHz, DMSO) 2.44(3H, s), 4.46(2H, d, J 6.0 Hz), 6.70-6.71(1H, m), 6.86(2H, s), 7.21(1H, d, J 8.0 Hz), 7.28-7.29(1H, m), 7.39(1H, s), 7.62(1H, dd, J 8.0, 2.0 Hz), 7.93-7.94(1H, m), 8.41-8.42(1H, m) and 8.90(1H, t, J 6.0 Hz); M/Z 310(M+H)$^+$; LC 1.0 min. (50/80) |
| 32 | M | 65 | IR $\nu_{max}$ (DR)/cm$^{-1}$ 3359, 3184, 2917, 1633, 1538, 1471, 1224 and 747; NMR $\delta_H$ (400 MHz, DMSO) 2.95(2H, t, J 7.5 Hz) 3.60(2H, dd, J 6.5 Hz), 6.71(1H, dd, J 3.5, 1.5 Hz), 6.86(2H, br s), 6.96-7.01(1H, m), 7.04-7.10(1H, m), 7.19(1H, d, J 2.0 Hz), 7.29(1H, dd, J 3.5, 1.0 Hz), 7.34(1H, d, J 8.0 Hz), 7.41(1H, s), 7.60(1H, t, J 7.5 Hz), 7.94(1H, t, J 1.5 Hz), 8.46(1H, t, J 6.0 Hz) and 10.80(1H, br s); M/Z 348(M+H)$^+$; LC 3.4 min. (50/80) |
| 33 | O | 61 | Mp 183.4-183.6° C.; NMR $\delta_H$ (400 MHz, DMSO) 4.58(4H, d, J 5.5 Hz), 5.38-5.40(1H, m), 6.71-6.72(1H, m), 6.93(1H, s), 7.19(1H, d, J 8.0 Hz), 7.30(1H, d, J 3.5 Hz), 7.37(1H, d, J 8.0 Hz), 7.43(1H, s), 7.77(1H, t, J 8.0 Hz), 7.94-7.95(1H, m) and 8.96(1H, t, J 6.0 Hz); M/Z 327(M+H)$^+$; LC 4.8 min. (20/50) |
| 34 | Q | 57 | Mp 209.5-210.3° C.; IR $\nu_{max}$ (DR)/cm$^{-1}$ 3541, 3316, 3190, 1634, 1532 and 1470; NMR $\delta_H$ (400 MHz, DMSO) 3.64(3H, s) 4.56(1H, d, J 5.5 Hz), 6.71(1H, dd, J 3.5, 2.0 Hz), 6.83-6.82(1H, m), 6.97(2H, br s), 7.12-7.11(1H, m), 7.30(1H, d, J 3.5 Hz), 7.42(1H, s), 7.95-7.94(1H, m) and 8.64(1H, br t, J 5.5 Hz); M/Z 299(M+H)$^+$; LC 3.7 min. (20/50) |
| 35 | J | 59 | Mp 170.1-170.5° C.; IR $\nu_{max}$ (DR)/cm$^{-1}$ 3491, 3299, 1627, 1519, 1238 and 771; NMR $\delta_H$ (400 MHz, DMSO) 4.55(2H, d, J 6.0 Hz) 6.37-6.41(1H, m), 6.71(1H, dd, J 3.5, 1.5 Hz), 6.89(2H, br s), 7.08(1H, dd, J 8.5, 1.5 Hz), 7.29(1H, d, J 3.5 Hz), 7.32(1H, t, J 3.0 Hz), 7.35(1H, d, J 8.5 Hz), 7.43(1H, s), 7.49-7.52(1H, m), 7.93-7.95(1H, m), 8.59(1H, t, J 6.0 Hz) and 11.04(1H, br s); M/Z 334(M+H)$^+$; LC 2.7 min. (50/80) |
| 36 | J | 54 | Mp 155.9-156.0° C.; IR $\nu_{max}$ (DR)/cm$^{-1}$ 3325, 2917, 1594, 1517, 1237 and 747; NMR $\delta_H$ (400 MHz, DMSO) 2.13(3H, s) 2.29(3H, s), 4.53(3H, s), 6.71(1H, dd, J 3.5, 2.0 Hz), 6.90(2H, br s), 6.98(1H, dd, J 8.5, 2.0 Hz), 7.18(1H, d, J 8.5 Hz), 7.29(1H, d, J 3.5 Hz), 7.33(1H, br s), 7.43(1H, s), 7.92-7.95(1H, m), 8.52(1H, t, J 6.0 Hz) and 10.61(1H, br s); M/Z 362(M+H)$^+$; LC 4.9 min. (50/80) |
| 37 | J | 33 | Mp 191.8-192.2° C.; NMR $\delta_H$ (400 MHz, DMSO) 3.30(3H, s) 4.55(2H, d, J 6.0 Hz), 6.71(1H, dd, J 3.5, 1.5 Hz), 6.87(2H, br s), 7.30(1H, d, J 3.5 Hz), 7.37(1H, dd, J 8.5, 1.5 Hz), 7.41(1H, s), 7.42(1H, br s), 7.94(1H, d, J 2.5 Hz), 7.97(1H, d, J 8.5 Hz) and 9.04(1H, t, J 6.5 Hz); M/Z 354(M+H)$^+$; LC 3.8 min. (50/80) |
| 38 | J | | NMR $\delta_H$ (400 MHz, DMSO) 2:1 mixture of rotamers 2.06(1H, s), 2.18(2H, s), 2.29(1H, s), 2.30(2H, s), 2.88(2H, s), 2.96(1H, s), 4.57(0.66H, d, J 4.5 Hz), 4.60(1.33H, d, J 4.5 Hz), 4.63(0.66H, s), 4.70(1.33H, s), 6.71-6.72(1H, m), 7.00(0.66H, br s), 7.09(1.33H, br s), 7.14(0.33H, d, J 7.5 Hz), 7.24(0.66H, d, J 7.5 Hz), 7.31-7.32(1H, m), 7.45(0.33H, s), 7.46(0.66H, s), 7.61(0.33H, d, J 7.5 Hz), 7.66(0.66H, d, J 7.5 Hz), 7.94-7.95(1H, m), 9.34(0.66H, br t, J 4.5 Hz) and 9.37(0.33H, br t, J 4.5 Hz); M/Z 395(M+H)$^+$; LC 2.0 min. (50/80) |
| 39 | J | 6 | NMR $\delta_H$ (400 MHz, DMSO) 1:1 mixture of rotamers 2.89(1.5H, s), 2.98-3.05(3.5H, m), 3.65(1H, t, J 7.5 Hz), 3.76(1H, t, J 7.5 Hz), 6.46(0.5H, s), 6.69-6.71(1H, m), 6.83(0.5H, s), 6.89(1H, s), 6.93(1H, s), 7.12-7.15(0.5H, m), 7.18-7.20(1H, m), 7.24-7.29(1H, m), 7.35-7.39(0.5H, m), 7.63(0.5H, dt, J 7.5, 1.5 Hz), 7.75(0.5H, dt, J 7.5, 1.5 Hz), 7.92-7.94(1H, m), 8.31-8.33(0.5H, m) and 8.52-8.54(0.5H, m); M/Z 324(M+H)$^+$; LC 2.3 min. (20/50) |
| 40 | J | 60 | Mp 105.6-105.7° C.; IR $\nu_{max}$ (DR)/cm$^{-1}$ 3332, 2924, 1747, 1594, 1519, 1228 and 777; NMR $\delta_H$ (400 MHz, DMSO) 2.36(3H, s) 4.51(2H, d, J 6.0 Hz), 6.08(1H, s), 6.71(1H, dd, J 3.5, 2.0 Hz), 6.89(2H, br s), 6.98(1H, dd, J 8.0, 1.5 Hz), 7.22(1H, d, J 8.5 Hz), 7.29(1H, d, J 3.5 Hz), 7.35(1H, br s), 7.43(1H, s), 7.93-7.95(1H, m), 8.55(1H, t, J 6.0 Hz) and 10.85(1H, br s); M/Z 348(M+H)$^+$; LC 3.6 min. (50/80) |
| 41 | T | 28 | Mp 155.2-155.7° C.; NMR $\delta_H$ (400 MHz, DMSO) 1.07(6H, d, J 6.4 Hz), 3.62(1H, m), 4.59(2H, d, J 6.0 Hz), 5.08(2H, s), 6.71,(1H, dd, J 3.6, 1.6 Hz), 6.93(2H, br s), 7.24-7.27(3H, m), 7.30(1H, d, J 3.2 Hz), 7.42(1H, s), 7.80(1H, t, J 7.8 Hz), 7.94(1H, s) and 9.01(1H, t, J 6.0 Hz); M/Z 411(M+H)$^+$; LC 1.5 min. (50/80) |
| 42 | K | 35 | IR $\nu_{max}$ (DR)/cm$^{-1}$; NMR $\delta_H$ (400 MHz, DMSO) 4.50(2H, d, J 6.3 Hz), 6.71(1H, dd, J 1.6, 3.3 Hz), 6.88(2H, br s), 7.26-7.34(6H, m), 7.94(1H, m) and 8.81(1H, t, J 6.1 Hz); M/Z 295(M+H)$^+$; LC 2.3 min. (50/80) |

TABLE 2-continued

| Example | Method | Yield (%) | Physical Data |
|---|---|---|---|
| 43 | J | 71 | IR ν$_{max}$ (DR)/cm$^{-1}$; NMR δ$_H$ (400 MHz, DMSO) 3.92(2H, dt, J 1.6, 5.7 Hz), 5.15(2H, m), 5.90(1H, dq, J 5.2, 17.2 Hz), 6.71(1H, dd, J 1.9, 3.5 Hz), 6.89(2H, br s), 7.29(1H, m), 7.39(1H, s), 7.94(1H, m) and 8.46(1H, t, J 6.0 Hz); M/Z 245(M+H)$^+$; LC 1.0 min. (50/80) |
| 44 | J | 40 | IR ν$_{max}$ (DR)/cm$^{-1}$; NMR δ$_H$ (400 MHz, DMSO) 1.08(3H, d, J 6.2 Hz), 3.15(1H, m, J 5.6 Hz), 3.37(1H, dq, J 4.4, 6.6 Hz), 3.78(1H, m), 4.87(1H, d, J 4.7 Hz), 6.71(1H, dd, J 1.8, 3.5 Hz), 6.96(2H, br s), 7.29(1H, d, J 3.5 Hz), 7.41(1H, s), 7.94(1H, d, J 1.1 Hz) and 8.26(1H, t, J 1.9 Hz); M/Z 263(M+H)$^+$; LC 2.7 min. (20/50) |
| 45 | T | 31 | Mp 200.4-202.0° C.; NMR δ$_H$ (400 MHz, DMSO) 2.10(3H, s), 2.26(3H, s), 4.61(2H, d, J 5.5 Hz), 5.20(2H, m), 6.70-6.72(1H, m), 6.92(2H, s), 7.28-7.35(3H, m), 7.43(1H, s), 7.83(1H, t, J 7.5 Hz), 7.94-7.95(1H, m) and 9.01-9.05(2H, m); M/Z 464(M+H)$^+$; LC 1.3 min. (50/80) |
| 46 | J | 6 | Mp 148-148.4° C.; NMR δ$_H$ (400 MHz, DMSO) 2.31(2H, s), 3.38(3H, s), 4.54(2H, s), 4.60(2H, d, J 5.0 Hz), 6.71-6.72(1H, m), 6.99(2H, s), 7.27-7.31(2H, m), 7.45(1H, s), 7.65(1H, d, J 7.5 Hz), 7.94-7.95(1H, m) and 9.08(1H, t, J 5.0 Hz); M/Z 354(M+H)$^+$; LC 1.8 min. (50/80) |
| 47 | K | 63 | IR ν$_{max}$ (DR)/cm$^{-1}$; NMR δ$_H$ (400 MHz, DMSO) 3.67(3H, s), 4.09(2H, d, J 6.1 Hz), 6.71(1H, dd, J 1.9, 3.5 Hz), 6.93(2H, br s), 7.30(1H, m), 7.40(1H, s), 7.94(1H, m) and 8.71(1H, t, J 6.1 Hz); M/Z 277(M+H)$^+$; LC 3.6 min. (20/50) |
| 48 | J | 46 | Mp 193.8-194.0° C.; IR ν$_{max}$ (DR)/cm$^{-1}$ 3328, 1536, 1348, 1239, 729 and 672; NMR δ$_H$ (400 MHz, DMSO) 4.57(2H, d, J 6.0 Hz) 6.37-6.41(1H, m), 6.71(1H, dd, J 3.0, 1.5 Hz), 6.89(2H, br s), 6.98(1H, dd, J 8.0, 1.5 Hz), 7.27-7.33(2H, m), 7.36(1H, br s), 7.43(1H, s), 7.49(1H, d, J 8.0 Hz), 7.93-7.95(1H, m), 8.67(1H, t, J 6.5 Hz) and 11.03(1H, br s); M/Z 334(M+H)$^+$; LC 2.9 min. (50/80) |
| 49 | J | 28 | Mp 230.7-230.9° C.; IR ν$_{max}$ (DR)/cm$^{-1}$ 3408, 3190, 1652, 1504, 1246, 788 and 754; NMR δ$_H$ (400 MHz, DMSO) 5.12(2H, d, J 6.5 Hz) 6.70(1H, dd, J 3.5, 1.5 Hz), 6.89(2H, br s), 7.29(1H, d, J 3.5 Hz), 7.43(1H, s), 7.54-7.64(2H, m), 7.69(1H, d, J 7.0 Hz), 7.90-7.96(2H, m), 8.42(1H, dd, J 8.5, 2.0 Hz), 8.98(1H, t, J 6.5 Hz) and 9.02(1H, dd, J 4.0, 1.5 Hz); M/Z 346(M+H)$^+$; LC 2.7 min. (50/80) |
| 50 | J | 72 | IR ν$_{max}$ (DR)/cm$^{-1}$; NMR δ$_H$ (400 MHz, DMSO) 3.01(2H, t, J 7.0 Hz), 3.67(2H, dd, J 7.0, 13.2 Hz), 6.71(1H, m), 6.87(2H, br s), 7.22-7.30(4H, m), 7.38(1H, s), 7.72(1H, dt, J 1.8, 3.7 Hz), 7.93(1H, m), 8.55(1H, d, J 5.2 Hz) and 8.61(1H, t, J 6.0 Hz); M/Z 310(M+H)$^+$; LC 1.0 min. (50/80) |
| 51 | J | 85 | IR ν$_{max}$ (DR)/cm$^{-1}$; NMR δ$_H$ (400 MHz, DMSO) 4.58(2H, d, J 6.4 Hz), 6.71(1H, dd, J 1.6, 3.0 Hz), 6.92(2H, br s), 7.30-7.37(4H, m), 7.42(1H, s), 7.47(1H, dd, J 1.6, 7.0 Hz), 7.94(1H, m) and 8.83(1H, t, J 6.4 Hz); M/Z 329(M+H)$^+$; LC 3.8 min. (50/80) |
| 52 | J | 86 | IR ν$_{max}$ (DR)/cm$^{-1}$; NMR δ$_H$ (400 MHz, DMSO) 4.69(2H, d, J 6.0 Hz), 6.71(1H, dd, J 1.6, 3.6 Hz), 6.91(2H, br s), 7.30(1H, d, J 3.6 Hz), 7.42(1H, s), 7.50(1H, q, J 7.6 Hz), 7.66(1H, t, J 7.6 Hz), 7.75(1H, d, J 7.6 Hz), 7.94(1H, m) and 8.92(1H, t, J 6.0 Hz); M/Z 363(M+H)$^+$; LC 4.3 min. (50/80) |
| 53 | J | 34 | Mp 171.2-172.1° C.; IR ν$_{max}$ (DR)/cm$^{-1}$ 3336, 3220, 1520, 1232, 828 and 772; NMR δ$_H$ (400 MHz, DMSO) 4.70(2H, d, J 6.0 Hz) 6.71(1H, dd, J 3.5, 1.5 Hz), 6.88(2H, br s), 7.30(1H, d, J 3.5 Hz), 7.43(1H, s), 8.07(1H, d, J 9.0 Hz) and 9.11(1H, t, J 6.0 Hz); M/Z 353(M+H)$^+$; LC 2.6 min. (50/80) |
| 54 | U | 58 | NMR δ$_H$ (400 MHz, DMSO) 2.86-2.92(6H, m), 4.60(2H, d, J 6.0 Hz), 5.13(2H, s), 6.70-6.71(1H, m), 6.90(2H, s), 7.26(2H, d, J 7.5 Hz), 7.29(1H, d, J 3.5 Hz), 7.42(1H, s), 7.80(1H, t, J 8.0 Hz), 7.93(1H, s) and 8.98(1H, t, J 5.0 Hz); LC 1.1 min. (50/80) |
| 55 | J | 2 | NMR δ$_H$ (400 MHz, DMSO) 4.76(2H, d, J 6.0 Hz), 6.71-6.72(1H, m), 6.94(2H, s), 7.30(1H, dd, J 3.5, 1.0 Hz), 7.45(1H, s), 7.63-7.68(1H, m), 7.74-7.79(2H, m), 7.94-7.96(2H, m), 8.13(1H, d, J 8.0 Hz), 8.98(1H, t, J 6.5 Hz) and 9.31(1H, s); M/Z 346(M+H)$^+$; LC 2.4 min. (50/80) |
| 56 | J | 80 | IR ν$_{max}$ (DR)/cm$^{-1}$; NMR δ$_H$ (400 MHz, DMSO) 3.50(4H, m), 3.60(2H, m), 3.71(2H, m), 6.66-6.70(2H, m), 6.84(1H, d, J 8.7 Hz), 6.94(2H, br s), 6.98(1H, s), 7.26(1H, d, J 3.6 Hz), 7.55(1H, m), 7.91(1H, m) and 8.13(1H, dd, J 1.8, 5.2 Hz); M/Z 351(M+H)$^+$; LC 1.0 min. (50/80) |
| 57 | J | 40 | Mp 180.9-181.4° C.; IR ν$_{max}$ (DR)/cm$^{-1}$ 3393, 3202, 1686, 1643, 1517, 1243 and 753; NMR δ$_H$ (400 MHz, DMSO) 4.81(2H, d, J 6.0 Hz), 6.71(1H, dd, J 3.5, 1.5 Hz), 6.96(2H, br s), 7.31(1H, d, J 3.5 Hz), 7.46(1H, s), 7.53(1H, d, J 8.5 Hz), 7.57-7.62(1H, m), 7.75-7.80(1H, m), 7.93-7.95(1H, m), 7.97(1H, dd, J 8.0, 1.0 Hz), 8.07(1H, d, J 8.5 Hz), 8.36(1H, d, J 8.5 Hz) and 9.24(1H, d, J 6.0 Hz); M/Z 346(M+H)$^+$; LC 2.4 min. (50/80) |
| 58 | J | 41 | Mp 219.9-222.3° C.; IR ν$_{max}$ (DR)/cm$^{-1}$ 3318, 2911, 1667, 1518, 1247 and 1129; NMR δ$_H$ (400 MHz, DMSO) 4.91(2H, d, J 6.0 Hz) 6.72(1H, dd, J 3.5, 2.0 Hz), 6.93(2H, br s), 7.32(1H, d, J 3.5 Hz), |

TABLE 2-continued

| Example | Method | Yield (%) | Physical Data |
|---|---|---|---|
| | | | 7.39-7.46(2H, m), 7.47-7.54(1H, m), 7.92-8.00(2H, m), 8.06(1H, d, J 8.0 Hz) and 9.34(1H, t, J 6.2 Hz); M/Z 352(M+H)$^+$; LC 2.6 min. (50/80) |
| 59 | J | 35 | Mp 154.5-156.9° C.; NMR δ$_H$ (400 MHz, DMSO) 0.17-0.21(2H, m), 0.45-0.49(2H, m), 1.03-1.11(1H, m), 2.31(3H, s), 3.37(2H, d, J 7.0 Hz), 4.59-4.60(4H, m), 6.71-6.72(1H, m), 6.98(2H, s), 7.29-7.31(2H, m), 7.45(1H, s), 7.64(1H, d, J 8.0 Hz), 7.94-7.95(1H, m) and 9.06(1H, t, J 5.0 Hz); M/Z 394(M+H)$^+$; LC 4.1 min. (50/80) |
| 60 | J | 67 | Mp 158.7-158.9° C., NMR δ$_H$ (400 MHz, DMSO) 1.51(3H, d, J 7.0 Hz), 5.13(1H, pent, J 8.0 Hz), 6.70-6.71(1H, m), 6.94(2H, s), 7.24-7.29(2H, m), 7.33-7.42(5H, m), 7.93-7.94(1H, m) and 8.56(1H, d, J 8.5 Hz); M/Z 309(M+H)$^+$; LC 3.3 min. (50/80) |
| 61 | J | 71 | Mp 171.2-172.7° C.; IR ν$_{max}$ (DR)/cm$^{-1}$ 3490, 3362, 3172, 1634, 1516, 1234, 1018 and 734; NMR δ$_H$ (400 MHz, DMSO) 4.48(2H, d, J 6.0 Hz) 6.71(1H, dd, J 3.5, 1.5 Hz), 6.87(2H, br s), 7.29(1H, dd, J 3.5, 1.0 Hz), 7.32-7.42(4H, m), 7.94(1H, d, J 2.5 Hz) and 8.91(1H, t, J 6.5 Hz); M/Z 329(M+H)$^+$; LC 4.5 min. (50/80) |
| 62 | J | 65 | Mp 176.2-177.3° C.; IR ν$_{max}$ (DR)/cm$^{-1}$ 3332, 3208, 1672, 1550, 1226, 838 and 734; NMR δ$_H$ (400 MHz, DMSO) 4.47(2H, d, J 6.5 Hz) 6.71(1H, dd, J 3.5, 2.0 Hz), 6.87(2H, br s), 7.11-7.20(2H, m), 7.29(1H, dd, J 3.5, 1.0 Hz), 7.33-7.40(2H, m), 7.41(1H, s), 7.92-7.95(1H, m) and 8.86(1H, t, J 6.5 Hz); M/Z 313(M+H)$^+$; LC 2.9 min. (50/80) |
| 63 | J | 73 | Mp 158.8-159.1° C.; NMR δ$_H$ (400 MHz, DMSO) 1.51(3H, d, J 7.0 Hz), 5.13(1H, pent, J 7.5 Hz), 6.70-6.71(1H, m), 6.94(2H, s), 7.24-7.29(2H, m), 7.33-7.42(5H, m), 7.93-7.94(1H, m) and 8.56(1H, d, J 8.5 Hz); M/Z 309(M+H)$^+$; LC 3.2 min. (50/80) |
| 64 | J | 7 | NMR δ$_H$ (400 MHz, DMSO) 3.41(4H, s), 3.56-3.58(4H, m), 4.60(2H, d, J 6.0 Hz), 5.17(2H, s), 6.71-6.72(1H, m), 6.93(2H, s), 7.26-7.30(3H, m), 7.42(1H, s), 7.80(1H, t, J 8.0 Hz), 7.94-7.95(1H, m) and 9.00(1H, t, J 6.0 Hz); M/Z 439(M+H)$^+$; LC 1.1 min. (50/80) |
| 65 | J | 62 | Mp 149.4-150.4° C.; IR ν$_{max}$ (DR)/cm$^{-1}$ 3406, 3318, 3208, 1682, 1514, 1246, 1030 and 596; NMR δ$_H$ (400 MHz, DMSO) 3.73(3H, s) 4.42(2H, d, J 6.0 Hz), 6.71(1H, dd, J 3.5, 1.5 Hz), 6.84-6.93(4H, m), 7.23-7.28(2H, m), 7.29(1H, dd, J 3.5, 1.0 Hz), 7.41(1H, s), 7.92-7.95(1H, m) and 8.69(1H, t, J 6.0 Hz); M/Z 325(M+H)$^+$; LC 2.5 min. (50/80) |
| 66 | J | 68 | Mp 226.2-226.3° C.; NMR δ$_H$ (400 MHz, DMSO) 4.86(2H, br s), 5.04(2H, br s), 6.71(1H, dd, J 3.5, 2.0 Hz), 7.01(2H, br s), 7.16(1H, s), 7.28(1H, d, J 3.5 Hz), 7.29-7.35(3H, m), 7.38-7.44(1H, m) and 7.92-7.96(1H, m); M/Z 307(M+H)$^+$; LC 2.1 min. (50/80) |
| 67 | J | 29 | IR ν$_{max}$ (DR)/cm$^{-1}$; NMR δ$_H$ (400 MHz, DMSO) 3.28(3H, s), 3.47(4H, m), 6.71(1H, dd, J 1.6, 3.5 Hz), 6.93(2H, br s), 7.29(1H, d, J 3.5 Hz), 7.40(1H, s), 7.94(1H, m) and 8.30(1H, m); M/Z 263(M+H)$^+$; LC 3.5 min. (20/50) |
| 68 | J | 32 | IR ν$_{max}$ (DR)/cm$^{-1}$; NMR δ$_H$ (400 MHz, DMSO) 4.31(2H, d, J 5.9 Hz), 6.72(1H, dd, J 1.8, 3.4 Hz), 6.90(2H, br s), 7.32(1H, d, J 3.3 Hz), 7.40(1H, s), 7.95(1H, m) and 9.08(1H, t, J 5.8 Hz); M/Z 244(M+H)$^+$; LC 3.8 min. (20/50) |
| 69 | J | 61 | Mp 182.0-182.1° C.; IR ν$_{max}$ (DR)/cm$^{-1}$ 3356, 3187, 1673, 1638, 1509, 1229 and 805; NMR δ$_H$ (400 MHz, DMSO) 2.28(3H, s) 4.44(2H, d, J 6.0 Hz), 6.71(1H, dd, J 3.5, 1.5 Hz), 6.91(2H, br s), 7.14(2H, d, J 8.0 Hz), 7.21(2H, d, J 8.0 Hz), 7.31(1H, d, J 3.5 Hz), 7.41(1H, s), 7.95(1H, t, J 1.0 Hz) and 8.76(1H, t, J 6.5 Hz); M/Z 309(M+H)$^+$; LC 4.2 min. (50/80) |
| 70 | J | 50 | Mp 191.9-192.0° C.; NMR δ$_H$ (400 MHz, DMSO) 1.71(6H, s), 6.70-6.71(1H, m), 7.07(2H, s), 7.20-7.24(1H, m), 7.28(1H, d, J 3.5 Hz), 7.31-7.34(3H, m), 7.39-7.42(2H, m), 7.93-7.94(1H, m) and 8.37(1H, s); M/Z 323(M+H)$^+$; LC 3.7 min. (50/80) |
| 71 | J | 61 | Mp 193.3-193.6° C.; IR ν$_{max}$ (DR)/cm$^{-1}$ 3422, 3318, 1616, 1538, 1226, 776 and 746; NMR δ$_H$ (400 MHz, DMSO) 2.88(2H, q, J 6.0 Hz) 3.61(1H, t, J 6.0 Hz), 3.83(1H, t, J 6.0 Hz), 4.59(1H, s), 4.76(1H, s), 6.67-6.73(1H, m), 6.93-7.02(3H, m), 7.06-7.30(5H, m) and 7.92(1H, d, J 4.5 Hz); M/Z 321(+H)$^+$; LC 1.9 min. (50/80) |
| 72 | J | 17 | Mp 203.8-204.5° C.; IR ν$_{max}$ (DR)/cm$^{-1}$ 3486, 3314, 3202, 1644, 1538, 1224 and 742; NMR δ$_H$ (400 MHz, DMSO) 1.86-2.00(2H, m) 2.81(2H, t, J 6.5 Hz), 3.70(2H, br s), 6.66-6.72(1H, m), 6.85-7.12(4H, br m), 7.14-7.27(2H, m) and 7.91(1H, s); M/Z 321(M+H)$^+$; LC 1.5 min. (50/80) |
| 73 | J | 83 | IR ν$_{max}$ (DR)/cm$^{-1}$; NMR δ$_H$ (400 MHz, DMSO) 4.50(2H, d, J 6.4 Hz), 6.72(1H, m), 6.91(2H, br s), 7.07-7.18(3H, m), 7.30(1H, d, J 3.6 Hz), 7.35-7.41, 2H, m), 7.95(1H, m) and 8.96(1H, t, J 6.4 Hz); M/Z 313(M+H)$^+$; LC 3.2 min. (50/80) |
| 74 | J | 84 | IR ν$_{max}$ (DR)/cm$^{-1}$; NMR δ$_H$ (400 MHz, DMSO) 4.49(2H, d, J 6.4 Hz), 6.72(1H, m), 6.91(2H, br s), 7.28-7.41(6H, m), 7.95(1H, m) and 8.99(1H, t, J 6.4 Hz); M/Z 329(M+H)$^+$; LC 4.5 min. (50/80) |
| 75 | J | 60 | Mp 251.9-252.3° C.; IR ν$_{max}$ (DR)/cm$^{-1}$ 3196, 2981, 1633, 1485, 1239, 1002, 756 and 538; NMR δ$_H$ (400 MHz, DMSO) 3.14(1H, dd, J 16.5, 8.0 Hz) 4.16(2H, t, J 8.5 Hz), 6.71(1H, dd, J 3.5, 1.5 Hz), 6.97(2H, br |

TABLE 2-continued

| Example | Method | Yield (%) | Physical Data |
|---|---|---|---|
| | | | s), 7.06-7.14(2H, m), 7.20-7.33(3H, m), 7.93(1H, d, J 1.0 Hz) and 8.13(1H, d, J 8.0 Hz); M/Z 307(M+H)⁺; LC 2.3 min. (50/80) |
| 76 | J | 86 | IR $\nu_{max}$ (DR)/cm⁻¹; NMR $\delta_H$ (400 MHz, DMSO) 2.33(3H, s), 6.73(1H, dd, J 1.6, 3.6 Hz), 6.96-7.02(3H, m), 7.27(1H, t, J 8.0 Hz), 7.33(1H, m), 7.47(1H, s), 7.58-7.62(2H, m), 7.96(1H, m) and 10.16(1H, s); M/Z 295(M+H)⁺; LC 4.8 min. (50/80) |
| 77 | J | 62 | IR $\nu_{max}$ (DR)/cm⁻¹; NMR $\delta_H$ (400 MHz, DMSO) 2.26(3H, s), 6.73(1H, dd, J 2.0, 3.6 Hz), 7.06(2H, br s), 7.27(1H, m), 7.35(1H, m), 7.48(1H, s), 7.75(1H, m), 7.96(1H, m), 8.31(1H, m) and 10.20(1H, s); M/Z 295(M+H)⁺; LC 1.1 min. (50/80) |
| 78 | J | 64 | Mp 126.7-127.2 °C.; IR $\nu_{max}$ (DR)/cm⁻¹ 3326, 3206, 1634, 1520 and 750; NMR $\delta_H$ (400 MHz, DMSO) 1.92-2.04(1H, m), 2.43-2.55(1H, m), 2.81-2.92(1H, m), 2.96-3.06(1H, m), 5.49(1H, q, J 7.5 Hz), 6.71(1H, dd, J 3.5, 2.0 Hz), 6.91(2H, br s), 7.17-7.32(5H, m), 7.45(1H, s), 7.93-7.96(1H, m) and 8.45(1H, d, J 8.5 Hz); M/Z 321(M+H)⁺; LC 4.2 min. (50/80) |
| 79 | J | 50 | Mp 111.8-112.5° C.; IR $\nu_{max}$ (DR)/cm⁻¹ 3205, 2940, 1706, 1651, 1537, 1269, 1014 and 748; NMR $\delta_H$ (400 MHz, DMSO) 1.92-2.04(1H, m), 2.45-2.55(1H, m), 2.81-2.92(1H, m), 2.97-3.06(1H, m), 5.49(1H, dd, J 16.0, 7.5 Hz), 6.72(1H, d, J 3.5 Hz), 6.91(2H, br s), 7.17-7.32(4H, m), 7.45(1H, s), 7.95(1H, d, J 1.0 Hz), 8.45(1H, d, J 9.0 Hz) and 11.81(1H, s); M/Z 321(M+H)⁺; LC 4.1 min. (50/80) |
| 80 | U | 16 | NMR $\delta_H$ (400 MHz, DMSO) 1.43-1.49(4H, m), 1.52-1.57(2H, m), 3.39(4H, s), 4.59(2H, d, J 6.0 Hz), 5.14(2H, s), 6.71-6.72(1H, m), 6.93(2H, s), 7.26(2H, t, J 8.0 Hz), 7.30-7.31(1H, m), 7.42(1H, s), 7.80(1H, t, J 8.0 Hz), 7.94-7.95(1H, m) and 9.00(1H, t, J 6.0 Hz); M/Z 437(M+H)⁺; LC 2.8 min. (50/80) |
| 81 | U | 2 | NMR $\delta_H$ (400 MHz, DMSO) 1.77-1.86(4H, m), 3.34-3.38(4H, m), 4.60(2H, d, J 6.0 Hz), 5.14(2H, s), 6.71-6.72(1H, m), 6.93(2H, s), 7.26-7.30(3H, m), 7.42(1H, s), 7.79(1H, t, J 7.5 Hz), 7.94-7.95(1H, m) and 8.99(1H, t, J 6.0 Hz); M/Z 423(M+H)⁺; LC 1.7 min. (50/80) |
| 82 | T | 33 | NMR $\delta_H$ (400 MHz, DMSO) 3.62-3.66(2H, m), 4.59(2H, d, J 6.0 Hz), 5.00-5.17(5H, m), 5.76-5.85(1H, m), 6.71-6.72(1H, m), 6.93(2H, s), 7.25-7.28(2H, m), 7.30(1H, dd, J 3.5, 1.0 Hz), 7.42(1H, s), 7.57(1H, t, J 5.5 Hz), 7.80(1H, t, J 7.5 Hz), 7.94-7.95(1H, m) and 9.01(1H, t, J 6.0 Hz); LC 1.4 min. (50/80) |
| 83 | J | 28 | Mp 131.0-131.1° C.; IR $\nu_{max}$ (DR)/cm⁻¹ 3367, 3196, 2940, 1636, 1522, 1224, 1027 and 746; NMR $\delta_H$ (400 MHz, DMSO) 1.79-1.88(2H, m) 2.62(2H, t, J 7.5 Hz), 3.32(2H, t, J 7.0 Hz), 6.71(1H, dd, J 3.0, 1.5 Hz), 6.86(2H, br s), 7.15-7.31(6H, m), 7.38(1H, s), 7.93-7.94(1H, m) and 8.42(1H, t, J 6.0 Hz); M/Z 323(M+H)⁺; LC 4.1 min. (50/80) |
| 84 | V | 35 | IR $\nu_{max}$ (DR)/cm⁻¹ 3240, 1666, 1458, 1310, 1028 and 765; NMR $\delta_H$ (400 MHz, DMSO) 2.32(3H, s) 4.46(2H, d, J 6.5 Hz), 6.72(1H, dd, J 3.5, 1.5 Hz), 7.20-7.36(4H, m), 7.44(1H, s), 7.94-7.97(1H, m) and 8.92(1H, t, J 6.0 Hz); M/Z 324(M+H)⁺; LC 1.2 min. (50/80) |
| 85 | T | 57 | Mp 151.6-155.7° C.; NMR $\delta_H$ (400 MHz, DMSO) 0.84(3H, t, J 7.0 Hz), 1.40-1.47(2H, m), 2.97(2H, q, J 6.5 Hz), 4.60(2H, d, J 5.5 Hz), 5.09(2H, s), 6.71-6.72(1H, m), 6.93(2H, s), 7.24-7.27(2H, m), 7.30(1H, dd, J 3.5, 1.0 Hz), 7.36(1H, t, J 8.0 Hz), 7.42(1H, s), 7.80(1H, t, J 8.0 Hz), 7.94-7.95(1H, m) and 9.01(1H, t, J 6.0 Hz); LC 1.6 min. (50/80) |
| 86 | T | 43 | NMR $\delta_H$ (400 MHz, DMSO) 1.24(9H, s), 4.59(2H, d, J 6.0 Hz), 5.05(2H, s), 6.71-6.72(1H, m), 6.93(2H, s), 7.13(1H, s), 7.25(1H, d, J 3.0 Hz), 7.27(1H, d, J 2.5 Hz), 7.30-7.31(1H, m), 7.42(1H, s), 7.80(1H, t, J 8.0 Hz), 7.94-7.94(1H, m) and 9.00(1H, t, J 6.0 Hz); LC 2.3 min. (50/80) |
| 87 | J | 36 | NMR $\delta_H$ (400 MHz, DMSO) mixture of rotainers 2.85(1.2H, s), 2.87(1.8H, s), 4.54(0.8H, s), 4.65(1.2H, s), 6.67-6.70(1H, m), 6.93-6.94(2H, m), 6.97(0.6H, s), 6.97(0.4H, s), 7.23-7.41(6H, m) and 7.89-7.91(1H, m); M/Z 309(M+H)⁺; LC 1.4 min. (50/80) |
| 88 | J | 11 | Mp 191.9-192.0° C.; NMR $\delta_H$ (400 MHz, DMSO) 2.48(3H, s), 4.63(2H, d, J 5.5 Hz), 6.69-6.72(1H, m), 6.89(2H, br s), 7.29(1H, d, J 3.5 Hz), 7.41(1H, s), 7.93(1H, s), 8.50(2H, d, J 8.5 Hz) and 8.94(1H, t, J 5.5 Hz); M/Z 311(M+H)⁺; LC 4.8 min. (20/50) |
| 89 | J | 38 | Mp 178.1-178.7° C.; IR $\nu_{max}$ (DR)/cm⁻¹ 3331, 3181, 2926, 1541, 1228, 1011 and 885; NMR $\delta_H$ (400 MHz, DMSO) 1.77-1.92(3H, m) 1.96-2.06(1H, m), 2.69-2.87(2H, m), 5.14-5.21(1H, m), 6.71(1H, dd, J 1.5, 2.0 Hz), 6.91(2H, br s), 7.12-7.22(4H, m), 7.30(1H, dd, J 3.5, 1.0 Hz), 7.46(1H, br s), 7.94(1H, t, J 1.0 Hz) and 8.38(1H, d, J 9.0 Hz); M/Z 355(M+H)⁺; LC 5.1 min. (50/80) |
| 90 | J | 58 | Mp 220.0-221.3° C.; IR $\nu_{max}$ (DR)/cm⁻¹ 3332, 3198, 1634, 1520, 1238 and 742; NMR $\delta_H$ (400 MHz, DMSO) 2.95(2H, dd, J 16.0, 6.0 Hz) 3.26(2H, dd, J 16.0, 7.0 Hz), 4.64-4.75(1H, m), 6.70(1H, dd, J 3.5, 2.0 Hz), 6.88(2H, br s), 7.14-7.27(2H, m), 7.28(1H, d, J 4.0 Hz), 7.40(1H, s), 7.91-7.95(1H, m) and 8.41(1H, d, J 7.5 Hz); M/Z 321(M+H)⁺; LC 4.0 min. (50/80) |

TABLE 2-continued

| Example | Method | Yield (%) | Physical Data |
|---|---|---|---|
| 91 | P | 72 | Mp >200° C.(dec); IR $\nu_{max}$ (DR)/cm$^{-1}$ 3082, 1684 and 1458; NMR $\delta_H$ (400 MHz, DMSO) 4.16(4H, br s) 4.79(2H, d, J 6.0 Hz), 6.72-6.73(1H, m), 7.31(1H, d, J 3.5 Hz), 7.44(1H, s), 7.58(2H, s), 7.95-7.96(1H, m), 9.14(1H, br t, J 6.0 Hz), and 14.30(1H, br s); M/Z 285(M+H)$^+$; LC 3.4 min. (20/50) |
| 92 | P | 94 | Mp 270.7-271.5° C.; IR $\nu_{max}$ (DR)/cm$^{-1}$ 3065 and 1664; NMR $\delta_H$ (400 MHz, DMSO) 0.88(3H, t, J 7.5 Hz) 1.75-1.84(2H, m), 4.16(2H, t, J 7.5 Hz), 4.20(4H, br s), 4.83(2H, d, J 6.0 Hz), 6.71-6.72(1H, m), 7.31-7.32(1H, m), 7.42(1H, s), 7.63(1H, d, J 2.0 Hz), 7.73(1H, d, J 2.0 Hz), 7.94-7.95(1H, m) and 9.24(1H, br t, J 6.0 Hz); M/Z 327(M+H)$^+$; LC 1.1 min. (20/50) |
| 93 | J | 87 | IR $\nu_{max}$ (DR)/cm$^{-1}$; NMR $\delta_H$ (400 MHz, DMSO) 4.54(2H, d, J 6.0 Hz), 6.71(1H, m), 6.89(2H, br s), 7.30(1H, m), 7.35-7.38(2H, m), 7.42(1H, s), 7.64(1H, m), 7.94(1H, m) and 8.83(1H, t, J 6.0 Hz); M/Z 373, 375(M+H)$^+$; LC 4.4 min. (50/80) |
| 94 | J | 78 | Mp 178.1-179.3° C.; NMR $\delta_H$ (400 MHz, DMSO) 4.58(2H, d, J 6.5 Hz), 6.70-6.72(1H, m), 6.88(2H, s), 7.29(1H, d, J 3.5 Hz), 7.37(1H, d, J 7.5 Hz), 7.41(1H, s), 7.53(1H, d, J 7.0 Hz), 7.73(1H, t, J 8.0 Hz), 7.93-7.94(1H, m) and 8.99(1H, t, J 6.5 Hz); M/Z 374(M+H)$^+$; LC 1.9 min. (50/80) |
| 95 | W | 22 | Mp 223.8-223.9° C.; NMR $\delta_H$ (400 MHz, DMSO) 4.36(2H, d, J 5.5 Hz), 5.94(2H, s), 6.34(1H, d, J 7.5 Hz), 6.45(1H, d, J 7.0 Hz), 6.70-6.71(1H, m), 6.93(2H, s), 7.29-7.30(1H, m), 7.34(1H, t, J 7.5 Hz), 7.42(1H, s), 7.93-7.94(1H, m) and 8.87(1H, t, J 5.5 Hz); LC 0.9 min. (50/80) |
| 96 | J | 73 | Mp 248.2-249.0° C.; NMR $\delta_H$ (400 MHz, DMSO) 2.10(2H, pent, J 7.0 Hz), 3.32(2H, q, J 6.5 Hz), 4.25(2H, t, J 7.0 Hz), 6.72-6.74(1H, m), 7.34-7.35(1H, m), 7.40(1H, s), 7.68-7.69(1H, m), 7.82-7.83(1H, m), 7.96-7.97(1H, m), 8.70(1H, t, J 5.0 Hz) and 9.17-9.18(1H, m); M/Z 313(M+H)$^+$; LC 3.7 min. (50/80) |
| 97 | P | 92 | Mp 247.6-248.8° C.; IR $\nu_{max}$ (DR)/cm$^{-1}$ 3024, 1665 and 1466; NMR $\delta_H$ (400 MHz, DMSO) 3.25(3H, s) 3.69(2H, t, J 5.0 Hz), 4.17(4H, br s), 4.42(2H, t, J 5.0 Hz), 4.84(2H, d, J 5.5 Hz), 6.71-6.72(1H, m), 7.31(1H, d, J 3.5 Hz), 7.42(1H, s), 7.62(1H, d, J 2.0 Hz), 7.68(1H, d, J 2.0 Hz), 7.94-7.95(1H, m) and 9.16(1H, br t, J 5.5 Hz); M/Z 343(M+H)$^+$; LC 4.6 min. (20/50) |
| 98 | P | 93 | Mp 263.1-264.9° C.; IR $\nu_{max}$ (DR)/cm$^{-1}$ 3022, 1664 and 1466; NMR $\delta_H$ (400 MHz, DMSO) 1.39(3H, t, J 7.5 Hz) 3.62(4H, br s), 4.22(2H, q, J 7.5 Hz), 4.82(2H, d, J 5.5 Hz), 6.71-6.72(1H, m), 7.30-7.31(1H, m), 7.41(1H, s), 7.62(1H, d, J 2.0 Hz), 7.74(1H, d, J 2.0 Hz), 7.94-7.95(1H, m) and 9.21(1H, br t, J 5.5 Hz); M/Z 313(M+H)$^+$; LC 5.0 min. (20/50) |
| 99 | T | 20 | NMR $\delta_H$ (400 MHz, DMSO) 4.22(2H, d, J 6.5 Hz), 4.60(2H, d, J 6.0 Hz), 5.13(2H, s), 6.71-6.73(1H, m), 6.97(2H, s), 7.22-7.34(8H, m), 7.42(1H, s), 7.81(1H, t, J 7.5 Hz), 7.95-7.96(1H, m), 7.98(1H, t, J 6.5 Hz) and 9.05(1H, t, J 6.0 Hz); M/Z 459(M+H)$^+$; LC 3.2 min. (50/80) |
| 100 | T | 17 | NMR $\delta_H$ (400 MHz, DMSO)1.36-1.51(4H, m), 1.58-1.66(2H, m), 1.75-1.83(2H, m), 3.78-3.85(1H, m), 4.59(2H, d, J 5.5 Hz), 5.08(2H, s), 6.71-6.72(1H, m), 6.93(2H, s), 7.26(2H, d, J 8.0 Hz), 7.30(1H, d, J 3.5 Hz), 7.36(1H, d, J 7.0 Hz), 7.42(1H, s), 7.80(1H, t, J 7.5 Hz), 7.94-7.95(1H, m) and 9.00(1H, t, J 6.0 Hz); M/Z 437(M+H)$^+$; LC 2.7 min. (50/80) |
| 101 | T | 36 | NMR $\delta_H$ (400 MHz, DMSO) 0.85(3H, t, J 7.0 Hz), 1.22-1.28(6H, m), 1.37-1.42(2H, m), 2.99(2H, q, J 6.0 Hz), 4.59(2H, d, J 6.0 Hz), 5.09(2H, s), 6.71-6.72(1H, m), 6.93(2H, s), 7.25(2H, t, J 7.5 Hz), 7.30(1H, d, J 3.5 Hz), 7.34(1H, t, J 5.5 Hz), 7.42(1H, s), 7.79(1H, t, J 7.5 Hz), 7.94-7.95(1H, m) and 9.01(1H, t, J 5.5 Hz); M/Z 453(M+H)$^+$; LC 4.9 min. (50/80) |
| 102 | J | 73 | Mp 203.0-203.1° C.; NMR $\delta_H$ (400 MHz, DMSO) 2.34(3H, s), 2.78(6H, s), 4.48(2H, d, J 6.0 Hz), 6.70-6.72(1H, m), 6.78(1H, d, J 7.5 Hz), 6.88(2H, s), 7.29(1H, d, J 3.5 Hz), 7.40-7.42(2H, m), 7.94-7.95(1H, m) and 8.81(1H, t, J 6.0 Hz); M/Z 353(M+H)$^+$; LC 2.7 min. (50/80) |
| 103 | K | 64 | IR $\nu_{max}$ (DR)/cm$^{-1}$; NMR $\delta_H$ (400 MHz, DMSO) 3.70(3H, s), 5.66(1H, m), 6.71(1H, dd, J 1.8, 3.5 Hz), 7.07(2H, br s), 7.30(1H, d, J 3.5 Hz), 7.37-7.46(6H, m), 7.94(1H, m) and 8.75(1H, d, J 7.3 Hz); M/Z 353(M+H)$^+$; LC 2.5 min. (50/80) |
| 104 | K | 39 | IR $\nu_{max}$ (DR)/cm$^{-1}$; NMR $\delta_H$ (400 MHz, DMSO) 3.70(3H, s), 5.66(1H, m), 6.71(1H, dd, J 1.8, 3.5 Hz), 7.07(2H, br s), 7.30(1H, d, J 3.5 Hz), 7.37-7.46(6H, m), 7.94(1H, m) and 8.75(1H, d, J 7.3 Hz); M/Z 353(M+H)$^+$; LC 2.8 min. (50/80) |
| 105 | J | 17 | NMR $\delta_H$ (400 MHz, DMSO) 4.79(2H, d, J 5.5 Hz), 6.70-6.71(1H, m), 6.93(2H, s), 7.28(1H, dd, J 3.5, 1.0 Hz), 7.40(1H, t, J 7.5 Hz), 7.40(1H, s), 7.51(1H, s), 7.52-7.53(1H, m), 7.93-7.94(1H, m) and 8.31(1H, t, J 5.5 Hz); M/Z 363, 365(M+H)$^+$; LC 4.6 min. (50/80) |
| 106 | J | 65 | NMR $\delta_H$ (400 MHz, DMSO) 2.33(3H, s), 3.37(3H, s), 4.49(2H, s), 4.51(2H, d, J 6.0 Hz), 6.61(2H, br s), 6.70(1H, dd, J 1.5, 3.5 Hz), |

TABLE 2-continued

| Example | Method | Yield (%) | Physical Data |
| --- | --- | --- | --- |
| | | | 7.15(1H, dd, J 1.0, 3.5 Hz), 7.27-7.32(2H, m), 7.80(1H, t, J 7.5 Hz), 7.92(1H, d, J 1.0 Hz) and 9.06(1H, t, J 6.5 Hz); M/Z 354(M+H)$^+$; LC 5.1 min. (20/50) |
| 107 | J | 59 | IR $\nu_{max}$ (DR)/cm$^{-1}$; NMR $\delta_H$ (400 MHz, DMSO) 3.57(3H, s), 4.69(2H, s), 4.77(2H, d, J 6.0 Hz), 7.40(2H, br s), 7.57(1H, d, J 8.0 Hz), 7.63(1H, d, J 7.6 Hz), 7.77(1H, s), 8.02(1H, d, J 3.2 Hz), 8.10(1H, d, J 2.8 Hz), 8.16(1H, m) and 9.20(1H, t, J 6.0 Hz); M/Z 357(M+H)$^+$; LC 0.9 min. (50/80) |
| 108 | J | 46 | Mp 229.6-231.7° C.; IR $\nu_{max}$ (DR)/cm$^{-1}$ 3470, 3358, 1672, 1634, 1514 and 782; NMR $\delta_H$ (400 MHz, DMSO) 2.33(3H, s), 4.64(2H, d, J 5.0 Hz), 7.21-7.30(3H, m), 7.64(1H, d, J 6.5 Hz), 7.81(1H, s), 8.01(1H, d, J 3.0 Hz), 8.10(1H, d, J 3.0 Hz), 8.42(1H, d, J 4.5 Hz) and 9.08(1H, t, J 5.0 Hz); M/Z 327(M+H)$^+$; LC 1.3 min. (50/80) |
| 109 | J | 17 | Mp 144.1-144.3° C.; IR $\nu_{max}$ (DR)/cm$^{-1}$ 3471, 3343, 1673, 1232, 866, 780 and 616; NMR $\delta_H$ (400 MHz, DMSO) 0.92(3H, t, J 7.5 Hz), 1.69(2H, m), 2.71(2H, d, J 7.5 Hz), 4.58(2H, d, J 6.0 Hz), 7.10-7.27(4H, m), 7.67(1H, t, J 7.5 Hz), 7.77(1H, s), 8.02(1H, d, J 3.0 Hz), 8.11(1H, d, J 3.0 Hz) and 9.02(1H, t, J 6.0 Hz); M/Z 355(M+H)$^+$; LC 2.5 min. (50/80) |
| 110 | J | 40 | NMR $\delta_H$ (400 MHz, DMSO) 2.39(3H, s), 4.69(2H, d, J 6.0 Hz), 6.34-6.35(1H, m), 6.86(2H, s), 7.22(1H, d, J 3.5 Hz), 7.36(1H, s), 7.48-7.52(2H, m), 7.67(1H, t, J 7.5 Hz), 7.75(1H, d, J 7.5 Hz) and 8.90(1H, t, J 6.0 Hz); M/Z 377(M+H)$^+$; LC 5.3 min. (50/80) |
| 111 | J | 40 | NMR $\delta_H$ (400 MHz, DMSO) 2.39(3H, s), 4.62(2H, d, J 6.0 Hz), 6.34-6.35(1H, m), 6.89(2H, s), 7.21(1H, d, J 3.0 Hz), 7.28-7.31(1H, m), 7.35(1H, d, J 7.5 Hz), 7.37(1H, s), 7.78(1H, dt, J 7.5, 2.0 Hz), 8.53-8.54(1H, m) and 8.94(1H, t, J 5.5 Hz); M/Z 310(M+H)$^+$; LC 1.2 min. (50/80) |
| 112 | J | 19 | NMR $\delta_H$ (400 MHz, DMSO) 2.39(3H, s), 3.56(3H, s), 4.47(2H, d, J 6.0 Hz), 5.90-5.92(1H, m), 6.00-6.01(1H, m), 6.33-6.34(1H, m), 6.68(2H, s), 6.89(2H, s), 7.20(1H, d, J 3.5 Hz), 7.36(1H, s) and 8.29(1H, t, J 5.5 Hz); M/Z 312(M+H)$^+$; LC 2.3 min. (50/80) |
| 113 | J | 18 | NMR $\delta_H$ (400 MHz, DMSO) 2.39(3H, s), 3.38(3H, s), 4.51(2H, s), 4.58(2H, d, J 5.5 Hz), 6.34-6.35(1H, m), 6.87(2H, s), 7.21(1H, d, J 3.5 Hz), 7.24(1H, d, J 8.0 Hz), 7.30(1H, d, J 7.5 Hz), 7.37(1H, s), 7.78(1H, t, J 8.0 Hz) and 8.96(1H, t, J 6.0 Hz); M/Z 354(M+H)$^+$ |
| 114 | T | 38 | NMR $\delta_H$ (400 MHz, DMSO) 1.24(9H, s), 2.39(3H, s), 4.59(2H, d, J 6.0 Hz), 5.04(2H, s), 6.34-6.35(1H, m), 6.90(2H, s), 7.16(1H, s), 7.22(1H, d, J 3.5 Hz), 7.24-7.27(2H, m), 7.37(1H, s), 7.80(1H, t, J 7.5 Hz) and 9.00(1H, t, J 6.0 Hz); M/Z 439(M+H)$^+$; LC 3.4 min. (50/80) |
| 115 | U | 10 | NMR $\delta_H$ (400 MHz, DMSO) 2.39(3H, s), 3.42(4H, s), 3.57(4H, t, J 5.0 Hz), 4.59(2H, d, J 6.0 Hz), 5.17(2H, s), 6.34-6.35(1H, m), 6.90(2H, s), 7.22(1H, d, J 3.0 Hz), 7.26-7.29(2H, m), 7.37(1H, s), 7.80(1H, t, J 8.0 Hz) and 9.00(1H, t, J 6.0 Hz); M/Z 453(M+H)$^+$; LC 1.6 min. (50/80) |
| 116 | AE | 90 | Mp 168.6-168.9° C.; NMR $\delta_H$ (400 MHz, DMSO) 2.39(3H, s) 3.37(3H, s), 4.49(2H, s), 4.50(2H, d, J 6.0 Hz), 6.39-6.40(1H, m), 7-11(1H, br s), 7.31(1H, d, J 7.5 Hz), 7.32(1H, d, J 7.5 Hz), 7.47(1H, d, J 3.5 Hz), 7.82(1H, t, J 7.5 Hz) and 9.26(1H, br t, J 6.0 Hz); M/Z 388, 390(M+H)$^+$; LC 6.5 min. (50/80) |
| 117 | AF | 95 | Mp 193.5-195.1° C.; IR $\nu_{max}$ (DR)/cm$^{-1}$ 3217, 1644 and 1538; NMR $\delta_H$ (400 MHz, DMSO) 2.38(3H, s) 3.37(3H, s), 4.49(2H, s), 4.49(2H, d, J 6.0 Hz), 7.11(2H, br s), 7.31(1H, d, J 7.5 Hz), 7.36(1H, d, J 7.5 Hz), 7.52(1H, d, J 3.5 Hz), 7.82(1H, t, J 7.5 Hz) and 9.23(1H, br t, J 6.0 Hz); M/Z 432, 434(M+H)$^+$; LC 1.1 min. (50/80) |
| 118 | J | 67 | NMR $\delta_H$ (400 MHz, DMSO) 2.38(3H, s), 4.60(2H, d, J 5.5 Hz), 6.38-6.39(1H, m), 7.13(2H, s), 7.50-7.53(2H, m), 7.71(2H, d, J 4.0 Hz), 7.74(1H, d, J 7.5 Hz) and 9.26(1H, t, J 6.0 Hz); M/Z 455, 457(M+H)$^+$; LC 4.4 min. (50/80) |
| 119 | J | 29 | NMR $\delta_H$ (400 MHz, DMSO) 2.31(3H, s), 2.39(3H, s), 4.49(2H, d, J 6.5 Hz), 6.33-6.35(1H, m), 6.86(2H, s), 7.14-7.26(5H, m), 7.36(1H, s) and 8.57(1H, t, J 6.0 Hz); M/Z 323(M+H)$^+$ |
| 120 | J | 44 | NMR $\delta_H$ (400 MHz, DMSO) 2.29(3H, s), 2.39(3H, s), 4.45(2H, d, J 6.5 Hz), 6.33-6.34(1H, m), 6.83(2H, s), 7.06-7.13(3H, m), 7.20-7.24(2H, m), 7.36(1H, s) and 8.74(1H, t, J 6.5 Hz); M/Z 323(M+H)$^+$ |
| 121 | J | 53 | NMR $\delta_H$ (400 MHz, DMSO) 2.28(3H, s), 2.39(3H, s), 4.44(2H, d, J 6.5 Hz), 6.33-6.34(1H, m), 6.83(2H, s), 7.13-7.22(5H, m), 7.35(1H, s) and 8.70(1H, t, J 6.5 Hz); M/Z 323(M+H)$^+$ |
| 122 | J | 23 | NMR $\delta_H$ (400 MHz, DMSO) 2.39(3H, s), 4.57(2H, d, J 6.0 Hz), 6.34-6.35(1H, m), 6.86(2H, s), 7.21(1H, d, J 3.5 Hz), 7.30-7.37(4H, m), 7.45-7.48(1H, m) and 8.80(1H, t, J 6.0 Hz); M/Z 344(M+H)$^+$ |
| 123 | J | 60 | NMR $\delta_H$ (400 MHz, DMSO) 2.39(3H, s), 4.48(2H, d, J 6.5 Hz), 6.33-6.34(1H, m), 6.82(2H, s), 7.20(1H, d, J 3.5 Hz), 7.28-7.33(2H, m), 7.35(1H, s), 7.37-7.39(2H, m) and 8.93(1H, t, J 6.5 Hz); M/Z 344(M+H)$^+$ |
| 124 | J | 9 | NMR $\delta_H$ (400 MHz, DMSO) 2.39(3H, s), 4.50(2H, d, J 6.5 Hz), 6.33-6.34(1H, m), 6.81(2H, s), 7.20(1H, d, J 3.5 Hz), 7.34(1H, s), |

TABLE 2-continued

| Example | Method | Yield (%) | Physical Data |
|---|---|---|---|
| | | | 7.35-7.37(1H, m), 7.72(1H, dt, J 8.0, 2.0 Hz), 8.46(1H, dd, J 4.5, 1.5 Hz), 8.55-8.56(1H, m) and 8.95(1H, t, J 6.5 Hz); M/Z 310(M+H)⁺ |
| 125 | J | 21 | NMR $\delta_H$ (400 MHz, DMSO) 2.39(3H, s), 4.50(2H, d, J 6.5 Hz), 6.34-6.35(1H, m), 6.83(2H, s), 7.21(1H, d, J 3.0 Hz), 7.28-7.30(2H, m), 7.35-7.36(1H, m), 8.50-8.51(2H, m) and 9.01(1H, t, J 6.5 Hz); M/Z 310(M+H)⁺ |
| 126 | J | 60 | NMR $\delta_H$ (400 MHz, DMSO) 2.39(3H, s), 3.85(3H, s), 4.46(2H, d, J 6.0 Hz), 6.33-6.34(1H, m), 6.88(2H, s), 6.91(1H, dt, J 7.5, 1.0 Hz), 7.01-7.03(1H, m), 7.19-7.21(2H, m), 7.27(1H, dt, J 8.0, 1.5 Hz), 7.35(1H, s) and 8.54(1H, t, J 6.0 Hz); M/Z 339(M+H)⁺ |
| 127 | J | 57 | NMR $\delta_H$ (400 MHz, DMSO) 2.39(3H, s), 3.74(3H, s), 4.46(2H, d, J 6.0 Hz), 6.33-6.34(1H, m), 6.82-6.90(5H, m), 7.20(1H, d, J 3.0 Hz), 7.25(1H, t, J 8.0 Hz), 7.36(1H, s) and 8.76(1H, t, J 6.5 Hz); M/Z 339(M+H)⁺ |
| 128 | J | 52 | NMR $\delta_H$ (400 MHz, DMSO) 2.39(3H, s), 4.50(2H, d, J 6.0 Hz), 6.33-6.34(1H, m), 6.82(2H, s), 7.06-7.17(3H, m), 7.21(1H, d, J 3.5 Hz), 7.35(1H, s), 7.35-7.41(1H, m) and 8.91(1H, t, J 6.5 Hz); M/Z 327(M+H)⁺ |
| 129 | J | 34 | NMR $\delta_H$ (400 MHz, DMSO) 2.39(3H, s), 4.57(2H, d, J 6.0 Hz), 6.33-6.34(1H, m), 6.81(2H, s), 7.21(1H, d, J 3.5 Hz), 7.35(1H, s), 7.56-7.68(4H, m) and 9.02(1H, t, J 6.5 Hz); M/Z 327(M+H)⁺ |
| 130 | J | 85 | NMR $\delta_H$ (400 MHz, DMSO) 4.14(2H, s), 4.53(2H, d, J 6.0 Hz), 6.70-6.71(1H, m), 6.86(2H, s), 7.23-7.30(5H, m), 7.35-7.40(7H, m), 7.45-7.48(6H, m), 7.61(1H, d, J 7.5 Hz), 7.90(1H, t, J 7.5 Hz), 7.93-7.94(1H, m), 8.91(1H, t, J 6.0 Hz); LC 7.8 min. (20/50) |
| 131 | J | | NMR $\delta_H$ (400 MHz, DMSO) 0.00(9H, s), 0.89-0.94(2H, m), 3.52-3.56(2H, m), 4.81(2H, d, J 5.0 Hz), 5.15(2H, s), 5.39(2H, s), 6.59-6.61(1H, m), 7.05(1H, d, J 1.0 Hz), 7.07(1H, d, J 1.0 Hz), 7.25(1H, d, J 4.0 Hz), 7.64-7.65(1H, m), 7.78(1H, m) and 8.52-8.56(1H, m); M/Z 415(M+H)⁺. |
| 132 | J | 45 | NMR $\delta_H$ (400 MHz, DMSO) 0.10(6H, s), 0.92(9H, s), 2.39(3H, s), 4.57(2H, d, J 6.0 Hz), 4.57(2H, d, J 6.0 Hz), 4.76(2H, s), 6.34-6.35(1H, m), 6.87(2H, s), 7.20-7.22(2H, m), 7.33(1H, d, J 7.5 Hz), 7.36(1H, s), 7.80(1H, t, J 7.5 Hz) and 8.93(1H, t, J 6.0 Hz); M/Z 454(M+H)⁺ |
| 133 | AD | 49 | NMR $\delta_H$ (400 MHz, DMSO) 2.39(3H, s), 4.56-4.57(4H, m), 6.33-6.34(1H, m), 6.89(2H, s), 7.18(1H, d, J 7.5 Hz), 7.21(1H, d, J 3.0 Hz), 7.36-7.38(2H, m), 7.76(1H, t, J 8.0 Hz) and 8.96(1H, t, J 6.0 Hz); M/Z 340(M+H)⁺. |
| 134 | J | 31 | IR $v_{max}$ (DR)/cm⁻¹ 3445, 3389, 3224, 3110, 2926, 1648, 1540, 1496, 1383, 1230, 1037, 776 and 559; NMR $\delta_H$ (400 MHz, DMSO) 2.20(3H, s), 2.39(3H, s), 3.67(3H, s), 4.35(2H, d, J 6.0 Hz), 5.95(1H, s), 6.33-6.35(1H, m), 6.87(2H, s), 7.20(1H, d, J 3.5 Hz), 7.35(1H, s) and 8.42(1H, t, J 6.0 Hz); M/Z 327(M+H)⁺ |
| 135 | J | 26 | IR $v_{max}$ (DR)/cm⁻¹ 3335, 3192, 2933, 1675, 1633, 1522, 1473, 1264, 1217, 1134, 1021 and 781; NMR $\delta_H$ (400 MHz, DMSO) 2.36-2.37(3H, m), 2.39(3H, s), 4.49(2H, d, J 6.0 Hz), 6.15-6.16(1H, m), 6.33-6.35(1H, m), 6.84(2H, s), 7.21(1H, d, J 3.5 Hz), 7.35(1H, s) and 8.85(1H, t, J 6.0 Hz); M/Z 314(M+H)⁺ |
| 136 | J | 7 | IR $v_{max}$ (DR)/cm⁻¹ 3380, 3192, 2868, 1673, 1527, 1219, 1082, 1022, 861 and 775; NMR $\delta_H$ (400 MHz, DMSO) 1.50-1.59(1H, m), 1.77-1.97(3H, m), 2.39(3H, s), 3.43-3.49(1H, m), 3.65(1H, q, J 7.0 Hz), 3.76-3.82(1H, m), 3.93-3.99(1H, m), 6.33-6.34(1H, m), 6.91(2H, s), 7.20(1H, d, J 3.5 Hz), 7.34(1H, s) and 8.25(1H, t, J 6.0 Hz); M/Z 303(M+H)⁺ |
| 137 | J | 26 | IR $v_{max}$ (DR)/cm⁻¹ 3385, 3200, 3003, 2871, 1681, 1634, 1528, 1470, 1359, 1217, 1022, 797 and 626; NMR $\delta_H$ (400 MHz, DMSO) 0.23-0.26(2H, m), 0.43-0.47(2H, m), 0.98-1.08(1H, m), 2.39(3H, s), 3.16(2H, t, J 6.5 Hz), 6.33-6.34(1H, m), 6.86(2H, s), 7.19(1H, d, J 3.5 Hz), 7.34(1H, s) and 8.36(1H, t, J 6.0 Hz); M/Z 273(M+H)⁺ |
| 138 | J | 52 | IR $v_{max}$ (DR)/cm⁻¹ 3353, 3178, 2873, 1949, 1676, 1530, 1359, 1218, 1133, 1023, 753 and 699; NMR $\delta_H$ (400 MHz, DMSO) 2.39(3H, s), 2.85(2H, t, J 7.5 Hz), 3.50-3.55(2H, m), 6.33-6.34(1H, m), 6.81(2H, s), 7.19-7.31(6H, m), 7.33(1H, s) and 8.40(1H, t, J 6.0 Hz); M/Z 323(M+H)⁺ |
| 139 | J | 55 | IR $v_{max}$ (DR)/cm⁻¹ 3317, 3188, 2930, 2859, 1673, 1634, 1518, 1468, 1358, 1216, 1133, 1021 and 776; NMR $\delta_H$ (400 MHz, DMSO) 1.83(2H, pent, J 7.5 Hz), 2.39(3H, s), 2.62(2H, t, J 7.5 Hz), 3.27-3.33(2H, m), 6.33-6.34(1H, m), 6.81(2H, s), 7.16-7.30(6H, m), 7.33(1H, s) and 8.40(1H, t, J 6.0 Hz); M/Z 337(M+H)⁺ |
| 140 | J | 39 | IR $v_{max}$ (DR)/cm⁻¹ 3324, 3205, 2932, 1633, 1522, 1452, 1377, 1217, 1020, 976 and 784; NMR $\delta_H$ (400 MHz, DMSO) 60:40 mixture of rotamers: 0.81-0.87(2H, m), 1.03-1.09(3H, m), 2.36(1.2H, s), 2.37(1.8H, s), 4.54(0.8H, s), 4.65(1.2H, s), 6.30-6.31(0.4H, m), 6.32-6.33(0.6H, m), 6.89-6.90(3H, m), 7.14(0.4H, d, J 3.5 Hz), 7.19(0.6H, d, J 3.5 Hz) and 7.28-7.40(5H, m); M/Z 337(M+H)⁺ |
| 141 | J | 65 | IR $v_{max}$ (DR)/cm⁻¹ 3322, 3193, 2965, 2932, 1673, 1632, 1585, 1523, 1470, 1360, 1218, 1133, 1021 and 777; NMR $\delta_H$ (400 MHz, DMSO) |

TABLE 2-continued

| Example | Method | Yield (%) | Physical Data |
|---|---|---|---|
| | | | 0.87(3H, t, J 7.5 Hz), 1.81-1.94(2H, m), 2.38(3H, s), 4.90(1H, q, J 8.0 Hz), 6.32-6.33(1H, m), 6.88(2H, s), 7.19(1H, d, J 3.0 Hz), 7.24-7.28(1H, m), 7.30(1H, s), 7.32-7.40(4H, m) and 8.54(1H, d, J 8.5 Hz); M/Z 337(M+H)+ |
| 142 | J | 4 | IR $v_{max}$ (DR)/cm$^{-1}$ 3376, 3322, 3181, 2926, 1738, 1678, 1634, 1586, 1524, 1340, 1219, 1134, 1021 and 775; NMR $\delta_H$ (400 MHz, DMSO) 2.14(3H, s), 2.39(3H, s), 3.39(3H, s), 4.45(2H, d, J 6.0 Hz), 5.69(1H, d, J 3.0 Hz), 5.89(1H, d, J 3.0 Hz), 6.33-6.34(1H, m), 6.90(2H, s), 7.20(1H, d, J 3.0 Hz), 7.36(1H, s) and 8.19(1H, t, J 6.0 Hz); M/Z 326(M+H)+ |
| 143 | J | 23 | IR $v_{max}$ (DR)/cm$^{-1}$ 3189, 2977, 1678, 1529, 1362, 1217, 1129, 1023, 774 and 699; NMR $\delta_H$ (400 MHz, DMSO) 1.51(3H, d, J 7.0 Hz), 2.38(3H, s), 5.13(1H, pent, J 7.5 Hz), 6.33-6.34(1H, m), 6.89(2H, s), 7.19(1H, d, J 3.5 Hz), 7.24-7.28(1H, m), 7.31(1H, s), 7.33-7.41(4H, m) and 8.54(1H, d, J 8.0 Hz); M/Z 323(M+H)+ |
| 144 | J | 18 | IR $v_{max}$ (DR)/cm$^{-1}$ 3324, 2979, 1633, 1520, 1403, 1310, 1218, 1110, 1019, 786 and 700; NMR $\delta_H$ (400 MHz, DMSO) 1:1 mixture of rotamers: 1.55(3H, t, J 6.5 Hz), 2.37(3H, s), 2.61(3H, d, J 2.0 Hz), 5.03(0.5H, q, J 7.0 Hz), 5.88(0.5H, q, J 7.0 Hz), 6.31-6.33(1H, m), 6.87(0.5H, s), 6.89(2H, s), 6.95(0.5H, s), 7.17-7.18(1H, m) and 7.26-7.42(5H, m); M/Z 337(M+H)+ |
| 145 | J | 31 | IR $v_{max}$ (DR)/cm$^{-1}$ 4055, 3348, 3196, 2975, 1674, 1523, 1362, 1216, 1019, 849 and 778; NMR $\delta_H$ (400 MHz, DMSO) 1.71(6H, s), 2.37(3H, s), 6.32-6.33(1H, m), 6.98(2H, s), 7.18(1H, d, J 3.0 Hz), 7.22(1H, tt, J 7.5, 2.0 Hz), 7.26(1H, s), 7.30-7.34(2H, m), 7.39-7.42(2H, m) and 8.33(1H, s); M/Z 337(M+H)+ |
| 146 | J | 35 | IR $v_{max}$ (DR)/cm$^{-1}$ 3380, 3187, 2955, 2869, 1678, 1533, 1469, 1369, 1218, 1133, 1022 and 731; NMR $\delta_H$ (400 MHz, DMSO) 0.89(6H, d, J 6.5 Hz), 1.83(1H, sept, J 6.5 Hz), 2.39(3H, s), 3.13(2H, d, J 6.5 Hz), 6.33-6.34(1H, m), 6.84(2H, s), 7.19(1H, d, J 3.5 Hz), 7.33(1H, s) and 8.31(1H, t, J 6.5 Hz); M/Z 275(M+H)+ |
| 147 | J | 41 | IR $v_{max}$ (DR)/cm$^{-1}$ 3378, 3190, 2928, 2857, 2236, 1636, 1466, 1383, 1216, 1133, 10224, 854 and 777; NMR $\delta_H$ (400 MHz, DMSO) 0.87(3H, t, J 7.0 Hz), 1.25-1.31(6H, m), 1.47-1.54(2H, m), 2.39(3H, s), 3.25-3.29(2H, m), 6.33-6.34(1H, m), 6.81(2H, s), 7.19(1H, d, J 3.0 Hz), 7.32(1H, s) and 8.32(1H, t, J 6.0 Hz); M/Z 303(M+H)+ |
| 148 | J | 19 | IR $v_{max}$ (DR)/cm$^{-1}$ 2958, 1521, 1261, 1211, 1137, 1034 and 800; NMR $\delta_H$ (400 MHz, DMSO) 1:1 mixture of rotamers: 0.77(1.5H, t, J 7.5 Hz), 0.93(1.5H, t, J 7.5 Hz), 1.06-1.58(4H, m), 2.38(3H, s), 2.91(1.5H, s), 2.93(1.5H, s), 3.24(1H, t, J 7.5 Hz), 3.41(1H, t, J 7.5 Hz), 5.28(2H, s), 6.34-6.36(1H, m), 6.88(0.5H, s), 6.89(0.5H, s), 7.24(0.5H, d, J 3.5 Hz) and 7.26(0.5H, d, J 3.5 Hz); M/Z 289(M+H)+ |
| 149 | J | 58 | IR $v_{max}$ (DR)/cm$^{-1}$ 3371, 3194, 2875, 2330, 1667, 1566, 1498, 1415, 1320, 1226, 1131, 1030 and 792; NMR $\delta_H$ (400 MHz, DMSO) 1:1 mixture of rotamers: 0.78(1.5H, t, J 7.5 Hz), 0.90(1.5H, t, J 7.5 Hz), 1.04-1.19(2H, m), 1.24-1.38(2H, m), 1.49-1.59(2H, m), 2.36(3H, s), 2.89(1.5H, s), 2.93(1.5H, s), 3.22(1H, t, J 7.5 Hz), 3.39(1H, t, J 7.5 Hz), 6.31-6.32(1H, m), 6.81(0.5H, s), 6.82(0.5H, s), 6.82(1H, s), 6.85(1H, s) and 7.15-7.16(1H, m); M/Z 303(M+H)+ |
| 150 | J | 38 | IR $v_{max}$ (DR)/cm$^{-1}$ 3381, 3200, 1674, 1516, 1467, 1359, 1217, 1131 and 1022; NMR $\delta_H$ (400 MHz, DMSO) 2.39(3H, s), 4.49(2H, d, J 6.3 Hz), 6.34(1H, dd, J 3.4, 0.9 Hz), 6.87(2H, br s), 7.21(1H, d, J 3.4 Hz), 7.23-7.26(1H, m), 7.29-7.36(5H, m) and 8.82(1H, t, J 6.3 Hz); M/Z 309(M+H)+ |
| 151 | J | 84 | IR $v_{max}$ (DR)/cm$^{-1}$ 3324, 3183, 1686, 1540, 1359, 1220, 1136 and 1021; NMR $\delta_H$ (400 MHz, DMSO) 2.40(3H, s), 6.35-6.36(1H, m), 6.96(2H, br s), 7.15(1H, t, J 7.4 Hz), 7.25(1H, d, J 3.6 Hz), 7.37-7.42(3H, m), 7.79(2H, d, J 7.2 Hz) and 10.22(1H, s); M/Z 295(M+H)+ |
| 152 | J | 80 | IR $v_{max}$ (DR)/cm$^{-1}$ 3460, 3349, 3216, 2922, 1680, 1614, 1454, 1357, 1278, 1219, 1191, 1158, 1137 and 1039; NMR $\delta_H$ (400 MHz, DMSO) 2.47(3H, s), 4.50(2H, d, J 6.4 Hz), 7.08(2H, br s), 7.26-7.28(1H, m), 7.33-7.34(4H, m), 7.56(1H, d, J 0.8 Hz), 7.72(1H, s) and 8.85(1H, t, J 6.0 Hz); M/Z 326(M+H)+ |
| 153 | J | 13 | IR $v_{max}$ (DR)/cm$^{-1}$ 3566, 3196, 2947, 2135, 1633, 1402, 1359, 1218, 1134, 1026, 938 and 774; NMR $\delta_H$ (400 MHz, DMSO) 2.39(3H, s), 3.82(3H, s), 4.54(2H, d, J 6.0 Hz), 6.17(1H, d, J 2.0 Hz), 6.33-6.34(1H, m), 6.84(2H, s), 7.21(1H, d, J 3.5 Hz), 7.31(1H, d, J 2.0 Hz), 7.35(1H, s) and 8.73(1H, t, J 6.0 Hz); M/Z 313(M+H)+ |
| 154 | J | 15 | IR $v_{max}$ (DR)/cm$^{-1}$ 3463, 3352, 3223, 3075, 2924, 1674, 1616, 1556, 1455, 1421, 1356, 1280, 851 and 800; NMR $\delta_H$ (400 MHz, DMSO) 2.47(3H, d, J 1.0 Hz), 3.82(3H, s), 4.56(2H, d, J 6.0 Hz), 6.18(1H, d, J 1.5 Hz), 7.09(2H, s), 7.31(1H, d, J 2.0 Hz), 7.56(1H, d, J 1.0 Hz), 7.70(1H, s) and 8.79(1H, t, J 6.0 Hz); M/Z 330(M+H)+ |
| 155 | J | 44 | IR $v_{max}$ (DR)/cm$^{-1}$ 3457, 3388, 3349, 3225, 3070, 1673, 1446, 1413, 1379, 1359, 1289, 1265, 1215, 1169 and 1144; NMR $\delta_H$ (400 MHz, DMSO) 2.47(3H, s), 4.63(2H, d, J 6.0 Hz), 7.14(2H, br s), 7.28-7.32(1H, m), 7.36(1H, d, J 7.6 Hz), 7.56(1H, d, J 0.8 Hz), 7.74(1H, s), |

TABLE 2-continued

| Example | Method | Yield (%) | Physical Data |
|---|---|---|---|
| | | | 7.78(1H, dd, J 7.6, 1.6 Hz), 8.54(1H, d, J 5.2 Hz) and 9.98(1H, t, J 6.0 Hz); M/Z 327(M+H)$^+$ |
| 156 | J | 55 | IR $v_{max}$ (DR)/cm$^{-1}$ 3462, 3407, 3351, 3222, 3108, 1671, 1509, 1451, 1355, 1312, 1254, 1171, 1125, 1061, 1041 and 1015; NMR $\delta_H$ (400 MHz, DMSO) 2.47(3H, s), 4.70(2H, d, J 6.0 Hz), 7.11(2H, br s), 7.47-7.53(2H, m), 7.56(1H, d, J 1.2 Hz), 7.65(1H, s), 7.65-7.69(1H, m), 7.72-7.76(1H, m) and 8.96(1H, t, J 6.0 Hz); M/Z 394(M+H)$^+$ |
| 157 | J | 28 | IR $v_{max}$ (DR)/cm$^{-1}$ 3363, 3230, 3098, 1681, 1646, 1519, 1455, 1360, 1321, 1236, 1210 and 1110; NMR $\delta_H$ (400 MHz, DMSO) 2.20(3H, s), 2.47(3H, s), 3.67(3H, s), 4.37(2H, d, J 6.0 Hz), 7.12(2H, br s), 7.56(1H, s), 7.71(1H, s) and 8.47(1H, t, J 6.0 Hz); M/Z 343(M+H)$^+$ |
| 158 | J | 5 | IR $v_{max}$ (DR)/cm$^{-1}$ 3329, 3219, 2939, 1628, 1521, 1217, 1129, 1023, 860 and 777; NMR $\delta_H$ (400 MHz, DMSO) 2.39(3H, s), 3.80(3H, s), 4.43(2H, d, J 6.0 Hz), 6.15(1H, d, J 2.0 Hz), 6.33-6.34(1H, m), 6.87(2H, s), 7.20(1H, d, J 3.5 Hz), 7.36(1H, s), 7.60(1H, d, J 2.0 Hz) and 8.48(1H, t, J 6.0 Hz); M/Z 313(M+H)$^+$ |
| 159 | J | 9 | IR $v_{max}$ (DR)/cm$^{-1}$ 3413, 3375, 3298, 3196, 3105, 2934, 1732, 1675, 1634, 1557, 1519, 1446, 1358, 1326, 1219, 868 and 785; NMR $\delta_H$ (400 MHz, DMSO) 2.47(3H, d, J 1.0 Hz), 3.80(3H, s), 4.44(2H, d, J 5.5 Hz), 6.16(1H, d, J 2.0 Hz), 7.12(2H, s), 7.55-7.56(1H, m), 7.60(1H, d, J 2.0 Hz), 7.72(1H, s) and 8.53(1H, t, J 6.0 Hz); M/Z 330(M+H)$^+$ |
| 160 | J | 68 | NMR $\delta_H$ (400 MHz, CDCl$_3$) 2.25(3H, s), 2.45(3H, s), 3.77(3H, s), 4.87(2H, d, J 5.7 Hz), 6.04(1H, d, J 3.5 Hz), 6.22(1H, d, J 3.5 Hz), 7.25(1H, d, J 3.5 Hz), 8.34(1H, s), 8.39(1H, br s), and 9.08(1H, s); M/Z 312(M+H)$^+$; LC 2.13 min. (Method AM). |
| 161 | J | 63 | NMR $\delta_H$ (400 MHz, CDCl$_3$) 2.38(3H, s), 4.79(2H, d, J 6.4 Hz), 6.16(1H, d, J 3.3 Hz), 7.20(1H, d, J 3.3 Hz), 7.32(1H, t, J 7.6 Hz), 7.47(1H, t, J 7.6 Hz), 7.56(1H, d, J 7.7 Hz), 7.62(1H, d, J 7.8 Hz), 8.26(1H, s), 8.31(1H, br s) and 9.00(1H, s); M/Z 362(M+H)$^+$; LC 2.72 min. (Method AM). |
| 162 | J | 68 | NMR $\delta_H$ (400 MHz, CDCl$_3$) 2.38(3H, s), 4.62(2H, d, J 6.1 Hz), 6.16(1H, d, J 3.3 Hz), 7.20(1H, d, J 3.4 Hz), 7.31-7.23(5H, m), 8.25(1H, br s), 8.27(1H, s) and 8.99(1H, s); M/Z 294(M+H)$^+$; LC 2.55 min. (Method AM). |
| 163 | J | 12 | IR $v_{max}$ (DR)/cm$^{-1}$ 3322, 3199, 1678, 1627, 1462, 1379, 1217, 1127 and 1022; NMR $\delta_H$ (400 MHz, DMSO) 1.17(6H, d, J 6.4 Hz), 2.39(3H, s), 3.71(1H, pent, J 6.0 Hz), 4.55(2H, s), 4.58(2H, d, J 6.0 Hz), 6.34(1H, dd, J 3.6, 0.8 Hz), 6.87(2H, br s), 7.21(1H, d, J 3.2 Hz), 7.23(1H, s), 7.32(1H, d, J 7.6 Hz), 7.36(1H, d, J 7.6 Hz), 7.77(1H, t, J 7.8 Hz) and 8.95(1H, t, J 6.0 Hz); M/Z 382(M+H)$^+$ |
| 164 | J | 65 | NMR $\delta_H$ (400 MHz, CDCl$_3$) 2.38(3H, s), 4.75(2H, d, J 5.5 Hz), 6.16(1H, d, J 3.4 Hz), 7.20-7.16(2H, m), 7.28(1H, d, J 7.8 Hz), 7.64(1H, td, J 7.7, 1.8 Hz), 8.26(1H, s), 8.57-8.55(1H, m), 8.95(1H, br s) and 9.07(1H, s); M/Z 295(M+H)$^+$; LC 2.04 min. (Method AM). |
| 165 | J | | NMR $\delta_H$ (400 MHz, CDCl$_3$) 2.25(3H, s), 2.39(3H, s), 2.54(3H, s), 4.64(2H, d, J 6.1 Hz), 6.17(1H, s), 6.98-6.94(1H, m), 7.32-7.30(1H, m), 8.24(1H, s), 9.13(1H, s) and 9.55(1H, s); M/Z 323(M+H)$^+$; LC 2.05 min. (Method AM). |
| 166 | J | 30 | IR $v_{max}$ (DR)/cm$^{-1}$ 3319, 3196, 2925, 1679, 1632, 1526, 1470, 1359, 1216, 1133, 1022 and 776; NMR $\delta_H$ (400 MHz, DMSO) 2.08(3H, s), 2.39(3H, s), 3.72(3H, s), 4.47(2H, d, J 6.0 Hz), 5.94(1H, s), 6.33-6.34(1H, m), 6.82(2H, s), 7.20(1H, d, J 3.5 Hz), 7.34(1H, s) and 8.66(1H, d, J 6.0 Hz); M/Z 327(M+H)$^+$ |
| 167 | J | 4 | IR $v_{max}$ (DR)/cm$^{-1}$ 3553, 3413, 3316, 3206, 2923, 1631, 1555, 1462, 1359, 1227, 1021, 976, 867 and 704; NMR $\delta_H$ (400 MHz, DMSO) 2.08(3H, s), 2.47(3H, d, J 1.0 Hz), 3.72(3H, s), 4.49(2H, d, J 6.0 Hz), 5.95(1H, s), 7.07(2H, s), 7.55(1H, d, J 1.0 Hz), 7.70(1H, s) and 8.72(1H, t, J 6.0 Hz); M/Z 344(M+H)$^+$ |
| 168 | J | 44 | IR $v_{max}$ (DR)/cm$^{-1}$ 3533, 3193, 2173, 1731, 1469, 1217, 1133, 1023, 860 and 774; NMR $\delta_H$ (400 MHz, DMSO) 2.39(3H, s), 2.48(3H, s), 4.55(2H, d, J 6.0 Hz), 6.34-6.35(1H, m), 6.88(2H, s), 7.14(2H, t, J 8.0 Hz), 7.21(1H, d, J 3.0 Hz), 7.37(1H, s), 7.65(1H, t, J, 7.5 Hz) and 8.92(1H, t, J 6.0 Hz); M/Z 324(M+H)$^+$ |
| 169 | J | 10 | IR $v_{max}$ (DR)/cm$^{-1}$ 3516, 3392, 3176, 2921, 2234, 1519, 1470, 1404, 1243, 1216, 1135, 1025 and 768; NMR $\delta_H$ (400 MHz, DMSO) 2.39(3H, s), 3.79(3H, s), 4.30(2H, d, J 6.0 Hz), 6.33-6.34(1H, m), 6.82(2H, s), 7.19(1H, d, J 3.0 Hz), 7.34(1H, s), 7.37(1H, s), 7.62(1H, s) and 8.47(1H, t, J 6.0 Hz); M/Z 313(M+H)$^+$ |
| 170 | J | 8 | IR $v_{max}$ (DR)/cm$^{-1}$ 3321, 3184, 2921, 1733, 1690, 1644, 1589, 1550, 1456, 1355, 1261, 995 and 748; NMR $\delta_H$ (400 MHz, DMSO) 2.47(3H, d, J 1.0 Hz), 4.62(2H, d, J 6.0 Hz), 7.17(2H, s), 7.45-7.46(1H, m), 7.58(1H, d, J 1.0 Hz), 7.72(1H, s), 8.74(1H, d, J 5.0 Hz) and 9.11-9.14(2H, m); M/Z 328(M+H)$^+$ |
| 171 | J | 14 | IR $v_{max}$ (DR)/cm$^{-1}$ 3569, 3470, 3348, 2924, 1671, 1622, 1451, 1346, 1226, 1138, 854 and 737; NMR $\delta_H$ (400 MHz, DMSO) 2.34(3H, d, J 1.0 Hz), 2.47(3H, d, J 1.0 Hz), 4.73(2H, d, J 6.0 Hz), 7.16-7.17(3H, m), 7.58(1H, s), 7.71(1H, s) and 9.22(1H, t, J 6.0 Hz); M/Z 347(M+H)$^+$ |

TABLE 2-continued

| Example | Method | Yield (%) | Physical Data |
|---|---|---|---|
| 172 | J | 6 | IR $\nu_{max}$ (DR)/cm$^{-1}$ 3527, 3327, 3219, 2922, 1685, 1633, 1561, 1490, 1469, 1355, 1223 and 737; NMR $\delta_H$ (400 MHz, DMSO) 2.24(3H, s), 2.47(3H, d, J 1.0 Hz), 3.69(3H, s), 4.28(2H, d, J 5.5 Hz), 7.08(2H, s), 7.31(1H, s), 7.55(1H, d, J 1.0 Hz), 7.70(1H, s) and 8.40(1H, t, J 6.0 Hz); M/Z 344(M+H)$^+$ |
| 173 | J | 29 | IR $\nu_{max}$ (DR)/cm$^{-1}$ 3568, 3495, 3414, 3318, 3210, 3073, 2921, 1733, 1631, 1519, 1356, 1226, 1177, 977 and 703; NMR $\delta_H$ (400 MHz, DMSO) 2.12(3H, s), 2.47(3H, d, J 1.0 Hz), 3.71(3H, s), 4.28(2H, d, J 5.5 Hz), 7.09(2H, s), 7.53(1H, s), 7.55(1H, d, J 1.0 Hz), 7.71(1H, s) and 8.38(1H, t, J 6.0 Hz); M/Z 344(M+H)$^+$ |
| 174 | J | 12 | IR $\nu_{max}$ (DR)/cm$^{-1}$ 3557, 3462, 3347, 2932, 2161, 1623, 1557, 1454, 1358, 1271, 1238, 1137, 1034, 868 and 705; NMR $\delta_H$ (400 MHz, DMSO) 2.47(3H, s), 4.52(2H, d, J 6.0 Hz), 7.06(2H, s), 7.36(1H, dd, J 7.5, 4.5 Hz), 7.56(1H, J 1.0 Hz), 7.71(1H, s), 7.73(1H, dt, J 8.0 Hz, 2.0 Hz), 8.47(1H, dd, J 5.0, 1.5 Hz), 8.56(1H, d, J 2.0 Hz) and 9.01(1H, t, J 6.5 Hz); M/Z 327(M+H)$^+$ |
| 175 | J | 68 | IR $\nu_{max}$ (DR)/cm$^{-1}$ 3619, 3518, 3321, 3219, 2927, 1674, 1632, 1517, 1450, 1331, 1166, 1110, 1074, 977, 865 and 701; NMR $\delta_H$ (400 MHz, DMSO) 2.47(3H, d, J 1.0 Hz), 4.58(2H, d, J 6.5 Hz), 7.06(2H, s), 7.56(1H, d, J 1.0 Hz), 7.58-7.66(3H, m), 7.69(1H, s), 7.71(1H, s) and 9.08(1H, t, J 6.0 Hz); M/Z 394(M+H)$^+$ |
| 176 | J | 42 | IR $\nu_{max}$ (DR)/cm$^{-1}$ 3471, 3363, 3218, 3113, 2923, 2724, 1952, 1732, 1681, 1557, 1359, 1277, 1140, 977, 855 and 754; NMR $\delta_H$ (400 MHz, DMSO) 2.32(3H, s), 2.47(3H, d, J 1.0 Hz), 4.50(2H, d, J 6.0 Hz), 7.11(2H, s), 7.15-7.20(3H, m), 7.24-7.26(1H, m), 7.56(1H, d, J 1.0 Hz), 7.72(1H, s) and 8.63(1H, t, J 6.0 Hz); M/Z 340(M+H)$^+$ |
| 177 | J | 6 | IR $\nu_{max}$ (DR)/cm$^{-1}$ 3331, 3225, 2925, 1671, 1626, 1519, 1455, 1359, 1203 1122 and 780; NMR $\delta_H$ (400 MHz, DMSO) 2.47(3H, d, J 1.0 Hz), 3.38(3H, s), 4.51(2H, s), 4.60(2H, d, J 6.0 Hz), 7.13(2H, s), 7.25(1H, d, J 7.5 Hz), 7.31(1H, d, J 7.5 Hz), 7.56(1H, d, J 1.0 Hz), 7.73(1H, s), 7.79(1H, t, J 8.0 Hz) and 9.01(1H, t, J 6.0 Hz); M/Z 371(M+H)$^+$ |
| 178 | J | 58 | IR $\nu_{max}$ (DR)/cm$^{-1}$ 3616, 3513, 3322, 3215, 2921, 2009, 1632, 1488, 1355, 1267, 1155, 1045, 864 and 739; NMR $\delta_H$ (400 MHz, DMSO) 2.47(3H, s), 3.74(3H, s), 4.48(2H, d, J 6.5 Hz), 6.82-6.85(1H, m), 6.89-6.91(2H, m), 7.08(2H, s), 7.25(1H, t, J 8.0 Hz), 7.56(1H, d, J 1.0 Hz), 7.72(1H, s) and 8.82(1H, t, J 6.5 Hz); M/Z 356(M+H)$^+$ |
| 179 | J | 60 | IR $\nu_{max}$ (DR)/cm$^{-1}$ 3609, 3506, 3401, 3321, 3104, 2920, 1937, 1734, 1633, 1519, 1353, 1245, 1099, 976, 864 and 740; NMR $\delta_H$ (400 MHz, DMSO) 2.29(3H, s), 2.47(3H, d, J 1.0 Hz), 4.46(2H, d, J 1.0 Hz), 7.07-7.14(5H, m), 7.22(1H, t, J 7.5 Hz), 7.56(1H, d, J 1.0 Hz), 7.72(1H, s) and 8.80(1H, t, J 6.0 Hz); M/Z 340(M+H)$^+$ |
| 180 | J | 30 | IR $\nu_{max}$ (DR)/cm$^{-1}$ 3618, 3511, 3207, 2922, 2737, 2228, 2013, 1929, 1522, 1355, 1245, 1141, 976, 863 and 753; NMR $\delta_H$ (400 MHz, DMSO) 2.47(3H, s), 4.51(2H, d, J 6.5 Hz), 7.06-7.18(5H, m), 7.36-7.41(1H, m), 7.56(1H, d, J 1.0 Hz), 7.71(1H, s) and 8.97(1H, t, J 6.5 Hz); M/Z 344(M+H)$^+$ |
| 181 | J | 26 | IR $\nu_{max}$ (DR)/cm$^{-1}$ 3602, 3504, 3403, 3315, 3198, 2925, 1944, 1636, 1559, 1354, 1245, 1079, 977, 864 and 705; NMR $\delta_H$ (400 MHz, DMSO) 2.47(3H, d, J 1.0 Hz), 4.50(2H, d, J 6.5 Hz), 7.07(2H, s), 7.28-7.39(4H, m), 7.56(1H, d, J 1.0 Hz), 7.71(1H, s) and 8.99(1H, t, J 6.5 Hz); M/Z 360(M+H)$^+$ |
| 182 | J | 19 | IR $\nu_{max}$ (DR)/cm$^{-1}$ 3551, 3461, 3339, 1624, 1458, 1361, 1275, 1029, 1000, 847 and 768; NMR $\delta_H$ (400 MHz, DMSO) 2.47(3H, d, J 1.0 Hz), 2.49(3H, s), 4.57(2H, d, J 6.0 Hz), 7.12-7.16(4H, m), 7.56(1H, d, J 1.0 Hz), 7.66(1H, t, J 7.5 Hz), 7.73(1H, s) and 8.97(1H, t, J 6.0 Hz) |
| 183 | J | 18 | NMR $\delta_H$ (400 MHz, CDCl$_3$) 4.69, (2H, d, J 6.0 Hz), 6.96(2H, br s), 7.54(5H, m), 7.61(1H, s), 7.66(1H, t, J 7.4 Hz), 7.75(1H, d, J 7.4 Hz), 8.12(2H, m), and 9.03(1H, t, J 6.0 Hz); M/Z 373(M+H)$^+$; LC 2.68 min. (Method AM). |
| 184 | J | 27 | NMR $\delta_H$ (400 MHz, CDCl$_3$) 4.63(2H, d, J 6.0 Hz), 6.99(2H, br s), 7.30(1H, m), 7.36(1H, d, J 7.8 Hz), 7.53(1H, d, J 2.2 Hz), 7.54(2H, d, J 1.7 Hz), 7.62(1H, s), 7.79(1H, dt, J 1.7, 4.2 Hz), 8.13(2H, m), 8.54(1H, m) and 9.03(1H, t, J 6.0 Hz); M/Z 306(M+H)$^+$; LC 2.03 min. (Method AM). |
| 185 | J | 36 | NMR $\delta_H$ (400 MHz, CDCl$_3$) 2.37(3H, s), 4.62(2H, d, J 5.9 Hz), 6.97(2H, br s), 7.18(1H, s), 7.33(5H, m), 7.42(1H, m), 7.78(1H, dt, J 1.8, 7.7 Hz), 8.54(1H, m) and 9.03(1H, t, J 5.9 Hz); M/Z 320(M+H)$^+$; LC 2.06 min. (Method AM). |
| 186 | J | 25 | NMR $\delta_H$ (400 MHz, CDCl$_3$) 2.34(3H, s), 4.63(2H, d, J 6.0 Hz), 6.94(2H, br s), 7.30(4H, m), 7.59(1H, s), 7.80(1H, dt, J 1.9, 3.4 Hz), 8.03(2H, d, J 7.8 Hz), 8.53(1H, m) and 9.01(1H, t, J 6.0 Hz); M/Z 320(M+H)$^+$; LC 2.17 min. (Method AM). |
| 187 | J | 16 | NMR $\delta_H$ (400 MHz, CDCl$_3$) 4.63(2H, d, J 5.9 Hz), 7.22(2H, br s), 7.29(1H, dd, J 1.1, 7.5 Hz), 7.34(1H, d, J 8.2 Hz), 7.74(1H, s), 7.77(2H, m), 8.18(1H, dt, J 1.4, 6.5 Hz), 8.45(1H, m), 8.54(1H, m), 8.58(1H, m) and 9.05(1H, t, J 5.9 Hz); M/Z 331(M+H)$^+$; LC 2.01 min. (Method AM) |

TABLE 2-continued

| Example | Method | Yield (%) | Physical Data |
|---|---|---|---|
| 188 | J | 42 | NMR δ$_H$ (400 MHz, CDCl$_3$) 2.32(3H, s), 2.37(3H, s), 4.63(2H, d, J 5.9 Hz), 7.05(2H, br s), 7.21(1H, s), 7.28(2H, m), 7.32(1H, d, J 0.7 Hz), 7.35(1H, m), 7.43(1H, m), 7.64(1H, m), 8.41(1H, dd, J 1.0, 4.8 Hz) and 9.10(1H, t, J 5.9 Hz); M/Z 334(M+H)$^+$; LC 2.12 min. (Method AM). |
| 189 | J | 42 | NMR δ$_H$ (400 MHz, CDCl$_3$) 2.33(3H, s), 2.40(3H, s), 4.64(2H, d, J 5.9 Hz), 7.05(2H, br s), 7.27(2H, dd, J 4.7, 7.6 Hz), 7.36(2H, m), 7.64(1H, s), 7.91(1H, d, J 7.6 Hz), 7.96(1H, br s), 8.42(1H, dd, J 0.9, 4.7 Hz) and 9.11(1H, t, J 5.9 Hz); M/Z 334(M+H)$^+$; LC 2.26 min. (Method AM). |
| 190 | J | 18 | NMR δ$_H$ (400 MHz, CDCl$_3$) 2.33(3H, s), 2.38(3H, s), 4.62(2H, d, J 6.0 Hz), 7.02(2H, br s), 7.27(1H, dd, J 4.8, 7.4 Hz), 7.32(2H, d, J 8.2 Hz), 7.62(1H, s), 7.64(1H br s), 8.04(2H, d, J 8.2 Hz), 8.41(1H, d, J 3.8 Hz) and 9.11(1H, t, J 6.0 Hz); M/Z 334(M+H)$^+$; LC 2.25 min. (Method AM). |
| 191 | J | 24 | NMR δ$_H$ (400 MHz, CDCl$_3$) 2.33(3H, s), 4.64(2H, d, J 5.9 Hz), 7.19(2H, br s), 7.27(1H, dd, J 4.9, 7.5 Hz), 7.64(1H, d, J 7.5 Hz), 7.74(1H, t, J 7.8 Hz), 7.76(1H, s), 8.01(1H, d, J 7.8 Hz), 8.41(1H, d, J 3.9 Hz), 8.47(1H, d, J 8.1 Hz), 8.59(1H, br s) and 9.13(1H, t, J 5.9 Hz); M/Z 345(M+H)$^+$; LC 2.07 min. (Method AM). |
| 192 | J | 11 | NMR δ$_H$ (400 MHz, CDCl$_3$); 2.39(3H, s), 4.63(2H, d, J 5.9 Hz), 6.96(2H, br s), 7.35(4H, m), 7.61(1H, s), 7.77(1H, dt, J 1.8, 7.7 Hz), 7.91(1H, d, J 7.7 Hz), 7.96(1H, br s), 8.54(1H, d, J 4.3 Hz) and 9.02(1H, t, J 5.9 Hz); M/Z 320(M+H)$^+$; LC 2.18 min. (Method AM). |
| 193 | J | 5 | NMR δ$_H$ (400 MHz, CDCl$_3$) 3.84(3H, s), 4.62(2H, d, J 5.9 Hz), 7.00(2H, br s), 7.12(1H, dd, J 1.7, 7.6 Hz), 7.29(1H, dd, J 0.6, 4.8 Hz), 7.36(1H, d, J 7.9 Hz), 7.44(1H, t, J 7.9 Hz), 7.61(1H, s), 7.66(2H, m), 7.77(1H, dt, J 1.7, 7.6 Hz), 8.53(1H, dd, J 0.6, 4.8 Hz) and 9.03(1H, t, J 5.9 Hz); M/Z 336(M+H)$^+$; LC 2.07 min. (Method AM). |
| 194 | J | 4 | NMR δ$_H$ (400 MHz, CDCl$_3$) 2.33(3H, s), 3.84(3H, s), 4.62(2H, d, J 5.9 Hz), 7.07(2H, br s), 7.11(1H, dd, J 1.5, 8.1 Hz), 7.27(1H, dd, J 4.6, 7.5 Hz), 7.44(1H, t, J 8.0 Hz), 7.63(1H, s), 7.66(2H, m), 7.68(1H, dt, J 1.3, 7.5 Hz), 8.41(1H, dd, J 1.0, 4.6 Hz) and 9.11(1H, t, J 5.9 Hz); M/Z 350(M+H)$^+$; LC 2.03 min. (Method AM). |
| 195 | J | 16 | NMR δ$_H$ (400MHz, CDCl$_3$) 2.33(3H, s), 4.63(2H, d, J 5.9 Hz), 7.07(2H, br s), 7.27(2H, dd, J 4.8, 7.5 Hz), 7.52(1H, d, J 1.8 Hz), 7.54(2H, d, J 1.8 Hz), 7.65(1H, s), 8.13(2H, m), 8.42(1H, d, J 3.9 Hz) and 9.12(1H, t, J 5.9 Hz); M/Z 320(M+H)$^+$; LC 1.98 min. (Method AM). |

Adenosine Receptor Binding

Binding Affinities at hA$_{2A}$ Receptors

The compounds were examined in an assay measuring in vitro binding to human adenosine A$_{2A}$ receptors by determining the displacement of the adenosine A$_{2A}$ receptor selective radioligand [$^3$H]-CGS 21680 using standard techniques.

In general, the compounds of the above examples have a K$_i$ of <5 μM in this assay, demonstrating binding affinity for the human adenosine A$_{2A}$ receptor.

By way of illustration only, the compound of Example 1 has a K$_i$ of <50 nM in this assay, demonstrating potent binding affinity for the human adenosine A$_{2A}$ receptor.

Evaluation of Potential Anti-Parkinsonian Activity In Vivo

Haloperidol-Induced Hypolocomotion Model

It has previously been demonstrated that adenosine antagonists, such as theophylline, can reverse the behavioural depressant effects of dopamine antagonists, such as haloperidol, in rodents (Mandhane S. N. et al., Adenosine A$_2$ receptors modulate haloperidol-induced catalepsy in rats. *Eur. J. Pharmacol.* 1997, 328, 135-141). This approach is also considered a valid method for screening drugs with potential antiparkinsonian effects. Thus, the ability of novel adenosine antagonists to block haloperidol-induced deficits in locomotor activity in mice can be used to assess both in vivo and potential antiparkinsonian efficacy.

Method

Female TO mice (25-30 g) obtained from Harlan, UK, are used for all experiments. Animals are housed in groups of 8 [cage size—40 (width)×40 (length)×20 (height) cm] under 12 h light/dark cycle (lights on 08:00 hr), in a temperature (20±2° C.) and humidity (55±15%) controlled environment. Animals have free access to food and water, and are allowed at least 3 days to acclimatize after delivery before experimental use.

Drugs

Liquid injectable haloperidol (1 ml Serenance ampoules from Baker Norton, Harlow, Essex, each containing haloperidol BP 5 mg) are diluted to a final concentration of 0.02 mg/ml using saline. Test compounds are typically prepared as aqueous suspensions in 1% methyl cellulose. All compounds are administered orally in a volume of 10 ml/kg.

Procedure 1.5 h before testing, mice are administered 0.2 mg/kg haloperidol, a dose that reduces baseline locomotor activity by at least 50%. Test substances are typically administered 5-60 min. prior to testing. The animals are then placed individually into clean, clear polycarbonate cages [20 (width)×40 (length)×20 (height) cm, with a flat perforated, Perspex lid]. Horizontal locomotor activity is determined by placing the cages within a frame containing a 4×7 array of photocells linked to a computer, which tabulates beam breaks. Mice are left undisturbed to explore for up to 1 h, and the number of beams breaks made during this period serves as a record of locomotor activity which is compared with data for control animals for statistically significant differences.

By way of illustration only, the compound of example 1 above is orally active in this model at a dose of 30 mg/kg:—

6-OHDA Model

An alternative model of Parkinson's Disease for assessment of the compounds of the invention is as follows.

Parkinson's disease is a progressive neurodegenerative disorder characterised by symptoms of muscle rigidity, tremor, paucity of movement (hypokinesia), and postural instability. It has been established for some time that the primary deficit in PD is a loss of dopaminergic neurones in the substantia nigra which project to the striatum, and indeed a substantial proportion of striatal dopamine is lost (ca 80-85%) before symptoms are observed. The loss of striatal dopamine results in abnormal activity of the basal ganglia, a series of nuclei which regulate smooth and well co-ordinated movement (Blandini F. et al., Glutamate and Parkinson's Disease. *Mol. Neurobiol.* 1996, 12, 73-94). The neurochemical deficits seen in Parkinson's disease can be reproduced by local injection of the dopaminergic neurotoxin 6-hydroxydopamine into brain regions containing either the cell bodies or axonal fibres of the nigrostriatal neurones.

By unilaterally lesioning the nigrostriatal pathway on only one-side of the brain, a behavioural asymmetry in movement inhibition is observed. Although unilaterally-lesioned animals are still mobile and capable of self maintenance, the remaining dopamine-sensitive neurones on the lesioned side become supersensitive to stimulation. This is demonstrated by the observation that following systemic administration of dopamine agonists, such as apomorphine, animals show a pronounced rotation in a direction contralateral to the side of lesioning. The ability of compounds to induce contralateral rotations in 6-OHDA lesioned rats has proven to be a sensitive model to predict drug efficacy in the treatment of Parkinson's Disease.

Animals

Male Sprague-Dawley rats, obtained from Charles River, are used for all experiments. Animals are housed in groups of 5 under 12 hr light/dark cycle (lights on 08:00 hr), in a temperature (20±2° C.) and humidity (55±15%) controlled environment. Animals have free access to food and water, and are allowed at least 7 days to acclimatize after delivery before experimental use.

Drugs

Ascorbic acid, desipramine, 6-OHDA and apomorphine (Sigma-Aldrich, Poole, UK). 6-OHDA is freshly prepared as a solution in 0.2% ascorbate at a concentration of 4 mg/mL prior to surgery. Desipramine is dissolved in warm saline, and administered in a volume of 1 ml/kg. Apomorphine is dissolved in 0.02% ascorbate and administered in a volume of 2 mL/kg. Test compounds are suspended in 1% methyl cellulose and injected in a volume of 2 mL/kg.

Surgery 15 minutes prior to surgery, animals are given an intraperitoneal injection of the noradrenergic uptake inhibitor desipramine (25 mg/kg) to prevent damage to non-dopamine neurones. Animals are then placed in an anaesthetic chamber and anaesthetised using a mixture of oxygen and isoflurane. Once unconscious, the animals are transferred to a stereotaxic frame, where anaesthesia is maintained through a mask. The top of the animal's head is shaved and sterilised using an iodine solution. Once dry, a 2 cm long incision is made along the midline of the scalp and the skin retracted and clipped back to expose the skull. A small hole is then drilled through the skull above the injection site. In order to lesion the nigrostriatal pathway, the injection cannula is slowly lowered to position above the right medial forebrain bundle at −3.2 mm anterior posterior, −1.5 mm medial lateral from bregma, and to a depth of 7.2 mm below the duramater. 2 minutes after lowing the cannula, 2 μL of 6-OHDA solution is infused at a rate of 0.5 μL/min over 4 minutes, yielding a final dose of 8 μg. The cannula is then left in place for a further 5 minutes to facilitate diffusion before being slowly withdrawn. The skin is then sutured shut using Ethicon W501 Mersilk, and the animal removed from the stereotaxic frame and returned to its homecage. The rats are allowed 2 weeks to recover from surgery before behavioural testing.

Apparatus

Rotational behaviour is measured using an eight station rotameter system provided by Med Associates, San Diego, USA. Each station is comprised of a stainless steel bowl (45 cm diameter×15 cm high) enclosed in a transparent Plexiglas cover running around the edge of the bowl, and extending to a height of 29 cm. To assess rotation, rats are placed in cloth jacket attached to a spring tether connected to optical rotameter positioned above the bowl, which assesses movement to the left or right either as partial (45°) or full (360°) rotations. All eight stations are interfaced to a computer that tabulated data.

Procedure

To reduce stress during drug testing, rats are initially habituated to the apparatus for 15 minutes on four consecutive days. On the test day, rats are given an intraperitoneal injection of test compound 30 minutes prior to testing. Immediately prior to testing, animals are given a subcutaneous injection of a subthreshold dose of apomorphine, then placed in the harness and the number of rotations recorded for one hour. The total number of full contralateral rotations during the hour test period serves as an index of antiparkinsonian drug efficacy.

The invention claimed is:

1. A compound of formula (I)

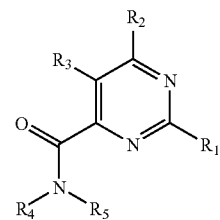

$R_1$ is H or $NH_2$;

$R_2$ is optionally substituted aryl or heteroaryl attached via a carbon atom;

$R_3$ is H; optionally substituted $C_1$-$C_6$ alkyl, $C_1$-$C_6$ alkenyl, $C_2$-$C_6$ alkynyl, or $C_3$-$C_7$ cycloalkyl, halogen; OH or $OR_{10}$;

$R_4$ is H, optionally substituted $C_1$-$C_6$ alkyl, $C_3$-$C_6$ alkenyl, $C_3$-$C_6$ alkynyl, $C_3$-$C_7$ cycloalkyl, aryl or heteroaryl, $R_5$ is H or optionally substituted $C_1$-$C_6$ alkyl, $C_2$-$C_6$ alkenyl, $C_1$-$C_6$ alkynyl, or $C_3$-$C_7$ cycloalkyl;

or $R_4$ and $R_5$ together form a 5 or 6-membered heterocyclic ring;

$R_{10}$ is optionally substituted $C_1$-$C_6$ alkyl;

wherein the term "substituted" means substituted with at least one substituent selected from $(C_1$-$C_6)$alkyl, $(C_1$-$C_6)$alkoxy, hydroxy, hydroxy$(C_1$-$C_6)$alkyl, mercapto, mercapto$(C_1$-$C_6)$alkyl, $(C_1$-$C_6)$alkylthio, halo, trifluoromethyl, trifluoromethoxy, nitro, nitrile (—CN), oxo, phenyl, monocyclic heterocyclic having 5- or 6 ring members, —COOH, —COO$R^4$, —CO$R^4$, —SO$_2$$R^4$, —CONH$_2$, —SO$_2$NH$_2$, —CONHR$^A$, —SO$_2$NHR$^A$, —CONR$^A$R$^B$, —SO$_2$NR$^A$R$^B$, —NH$_2$, —NHR$^A$, —NR$^A$R$^B$, —OCONH$_2$, —OCONHR$^A$, —OCONR$^A$R$^B$, —NHCOR$^A$, —NR$^B$COR$^A$, —NHCOOR$^A$, —NR$^B$COOR$^A$, —NHSO$_2$R$^A$, —NR$^B$SO$_2$R$^A$, —NHCONH$_2$, —NR$^A$CON H$_2$, —NHCONHR$^B$, —NR$^A$CONHR$^B$, —NHCONR$^A$R$^B$ or —NR$^A$CONR$^A$R$^B$ wherein R$^A$ and R$^B$ are independently a (C$_1$-C$_6$)alkyl group wherein phenyl or monocyclic heterocyclic having 5- or 6 ring members may be substituted by any of the foregoing except phenyl and monocyclic heterocyclic having 5- or 6 ring members; or a pharmaceutically acceptable salt thereof PROVIDED THAT: (a) R$_2$ is not an optionally substituted pyrazolopyridine ring system; and (b) when R$_1$ and R$_3$ are hydrogen and R$_2$ is unsubstituted phenyl then —NR$_4$R$_5$ is not —NH$_2$, NHCH$_3$ or N(CH$_3$)$_2$; and (c) when R$_1$ is —NH$_2$ and R$_3$ is hydrogen, then R$_2$ is not phenyl or phenyl substituted by any substituent selected from halogen, hydroxy, C$_1$-C$_6$ alkyl, C$_1$-C$_6$alkoxy, nitro, —NH$_2$, or —NHCOCH$_3$.

2. A compound as claimed in claim 1 wherein R$_1$ is —NH$_2$ and R$_3$ is hydrogen, and R$_2$ is substituted phenyl, the substituent(s) in the phenyl being selected from, methylenedioxy, C$_1$-C$_6$ alkylthio, trifluoromethyl, trifluoromethoxy, nitrile (—CN), oxo, COR$^A$, CONHR$^A$, —CONR$^A$R$^B$, —NHR$^A$, NR$^A$R$^B$, —NHCOR$^C$, —NHCOOR$^A$, —NR$^B$COOR$^A$ wherein R$^A$ and R$^B$ are independently a C$_1$-C$_6$ alkyl group and wherein R$^C$ is a C$_2$-C$_6$ alkyl group.

3. A pharmaceutical composition comprising a compound as claimed in claim 1 in combination with a pharmaceutically acceptable carrier or excipients.

4. A compound selected from the group consisting of:
2-Amino-N-(2-fluorobenzyl)-6-(2-furyl)pyrimidine-4-carboxamide;
2-Amino-N-(3,4-difluorophenyl)-6-(2-furyl)pyrimidine-4-carboxamide;
2-Amino-6-(2-furyl)-N-(3-methoxybenzyl)pyrimidine-4-carboxamide;
2-Amino-6-(2-furyl)-N,N-dimethylpyrimidine-4-carboxamide;
1-(2-Amino-6-(2-furyl)pyrimidin-4-ylcarbonyl)piperidine;
2-Amino-6-(2-furyl)-N-(2-methoxybenzyl)pyrimidine-4-carboxamide;
2-Amino-6-(2-furyl)-N-(2-furylmethyl)pyrimidine-4-carboxamide;
2-Amino-6-(2-furyl)pyrimidine-4-carboxamide;
2-Amino-6-(2-furyl)-N-(4-dimethylaminobenzyl)pyrimidine-4-carboxamide;
2-Amino-6-(2-furyl)-N-(3-methylpyridin-2-ylmethyl)pyrimidine-4-carboxamide;
2-Amino-6-(2-furyl)-N-(3-(dimethylaminocarbonyl)benzyl)pyrimidine-4-carboxamide; 2-Amino-6-(2-furyl)-N-(2-pyridylmethyl)pyrimidine-4-carboxamide;
2-Amino-6-(2-furyl)-N-(4-pyridylmethyl)pyrimidine-4-carboxamide;
2-Amino-6-(2-furyl)-N-(2-methylbenzyl)pyrimidine-4-carboxamide;
2-Amino-N-(3-trifluoromethylbenzyl)-6-(2-furyl)pyrimidine-4-carboxamide;
2-Amino-N-(1H-benzimidazol-2-ylmethyl)-6-(2-furyl)pyrimidine-4-carboxamide;
2-Amino-6-(2-furyl)-N-(3-pyridylmethyl)pyrimidine-4-carboxamide;
2-Amino-6-(2-furyl)-N-(3-methylbenzyl)pyrimidine-4-carboxamide;
2-Amino-6-(2-furyl)-N-(3,6-dimethylpyridin-2-ylmethyl)pyrimidine-4-carboxamide;
2-Amino-6-(2-furyl)-N-(2-(2-thienyl)thiazol-4-ylmethyl)pyrimidine-4-carboxamide;
2-Amino-6-(2-furyl)-N-(2-thienylmethyl)pyrimidine-4-carboxamide;
2-Amino-6-(2-furyl)-N-(5-(2-pyridyl)-2-thienylmethyl)pyrimidine-4-carboxamide;
2-Amino-6-(2-furyl)-N-(5-methyl-2-trifluoromethylfuran-3-ylmethyl)pyrimidine-4-carboxamide;
2-Amino-6-(2-furyl)-N-(5-methylisoxazol-3-ylmethyl)pyrimidine-4-carboxamide;
2-Amino-6-(2-furyl)-N-(2-methoxy-6-methylpyridin-3-ylmethyl)pyrimidine-4-carboxamide;
2-Amino-N-(6-fluoro[1,3]benzodioxin-8-ylmethyl)-6-(2-furyl)pyrimidine-4-carboxamide;
2-Amino-6-(2-furyl)-N-(6-methylpyridin-3-ylmethyl)pyrimidine-4-carboxamide;
2-Amino-6-(2-furyl)-N-(3-indolylmethyl)pyrimidine-4-carboxamide;
2-Amino-6-(2-furyl)-N-(6-hydroxymethylpyridin-2-ylmethyl)pyrimidine-4-carboxamide;
2-Amino-6-(2-furyl)-N-(1-methyl-1H-imidazol-2-ylmethyl)pyrimidine-4-carboxamide;
2-Amino-6-(2-furyl)-N-(5-H-indolylmethyl)pyrimidine-4-carboxamide;
2-Amino-N-(2,3-dimethylindol-5-ylmethyl)-6-(2-furyl)pyrimidine-4-carboxamide;
2-Amino-6-(2-furyl)-N-(3-methyl-4-nitrobenzyl)pyrimidine-4-carboxamide;
2-Amino-6-(2-furyl)-N-methyl-N-(2-(2-pyridyl)ethyl)pyrimidine-4-carboxamide;
2-Amino-6-(2-furyl)-N-(2-methylindol-5-ylmethyl)pyrimidine-4-carboxamide;
2-Amino-N-benzyl-6-(2-furyl)pyrimidine-4-carboxamide;
N-Allyl-2-amino-6-(2-furyl)pyrimidine-4-carboxamide;
(R)-2-Amino-6-(2-furyl)-N-(2-hydroxypropyl)pyrimidine-4-carboxamide;
2-Amino-6-(2-furyl)-N-(6-indolylmethyl)pyrimidine-4-carboxamide;
2-Amino-6-(2-furyl)-N-(quinolin-8-ylmethyl)pyrimidine-4-carboxamide;
2-Amino-6-(2-furyl)-N-(2-(pyridin-2-yl)ethyl)pyrimidine-4-carboxamide;
2-Amino-N-(2-chlorobenzyl)-6-(2-furyl)pyrimidine-4-carboxamide;
2-Amino-6-(2-furyl)-N-(2-trifluoromethylbenzyl)pyrimidine-4-carboxamide;
2-Amino-N-([2,1,3]benzothiadiazol-5-ylmethyl)-6-(2-furyl)pyrimidine-4-carboxamide;
2-Amino-6-(2-furyl)-N-(isoquinolin-3-ylmethyl)pyrimidine-4-carboxamide;
1-(2-Amino-6-(2-furyl)pyrimidin-4-ylcarbonyl)-4-(2-pyridyl)piperazine;
2-Amino-6-(2-furyl)-N-(quinolin-2-ylmethyl)pyrimidine-4-carboxamide;
2-Amino-N-(benzothiazol-2-ylmethyl)-6-(2-furyl)pyrimidine-4-carboxamide;
(S)-2-Amino-6-(2-furyl)-N-(1-phenylethyl)pyrimidine-4-carboxamide;
2-Amino-N-(4-chlorobenzyl)-6-(2-furyl)pyrimidine-4-carboxamide;
2-Amino-N-(4-fluorobenzyl)-6-(2-furyl)pyrimidine-4-carboxamide;
(R)-2-Amino-6-(2-furyl)-N-(1-phenylethyl)pyrimidine-4-carboxamide;

2-Amino-6-(2-furyl)-N-(4-methoxybenzyl)pyrimidine-4-carboxamide;
2-Amino-N-(cyanomethyl)-6-(2-furyl)pyrimidine-4-carboxamide;
2-Amino-6-(2-furyl)-N-(4-methylbenzyl)pyrimidine-4-carboxamide;
2-Amino-6-(2-furyl)-N-(1-phenylprop-1-yl)pyrimidine-4-carboxamide;
2-Amino-N-(3-fluorobenzyl)-6-(2-furyl)pyrimidine-4-carboxamide;
2-Amino-N-(3-chlorobenzyl)-6-(2-furyl)pyrimidine-4-carboxamide;
2-Amino-6-(2-furyl)-N-(3-methylphenyl)pyrimidine-4-carboxamide;
2-Amino-6-(2-furyl)-N-(3-methylpyridin-2-yl)pyrimidine-4-carboxamide;
2-Amino-6-(2-furyl)-N-(3-phenylpropyl)pyrimidine-4-carboxamide;
2-Amino-N-(4-amino-3-methylbenzyl)-6-(2-furyl)pyrimidine-4-carboxamide;
2-Amino-N-benzyl-6-(2-furyl)-N-methylpyrimidine-4-carboxamide;
2-Amino-6-(2-furyl)-N-(5-methylpyrazin-2-ylmethyl)pyrimidine-4-carboxamide;
2-Amino-6-(2-furyl)-N-(1H-imidazol-2-ylmethyl)pyrimidine-4-carboxamide;
2-Amino-6-(2-furyl)-N-(1-n-propyl-1H-imidazol-2-ylmethyl)pyrimidine-4-carboxamide;
2-Amino-N-(2-bromobenzyl)-6-(2-furyl)pyrimidine-4-carboxamide;
2-Amino-N-(6-bromopyridin-2-ylmethyl)-6-(2-furyl)pyrimidine-4-carboxamide;
2-Amino-N-(6-aminopyridin-2-ylmethyl)-6-(2-furyl)pyrimidine-4-carboxamide;
2-Amino-6-(2-furyl)-N-(3-(1H-imidazol-1-yl)propyl)pyrimidine-4-carboxamide;
2-Amino-N (1-ethyl-1H-imidazol-2-ylmethyl)-6-(2-furyl)pyrimidine-4-carboxamide;
2-Amino-N-(2-dimethylamino-6-methylpyridin-3-ylmethyl)-6-(2-furyl)pyrimidine-4-carboxamide;
(R)-Methyl-2-(6-(2-amino-6-(2-furyl)pyrimidine-4-carboxamido)) phenylacetate;
(S)-Methyl-2-(6-(2-amino-6-(2-furyl)pyrimidine-4-carboxamido)) phenylacetate;
2-Amino-N-(2,6-dichlorobenzyl)-6-(2-furyl)pyrimidine-4-carboxamide;
2-Amino-N-(3-methylpyridin-2-ylmethyl)-6-(thiazol-2-yl)pyrimidine-4-carboxamide;
2-Amino-N-(6-n-propylpyridin-2-ylmethyl)-6-(thiazol-2-yl)pyrimidine-4-carboxamide;
2-Amino-6-(5-methyl-2-furyl)-N-(2-trifluoromethylbenzyl)pyrimidine-4-carboxamide;
2-Amino-6-(5-methyl-2-furyl)-N-(2-pyridylmethyl)pyrimidine-4-carboxamide;
2-Amino-6-(5-methyl-2-furyl)-N-(1-methyl-1H-pyrrol-2-ylmethyl)pyrimidine-4-carboxamide;
2-Amino-5-bromo-6-(5-methyl-2-furyl)-N-(2-trifluoromethylbenzyl)pyrimidine-4-carboxamide;
2-Amino-N-(2-methylbenzyl)-6-(5-methyl-2-furyl)pyrimidine-4-carboxamide;
2-Amino-N-(3-methylbenzyl)-6-(5-methyl-2-furyl)pyrimidine-4-carboxamide;
2-Amino-N-(4-methylbenzyl)-6-(5-methyl-2-furyl)pyrimidine-4-carboxamide;
2-Amino-N-(2-chlorobenzyl)-6-(5-methyl-2-furyl)pyrimidine-4-carboxamide;
2-Amino-N-(3-chlorobenzyl)-6-(5-methyl-2-furyl)pyrimidine-4-carboxamide;
2-Amino-6-(5-methyl-2-furyl)-N-(3-pyridylmethyl)pyrimidine-4-carboxamide;
2-Amino-6-(5-methyl-2-furyl)-N-(4-pyridylmethyl)pyrimidine-4-carboxamide;
2-Amino-N-(2-methoxybenzyl)-6-(5-methyl-2-furyl)pyrimidine-4-carboxamide;
2-Amino-N-(3-methoxybenzyl)-6-(5-methyl-2-furyl)pyrimidine-4-carboxamide;
2-Amino-N-(3-fluorobenzyl)-6-(5-methyl-2-furyl)pyrimidine-4-carboxamide;
2-Amino-6-(5-methyl-2-furyl)-N-(3-trifluoromethylbenzyl)pyrimidine-4-carboxamide;
2-Amino-N-(6-hydroxymethylpyridin-2-ylmethyl)-6-(5-methyl-2-furyl)pyrimidine-4-carboxamide;
2-Amino-N-(1,5-dimethyl-1H-pyrazol-3-ylmethyl)-6-(5-methyl-2-furyl)pyrimidine-4-carboxamide;
2-Amino-6-(5-methyl-2-furyl)-N-(5-methylisoxazol-3-ylmethyl)pyrimidine-4-carboxamide;
2-Amino-6-(5-methyl-2-furyl)-N-(2-phenylethyl)pyrimidine-4-carboxamide;
2-Amino-6-(5-methyl-2-furyl)-N-(3-phenylpropyl)pyrimidine-4-carboxamide;
2-Amino-N-benzyl-N-ethyl-6-(5-methyl-2-furyl)pyrimidine-4-carboxamide;
(R,S)-2-Amino-6-(5-methyl-2-furyl)-N-(1-phenylpropyl)pyrimidine-4-carboxamide;
2-Amino-N-(1,5-dimethyl-1H-pyrrol-2-ylmethyl)-6-(5-methyl-2-furyl)pyrimidine-4-carboxamide;
(R,S)-2-Amino-6-(5-methyl-2-furyl)-N-(1-phenylethyl) pyrimidine-4-carboxamide;
(S)-2-Amino-N-methyl-6-(5-methyl-2-furyl)-N-(1-phenylethyl)pyrimidine-4-carboxamide;
2-Amino-6-(5-methyl-2-furyl)-N-(1-phenylprop-2-yl)pyrimidine-4-carboxamide;
2-Amino-N-isobutyl-6-(5-methyl-2-furyl)pyrimidine-4-carboxamide;
2-Amino-N-hexyl-6-(5-methyl-2-furyl)pyrimidine-4-carboxamide;
2-Amino-N-butyl-N-methyl-6-(5-methyl-2-furyl)pyrimidine-4-carboxamide;
2-Amino-N-methyl-6-(5-methyl-2-furyl)-N-pentylpyrimidine-4-carboxamide;
2-Amino-N-benzyl-6-(5-methyl-2-furyl)pyrimidine-4-carboxamide;
2-Amino-6-(5-methyl-2-furyl)-N-phenylpyrimidine-4-carboxamide;
2-Amino-N-benzyl-6-(4-methylthiazol-2-yl)pyrimidine-4-carboxamide;
2-Amino-6-(5-methyl-2-furyl)-N-(1-methyl-1H-pyrazol-5-ylmethyl)pyrimidine-4-carboxamide;
2-Amino-N-(1-methyl-1H-pyrazol-5-ylmethyl-6-(4-methylthiazol-2-yl)pyrimidine-carboxamide;
2-Amino-6-(4-methylthiazol-2-yl)-N-(pyridin-2-ylmethyl)pyrimidine-4-carboxamide;
2-Amino-6-(4-methylthiazol-2-yl)-N-(2-trifluoromethylbenzyl)pyrimidine-4-carboxamide;
2-Amino-N-(1,5-dimethyl-1H-pyrazol-3-ylmethyl)-6-(4-methylthiazol-2-yl)pyrimidine-4-carboxamide;
2-Amino-6-(5-methyl-2-furyl)-N-(1-methyl-1H-pyrazol-3-ylmethyl)pyrimidine-4-carboxamide;
2-Amino-N-(1-methyl-1H-pyrazol-3-ylmethyl)-6-(4-methylthiazol-2-yl)pyrimidine-4-carboxamide;
N-(1,5-Dimethyl-1H-pyrazol-3-ylmethyl)-6-(5-methyl-2-furyl)pyrimidine-4-carboxamide;

645-Methyl-2-furyl)-N-(2-trifluoromethylbenzyl)pyrimidine-4-carboxamide;
N-Benzyl-6-(5-methyl-2-furyl)pyrimidine-4-carboxamide;
6-(5-Methyl-2-furyl)-N-(2-pyridylmethyl)pyrimidine-4-carboxamide;
N-(3,6-Dimethylpyridin-2-ylmethyl)-6-(5-methyl-2-furyl)pyrimidine-4-carboxamide;
2-Amino-N-(1,3-dimethyl-1H-pyrazol-5-ylmethyl)-6-(5-methyl-2-furyl)pyrimidine-4-carboxamide;
2-Amino-N-(1,3-dimethyl-1H-pyrazol-5-ylmethyl)-6-(4-methylthiazol-2-yl)pyrimidine-4-carboxamide;
2-Amino-6-(5-methyl-2-furyl)-N-(6-methylpyridin-2-ylmethyl)pyrimidine-4-carboxamide;
2-Amino-6-(5-methyl-2-furyl)-N-(1-methyl-1H-pyrazol-4-ylmethyl)pyrimidine-4-carboxamide;
2-Amino-6-(4-methylthiazol-2-yl)-N-(pyrimidin-4-ylmethyl)pyrimidine-4-carboxamide;
2-Amino-6-(4-methylthiazol-2-yl)-N-(4-methylthiazol-2-ylmethyl)pyrimidine-4-carboxamide;
2-Amino-N-(1,5-dimethyl-1H-pyrazol-4-ylmethyl-6-(4-methylthiazol-2-yl)pyrimidine-4-carboxamide;
2-Amino-N-(1,3-dimethyl-1H-pyrazol-4-ylmethyl)-6-(4-methylthiazol-2-yl)pyrimidine-4-carboxamide;
2-Amino-6-(4-methylthiazol-2-yl)-N-(pyridin-3-ylmethyl)pyrimidine-4-carboxamide;
2-Amino-6-(4-methylthiazol-2-yl)-N-(3-trifluoromethylbenzyl)pyrimidine-4-carboxamide;
2-Amino-N-(2-methylbenzyl)-6-(4-methylthiazol-2-yl)pyrimidine-4-carboxamide;
2-Amino-N-(3-methoxybenzyl)-6-(4-methylthiazol-2-yl)pyrimidine-4-carboxamide;
2-Amino-N-(3-methylbenzyl)-6-(4-methylthiazol-2-yl)pyrimidine-4-carboxamide;
2-Amino-N-(3-fluorobenzyl)-6-(4-methylthiazol-2-yl)pyrimidine-4-carboxamide;
2-Amino-N-(3-chlorobenzyl)-6-(4-methylthiazol-2-yl)pyrimidine-4-carboxamide;
2-Amino-N-(6-methylpyridin-2-ylmethyl)-6-(4-methylthiazol-2-yl)pyrimidine-4-carboxamide;
2-Amino-6-phenyl-N-(2-trifluoromethylbenzyl)pyrimidine-4-carboxamide;
2-Amino-6-phenyl-N-(pyridin-2-ylmethyl)pyrimidine-4-carboxamide;
2-Amino-6-(2-methylphenyl)-N-(pyridin-2-ylmethyl)pyrimidine-4-carboxamide;
2-Amino-6-(4-methylphenyl)-N-(pyridin-2-ylmethyl)pyrimidine-4-carboxamide;
2-Amino-6-(3-cyanophenyl)-N-(pyridin-2-ylmethyl)pyrimidine-4-carboxamide;
2-Amino-6-(2-methylphenyl)-N-(3-methylpyridin-2-ylmethyl)pyrimidine-4-carboxamide;
2-Amino-6-(3-methylphenyl)-N-(3-methylpyridin-2-ylmethyl)pyrimidine-4-carboxamide;
2-Amino-6-(4-methylphenyl)-N-(3-methylpyridin-2-ylmethyl)pyrimidine-4-carboxamide;
2-Amino-6-(3-cyanophenyl)-N-(3-methylpyridin-2-ylmethyl)pyrimidine-4-carboxamide;
2-Amino-6-(3-methylphenyl)-N-(pyridin-2-ylmethyl)pyrimidine-4-carboxamide;
2-Amino-6-(3-methoxyphenyl)-N-(pyridin-2-ylmethyl)pyrimidine-4-carboxamide;
2-Amino-6-(3-methoxyphenyl)-N-(3-methylpyridin-2-ylmethyl)pyrimidine-4-carboxamide; and
2-Amino-N-(3-methylpyridin-2-ylmethyl)-6-phenylpyrimidine-4-carboxamide.

* * * * *

UNITED STATES PATENT AND TRADEMARK OFFICE
CERTIFICATE OF CORRECTION

| | | |
|---|---|---|
| PATENT NO. | : 7,875,600 B2 | |
| APPLICATION NO. | : 10/588757 | |
| DATED | : January 25, 2011 | |
| INVENTOR(S) | : Roger John Gillespie et al. | |

It is certified that error appears in the above-identified patent and that said Letters Patent is hereby corrected as shown below:

In Column 133, Claim 4, Line 1:
   Please replace "645" with --6-(5--

Signed and Sealed this
Seventeenth Day of May, 2011

David J. Kappos
*Director of the United States Patent and Trademark Office*